(12) United States Patent
Hasegawa et al.

(10) Patent No.: US 8,795,946 B2
(45) Date of Patent: *Aug. 5, 2014

(54) POLYMERIZABLE ESTER COMPOUND, POLYMER, RESIST COMPOSITION, AND PATTERNING PROCESS

(75) Inventors: Koji Hasegawa, Joetsu (JP); Masayoshi Sagehashi, Joetsu (JP); Yuuki Suka, Joetsu (JP); Masashi Ilo, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/548,654

(22) Filed: Jul. 13, 2012

(65) Prior Publication Data

US 2013/0017484 A1    Jan. 17, 2013

(30) Foreign Application Priority Data

Jul. 14, 2011 (JP) ................................. 2011-155417

(51) Int. Cl.
| | | |
|---|---|---|
| G03F 7/039 | (2006.01) | |
| G03F 7/20 | (2006.01) | |
| G03F 7/30 | (2006.01) | |
| G03F 7/38 | (2006.01) | |
| C08F 24/00 | (2006.01) | |

(52) U.S. Cl.
USPC ........ 430/270.1; 430/311; 430/326; 430/330; 430/907; 430/910; 430/921; 430/925; 430/942; 526/268; 526/270; 549/464

(58) Field of Classification Search
None
See application file for complete search history.

(56) References Cited

U.S. PATENT DOCUMENTS

| | | |
|---|---|---|
| 6,280,898 B1 | 8/2001 | Hasegawa et al. |
| 6,312,867 B1 | 11/2001 | Kinsho et al. |
| 6,329,125 B2 | 12/2001 | Takechi et al. |
| 6,448,420 B1 | 9/2002 | Kinsho et al. |
| 6,830,866 B2 | 12/2004 | Kobayashi et al. |
| 7,186,495 B2 | 3/2007 | Maeda et al. |
| 7,311,948 B2 | 12/2007 | Lub et al. |
| 8,388,860 B2 | 3/2013 | Goldfinger et al. |
| 2009/0274978 A1 | 11/2009 | Ohashi et al. |
| 2010/0297553 A1* | 11/2010 | Kanda et al. ............... 430/270.1 |
| 2012/0288794 A1* | 11/2012 | Bae et al. ................... 430/270.1 |
| 2012/0288796 A1* | 11/2012 | Katayama et al. .......... 430/285.1 |
| 2013/0017492 A1* | 1/2013 | Hatakeyama et al. ..... 430/285.1 |

FOREIGN PATENT DOCUMENTS

| | | |
|---|---|---|
| JP | 4-39665 A | 2/1992 |
| JP | 9-90637 A | 4/1997 |
| JP | 2000-26446 A | 1/2000 |
| JP | 2000-159758 A | 6/2000 |
| JP | 2000-327633 A | 11/2000 |
| JP | 2000-336121 A | 12/2000 |
| JP | 2003-66612 A | 3/2003 |
| JP | 2005-505577 A | 2/2005 |
| JP | 2009-269953 A | 11/2009 |
| JP | 2010-536782 A | 12/2010 |

OTHER PUBLICATIONS

Arimitsu et al., "Effect of Phenolic Hydroxyl Residues on the Improvement of Acid-Proliferation-Type Photoimaging Materials", Journal of Photopolymer Science and Technology, vol. 9, No. 1, 1996, pp. 29-30.

Arimitsu et al., "Sensitivity Enhancement of Chemical-Amplification-Type Photoimaging Materials by Acetoacetic Acid Derivatives", Journal of Photopolymer Science and Technology, vol. 8, No. 1, 1995, pp. 43-44.

Kudo et al., "Enhancement of the Sensitivity of Chemical-Amplification-Type Photoimaging Materials by β-Tosyloxyketone Acetals", Journal of Photopolymer Science and Technology, vol. 8, No. 1, 1995, pp. 45-46.

* cited by examiner

*Primary Examiner* — Sin J. Lee
(74) *Attorney, Agent, or Firm* — Birch, Stewart, Kolasch & Birch, LLP

(57) ABSTRACT

Polymerizable ester compounds having formula (1) are novel wherein $R^1$ is H, F, methyl or trifluoromethyl, $R^2$ is an acid labile group, Aa is a divalent hydrocarbon group which may be separated by —O— or —C(=O)—, and $k^1$ is 0 or 1. They are useful as monomers to produce polymers which are transparent to radiation ≤500 nm. Radiation-sensitive resist compositions comprising the polymers as base resin exhibit excellent developed properties.

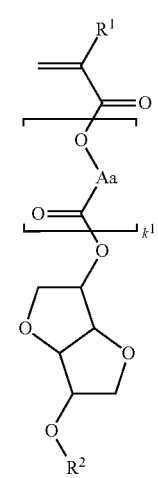

(1)

9 Claims, No Drawings

POLYMERIZABLE ESTER COMPOUND, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2011-155417 filed in Japan on Jul. 14, 2011, the entire contents of which are hereby incorporated by reference.

TECHNICAL FIELD

This invention relates to (1) polymerizable ester compounds useful as raw materials for the synthesis of functional materials, pharmaceutical and agricultural chemicals, (2) polymers comprising recurring units derived from the ester compounds, (3) resist compositions comprising the polymers, and (4) a patterning process using the resist compositions.

BACKGROUND ART

The recent drive for higher integration and operating speeds in LSI devices makes it necessary to further reduce the pattern rule. Deep-ultraviolet lithography was developed as an essential technology for micropatterning to a feature size of 0.3 μm or less. Among others, the KrF excimer laser lithography has been fully recognized as a commercial scale production technology.

With respect to chemically amplified resist compositions adapted for the photolithography using ArF excimer laser light of 193 nm wavelength as a light source, the primary requirement is, of course, a high transparency at that wavelength. They are also required to meet a high etch resistance sufficient to comply with film thickness reduction, a high sensitivity sufficient to minimize the burden to expensive optical materials, and among others, a high resolution sufficient to form an exact fine pattern. The key toward these requirements is to develop a base resin featuring high transparency, high rigidity and high reactivity. Active efforts have been devoted for such development.

Typical resins known to be highly transparent to ArF excimer laser light are copolymers of acrylic or methacrylic acid derivatives as disclosed in JP-A H04-39665.

One of the (meth)acrylic resins proposed thus far is a combination of (meth)acrylic units having methyladamantane ester as acid labile group units with (meth)acrylic units having lactone ring ester as adhesive group units as disclosed in JP-A H09-90637. Acid labile groups of exo form are described in U.S. Pat. No. 6,448,420 (JP-A 2000-327633). These groups have so high an acid elimination ability and require a low level of activation energy for acid elimination, affording a high resolution and low dependence on post-exposure bake (PEB). Norbornane lactone is also proposed as an adhesive group having enhanced etching resistance as disclosed in JP-A 2000-26446 and JP-A 2000-159758. These studies have achieved significant improvements in the resolution of ArF resists.

However, in an attempt to form a fine pattern having a pitch of less than 200 nm, prior art resist materials are difficult to form patterns and the patterns, if formed, have insufficient rectangularity and substantial roughness on their surface and sidewalls. They are hardly believed to clear the practically acceptable level. Of the problems associated with prior art resist materials, the most serious problem is the unevenness of fine line size, which is generally referred to as "line edge roughness" (LER). Since the LER has a substantial impact on the performance of semiconductor devices being fabricated, it is strongly desired to overcome this problem. If it is merely desired to form patterns in smooth finish, the purpose may be attained to some extent by using a resin having a relatively low molecular weight or by selecting a photoacid generator capable of generating a rather mobile acid. These attempts, however, substantially sacrifice other properties such as exposure dose dependency, pattern density dependency, and mask fidelity. Additionally, they do not lead to a reduction of LER since a fine fluctuation of a mask is so exaggerated that the line size itself becomes rather uneven. It is desired to have an essential solution to improve LER without degradation of resolution so that the solution may accommodate a further miniaturization of the ArF excimer laser lithography and a higher resolution by virtue of the immersion lithography process.

Citation List
Patent Document 1: JP-A H04-39665
Patent Document 2: JP-A H09-90637
Patent Document 3: U.S. Pat. No. 6,448,420 (JP-A 2000-327633)
Patent Document 4: JP-A 2000-26446
Patent Document 5: JP-A 2000-159758

SUMMARY OF THE INVENTION

An object of the present invention is to provide polymerizable ester compounds useful as monomers for the synthesis of polymers, polymers comprising recurring units derived from the ester compounds, and resist compositions comprising the polymers, the resist compositions exhibiting a high resolution and minimized pattern edge roughness when processed by photolithography using high-energy radiation such as ArF excimer laser radiation as a light source, especially immersion lithography. Another object is to provide a patterning process using the resist compositions.

The inventors have found that a polymerizable ester compound of the general formula (1) shown below can be readily prepared in high yields, and that a resist composition comprising a polymer having recurring units derived from the ester compound as a base resin exhibits satisfactory properties including exposure dose dependency, pattern density dependency, and mask fidelity as well as minimized pattern edge roughness when processed by photolithography. Thus the polymer is advantageously used in resist material, typically chemically amplified positive resist material for precise micropatterning.

Accordingly, the present invention provides a polymerizable ester compound, polymer, resist composition, and patterning process, as defined below.

In a first aspect, the invention provides a polymerizable ester compound having the general formula (1):

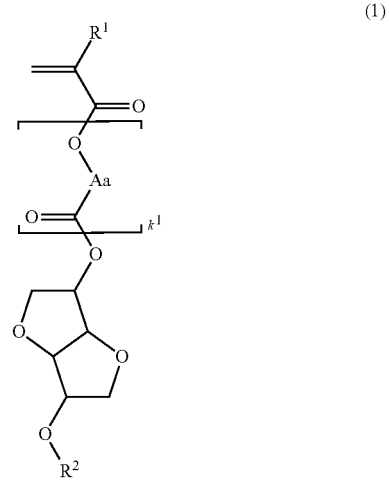

wherein $R^1$ is hydrogen, fluorine, methyl or trifluoromethyl, $R^2$ is an acid labile group, Aa is a $C_1$-$C_{10}$ straight, branched or cyclic, divalent hydrocarbon group in which a constituent —$CH_2$— may be substituted by —O— or —C(=O)—, and $k^1$ is 0 or 1.

In another aspect, the invention provides a polymerizable ester compound having the general formula (2):

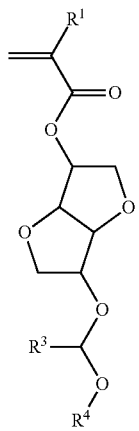

(2)

wherein $R^1$ is hydrogen, fluorine, methyl or trifluoromethyl, $R^3$ is hydrogen or a $C_1$-$C_{15}$ straight, branched or cyclic, monovalent hydrocarbon group, and $R^4$ is a $C_1$-$C_{15}$ straight, branched or cyclic, monovalent hydrocarbon group in which a constituent —$CH_2$— may be substituted by —O— or —C(=O)—.

In a second aspect, the invention provides a polymer comprising recurring units having the general formula (2a) or (2b):

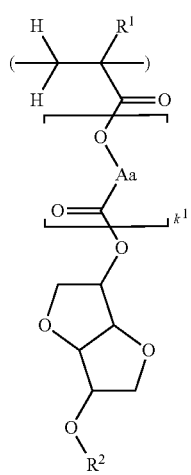

(2a)

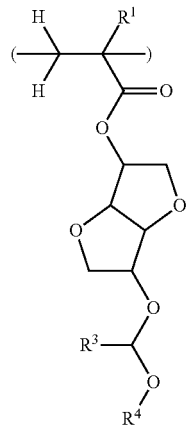

(2b)

wherein $R^1$ is hydrogen, fluorine, methyl or trifluoromethyl, $R^2$ is an acid labile group, $R^3$ is hydrogen or a $C_1$-$C_{15}$ straight, branched or cyclic, monovalent hydrocarbon group, $R^4$ is a $C_1$-$C_{15}$ straight, branched or cyclic, monovalent hydrocarbon group in which a constituent —$CH_2$— may be substituted by —O— or —C(=O)—, Aa is a $C_1$-$C_{10}$ straight, branched or cyclic, divalent hydrocarbon group in which a constituent —$CH_2$— may be substituted by —O— or —C(=O)—, and $k^1$ is 0 or 1.

In a preferred embodiment, the polymer may further comprise recurring units of at least one type selected from the general formulas (2A) to (2D).

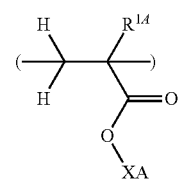

(2A)

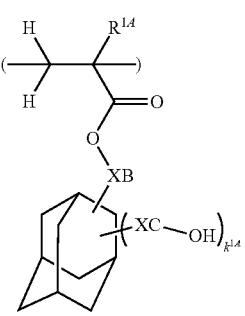

(2B)

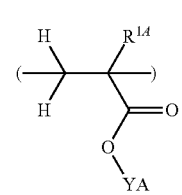

(2C)

-continued (2D)

$$\left(\begin{array}{c}H\\-C\\H\end{array}\begin{array}{c}R^{14}\\-C\\\end{array}\right)\begin{array}{c}\\ \\ C=O\\ \\ O\\ \\ ZA\end{array}$$

Herein $R^{14}$ is hydrogen, fluorine, methyl or trifluoromethyl, XA is an acid labile group, XB and XC are each independently a single bond, or a $C_1$-$C_4$ straight or branched divalent hydrocarbon group, YA is a substituent group having a lactone or sultone structure, ZA is hydrogen, a $C_1$-$C_{15}$ fluoroalkyl group, or a $C_1$-$C_{15}$ fluoroalcohol-containing substituent group, and $k^{14}$ is an integer of 1 to 3.

In a preferred embodiment, the polymer may further comprise recurring units of at least one type selected from the general formulas (d1) to (d3).

(d1)

$$\left(\begin{array}{c}R^{20}\\-\end{array}\right)_{d1}$$
$$R^{21}$$
$$R^{22}-\overset{+}{\underset{M^-}{S}}-R^{23}$$

(d2)

$$\left(\begin{array}{c}R^{24}\\-\end{array}\right)_{d2}$$
$$O\quad O\quad R^{25}$$
$$F_3C\underset{F_2}{\overset{|}{C}}\,SO_3^-\quad \overset{+}{\underset{R^{27}}{S}}-R^{26}$$

(d3)

$$\left(\begin{array}{c}R^{28}\\-\end{array}\right)_{d3}$$
$$Z_0\quad R^{29}$$
$$\quad SO_3^-\quad \overset{+}{\underset{R^{31}}{S}}-R^{30}$$

Herein $R^{20}$, $R^{24}$ and $R^{28}$ each are hydrogen or methyl, $R^{21}$ is a single bond, phenylene, —O—$R^{33}$—, or —C(=O)—Y—$R^{33}$—, Y is oxygen or NH, $R^{33}$ is a $C_1$-$C_6$ straight, branched or cyclic alkylene group, alkenylene group or phenylene group, which may contain a carbonyl (—CO—), ester (—COO—), ether (—O—) or hydroxyl radical $R^{22}$, $R^{23}$, $R^{25}$, $R^{26}$, $R^{27}$, $R^{29}$, $R^{30}$, and $R^{31}$ are each independently a $C_1$-$C_{12}$ straight, branched or cyclic alkyl group which may contain a carbonyl, ester or ether radical, or $C_6$-$C_{12}$ aryl group, $C_7$-$C_{20}$ aralkyl group or thiophenyl group, $Z_0$ is a single bond, methylene, ethylene, phenylene, fluorinated phenylene, —O—$R^{32}$—, or —C(=O)—$Z_1$—$R^{32}$—, $Z_1$ is oxygen or NH, $R^{32}$ is a $C_1$-$C_6$ straight, branched or cyclic alkylene, alkenylene or phenylene group, which may contain a carbonyl, ester, ether or hydroxyl radical, and $M^-$ is a non-nucleophilic counter ion.

In a third aspect, the invention provides a resist composition comprising a base resin comprising the polymer defined herein, an acid generator, and an organic solvent.

Also contemplated herein is a resist composition comprising a base resin comprising the polymer further having units of formulas (d1) to (d3), and an organic solvent.

In a fourth aspect, the invention provides:

a process for forming a pattern comprising the steps of applying the resist composition defined herein onto a substrate, baking the resist composition to form a resist film, exposing the resist film to high-energy radiation or electron beam through a photomask, optionally baking the exposed film, and developing it in a developer;

a process for forming a pattern comprising the steps of applying the resist composition defined herein onto a substrate, baking the resist composition to form a resist film, exposing the resist film to high-energy radiation or electron beam through a photomask, baking the exposed film, and developing it in a developer, wherein the exposing step is performed by immersion lithography including holding a liquid having a high refractive index of at least 1.0 between the resist film and a projection lens; or a process for forming a pattern comprising the steps of applying the resist composition defined herein onto a substrate, baking the resist composition to form a resist film, forming a protective film on the resist film, exposing the resist film to high-energy radiation or electron beam through a photomask, baking the exposed film, and developing it in a developer, wherein the exposing step is performed by immersion lithography including holding a liquid having a high refractive index of at least 1.0 between the protective film and a projection lens.

Advantageous Effects of Invention

The polymerizable ester compounds of the invention are useful as raw materials for the synthesis of functional materials, pharmaceutical and agricultural chemicals. They are most useful as monomers to produce polymers for the manufacture of radiation-sensitive resist compositions which have high transparency to radiation having a wavelength of up to 500 nm, especially up to 300 nm, typically KrF, ArF, and $F_2$ laser light, and exhibit good development properties. Radiation-sensitive resist compositions comprising the polymers as base resin are improved in exposure dose dependency, pattern density dependency (or optical proximity effect) and mask fidelity, and minimized in pattern edge roughness when processed by photolithography. The polymers are advantageously used in resist material, typically chemically amplified positive resist material, for precise micropatterning.

DESCRIPTION OF THE PREFERRED EMBODIMENT

The singular forms "a," "an" and "the" include plural referents unless the context clearly dictates otherwise. The notation (Cn-Cm) means a group containing from n to m carbon atoms per group. In structural formulas, the broken line indicates a valence bond.

It is understood that for many structures represented by chemical formulas, there can exist enantiomers and diastereomers. Unless otherwise stated, a single formula collectively represents all such stereoisomers. The stereoisomers may be used alone or in admixture.

The abbreviations and acronyms have the following meaning.

Mw: weight average molecular weight
GPC: gel permeation chromatography
PEB: post-exposure bake
PAG: photoacid generator Ester Compound The polymerizable ester compounds of the invention have the general formula (1).

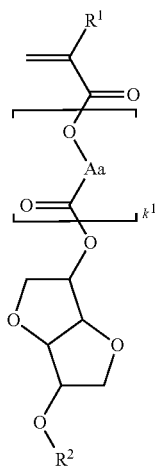

(1)

Herein $R^1$ is hydrogen, fluorine, methyl or trifluoromethyl, $R^2$ is an acid labile group, Aa is a $C_1$-$C_{10}$, preferably $C_1$-$C_6$, straight, branched or cyclic, divalent hydrocarbon group, typically alkylene, in which a constituent —$CH_2$— may be substituted by —O— or —C(=O)—, and $k^1$ is 0 or 1.

The acid labile group represented by $R^2$ may be selected from protective groups for alcoholic hydroxyl. Examples of the acid labile group are groups of the following general formulas (R1-1) and (R1-2), tertiary alkyl groups of 4 to 20 carbon atoms, preferably 4 to 15 carbon atoms, trialkylsilyl groups in which each alkyl moiety has 1 to 5 carbon atoms, oxoalkyl groups of 4 to 15 carbon atoms, and acyl groups of 1 to 10 carbon atoms.

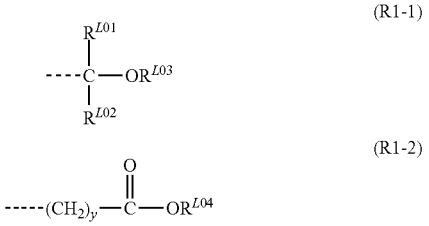

In these formulas, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

-continued

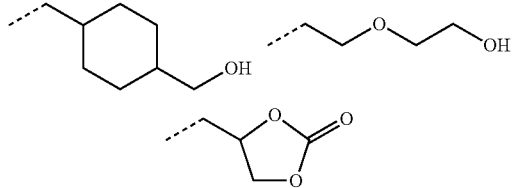

A pair of $R^{L01}$ and $R^{L02}$, $R^{L01}$ and $L^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (R1-1). The subscript y is an integer of 0 to 6.

Of the groups represented by $R^2$ and $R^{L04}$, exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Exemplary acyl groups are formyl, acetyl, ethylcarbonyl, pivaloyl, methoxycarbonyl, ethoxycarbonyl, tert-butoxycarbonyl, trifluoroacetyl, and trichloroacetyl.

Of the protective groups of formula (R1-1), the straight and branched ones are exemplified by the following groups.

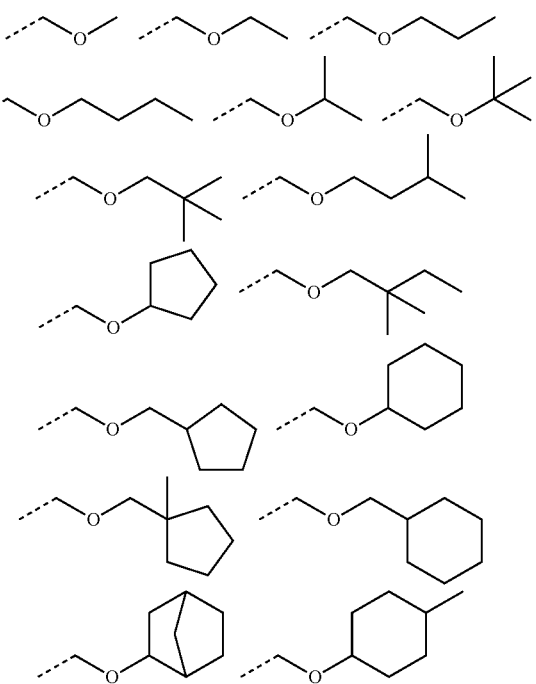

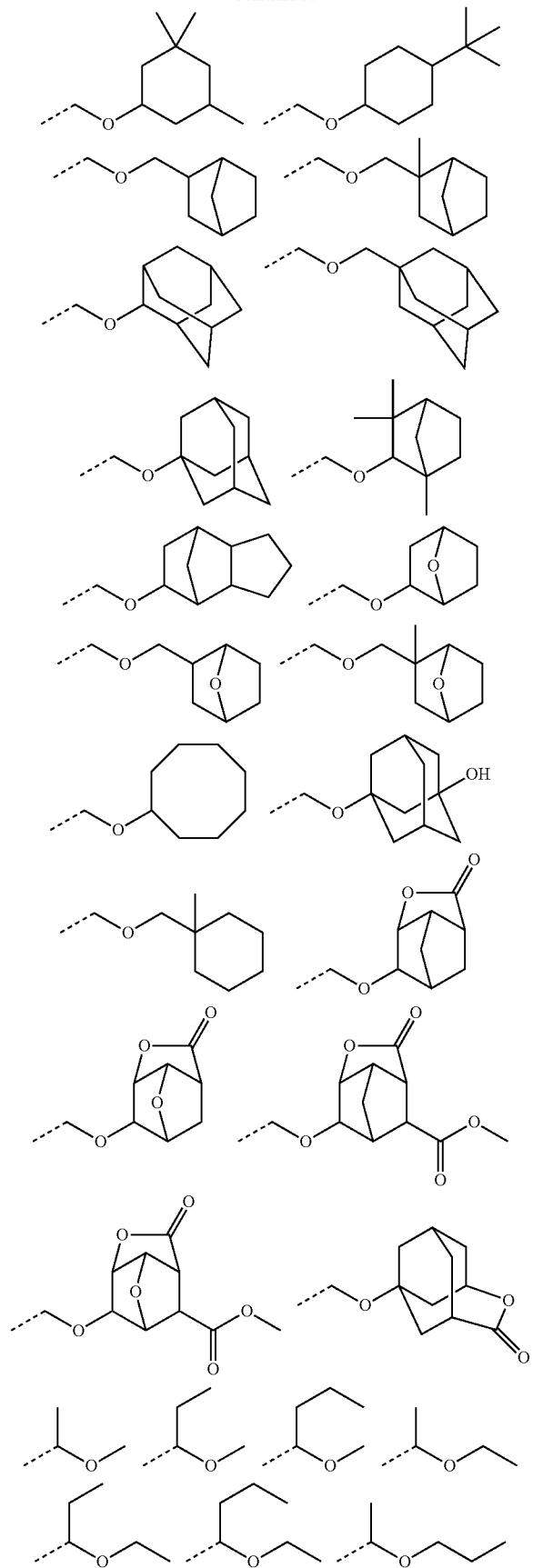
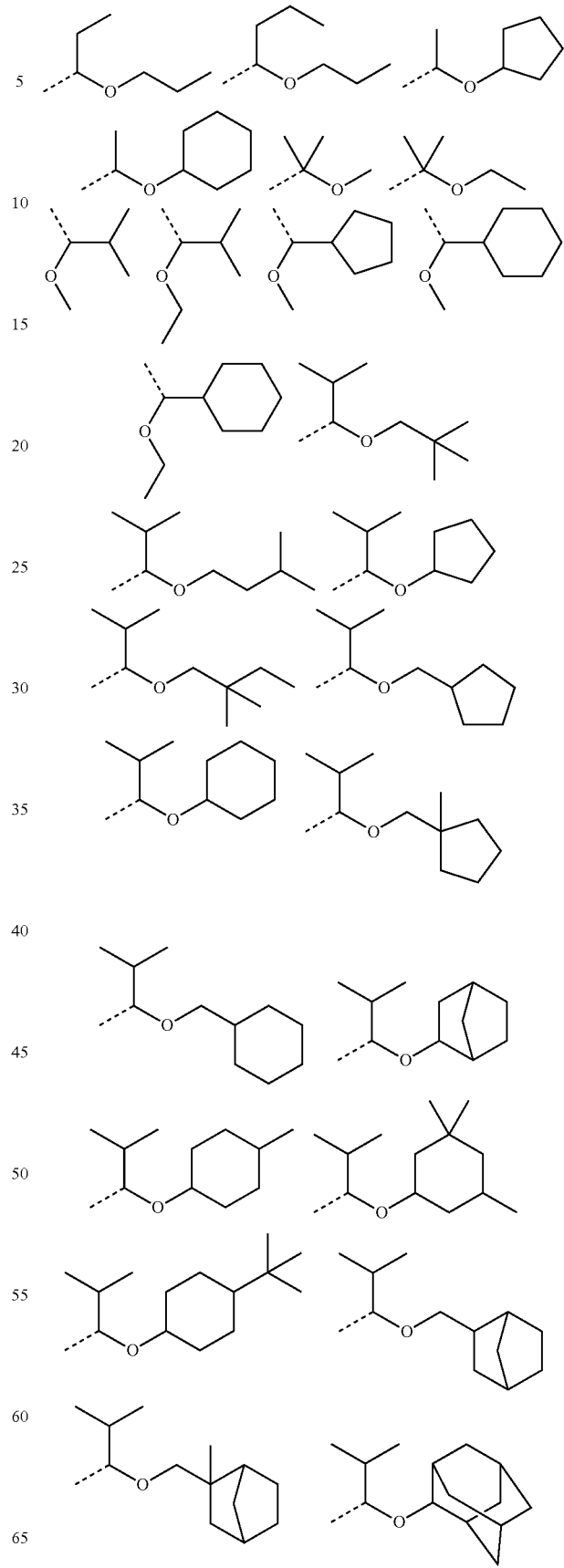

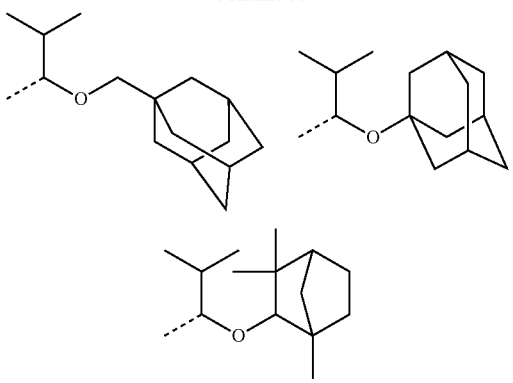

Of the protective groups of formula (R1-1), the cyclic ones are, for example, tetrahydrofuran-2-yl, 2-methyltetrahydrofuran-2-yl, tetrahydropyran-2-yl, and 2-methyltetrahydropyran-2-yl.

Examples of the protective groups of formula (R1-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the $C_1$-$C_{10}$ straight, branched or cyclic, divalent hydrocarbon group represented by Aa are given below.

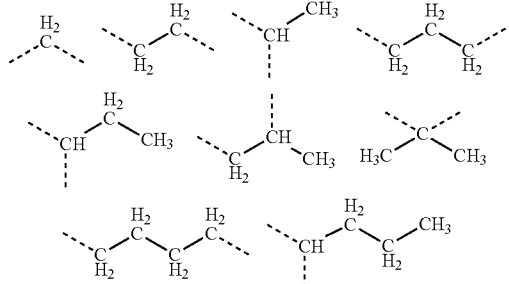

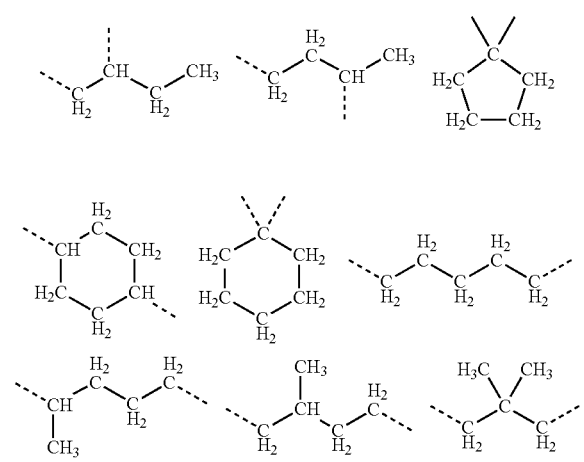

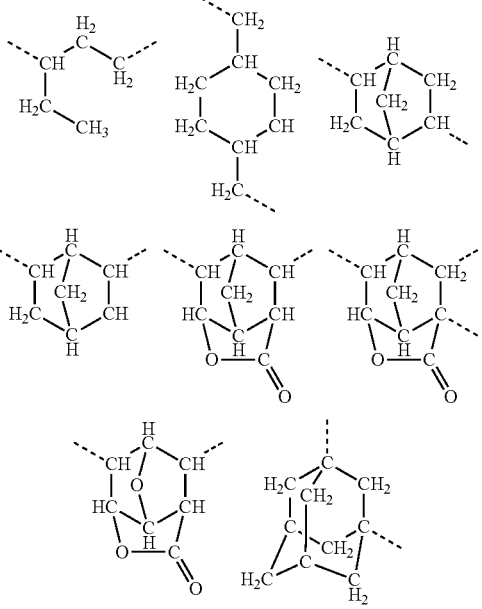

Another embodiment of the invention is a polymerizable ester compound having the general formula (2).

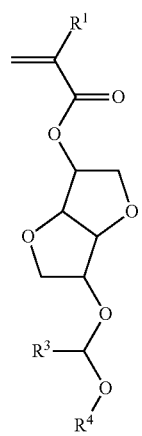

(2)

Herein $R^1$ is hydrogen, fluorine, methyl or trifluoromethyl, $R^3$ is hydrogen or a $C_1$-$C_{15}$ straight, branched or cyclic, monovalent hydrocarbon group, and $R^4$ is a $C_1$-$C_{15}$ straight, branched or cyclic, monovalent hydrocarbon group in which a constituent —$CH_2$— may be substituted by —O— or —C(=O)—.

Typical of the $C_1$-$C_{15}$ straight, branched or cyclic, monovalent hydrocarbon groups represented by $R^3$ and $R^4$ are alkyl groups, examples of which include methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl.

Examples of the compounds having formulas (1) and (2) are shown below.

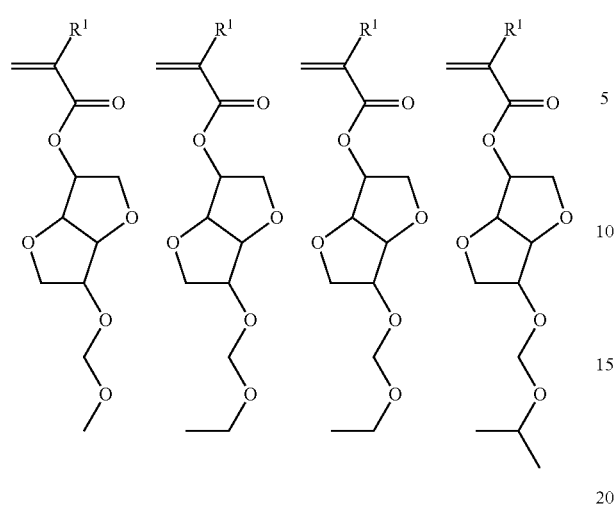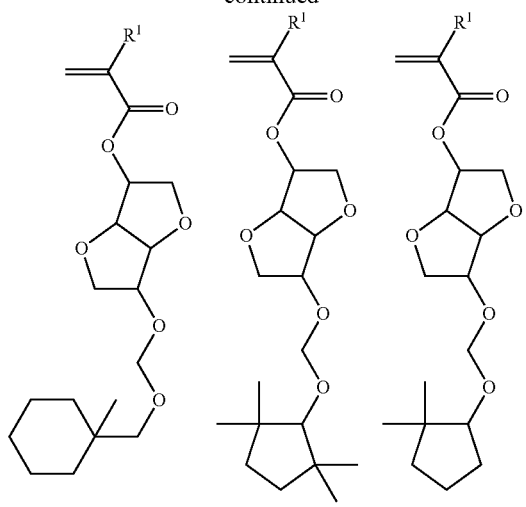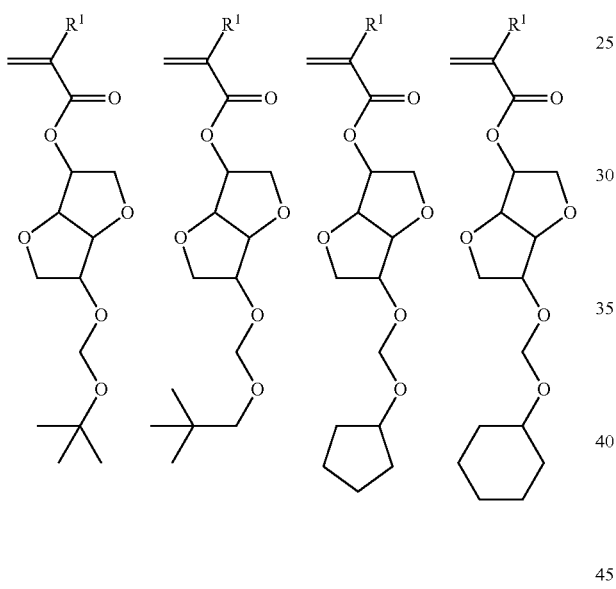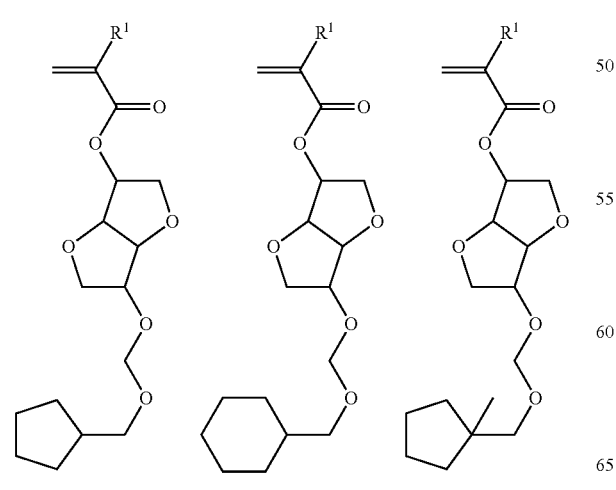

-continued
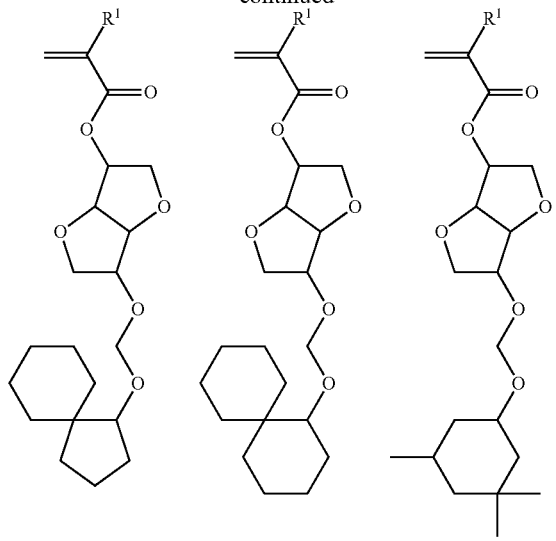
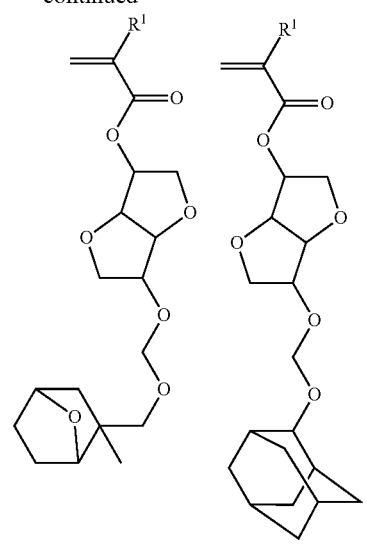
-continued
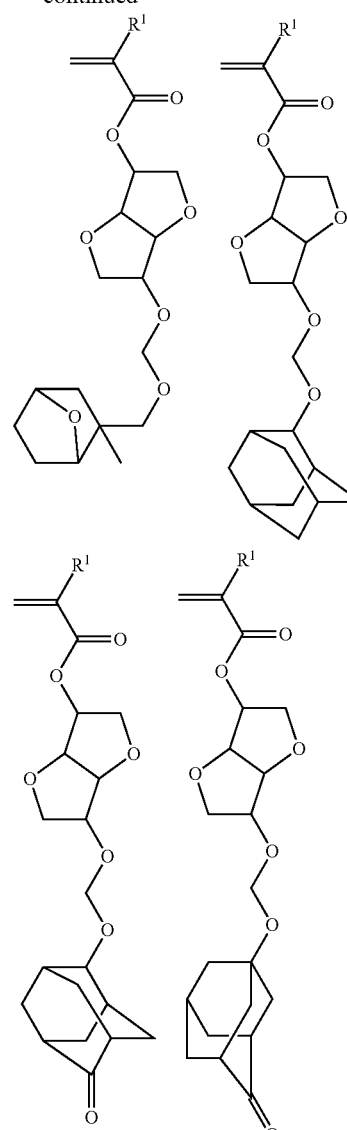
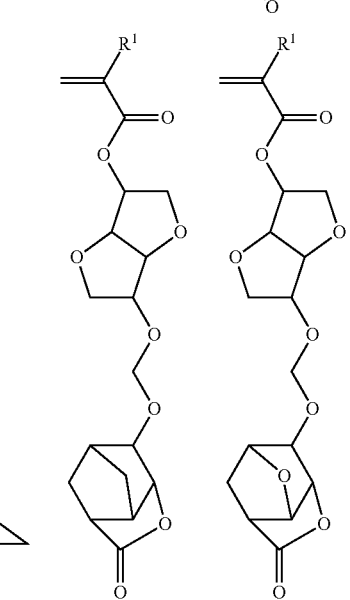

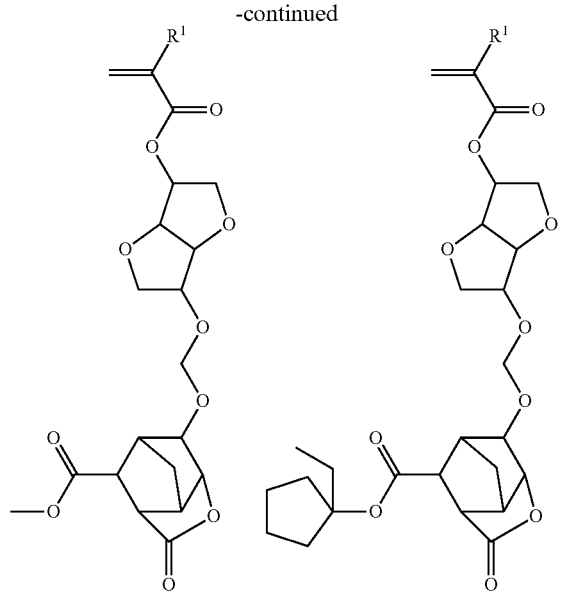
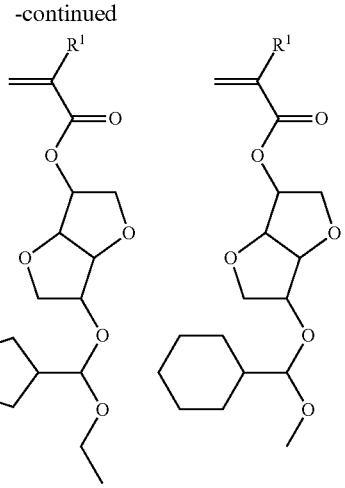
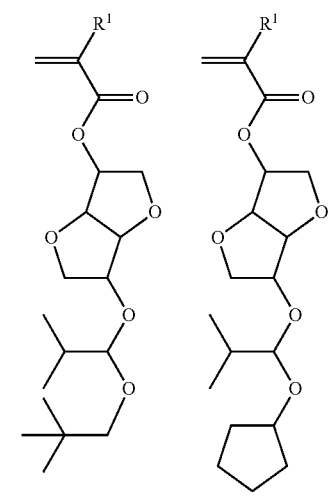
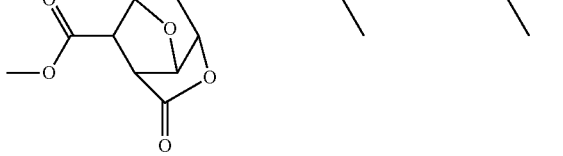
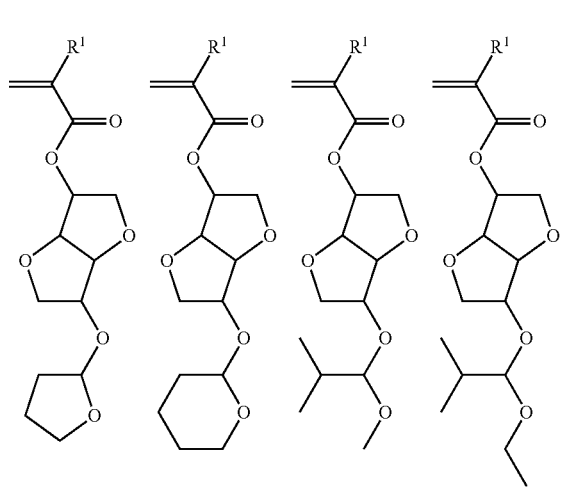
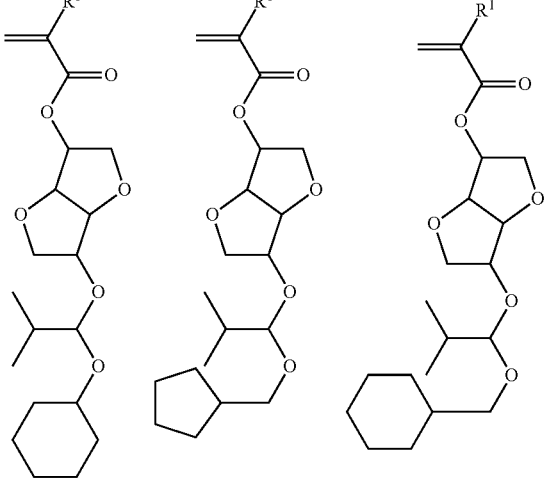

19
-continued
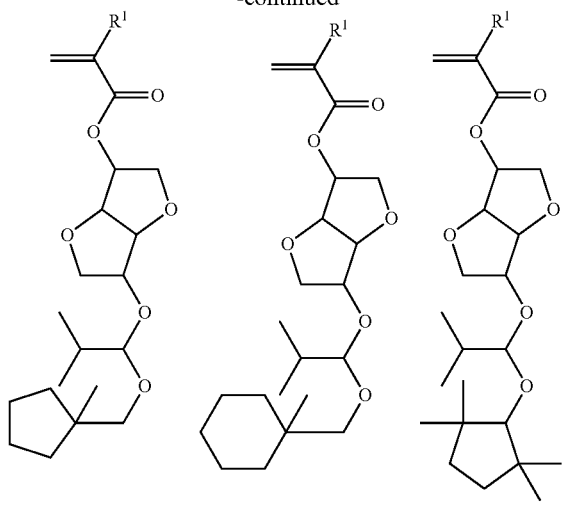
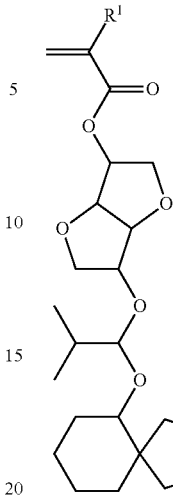
20
-continued
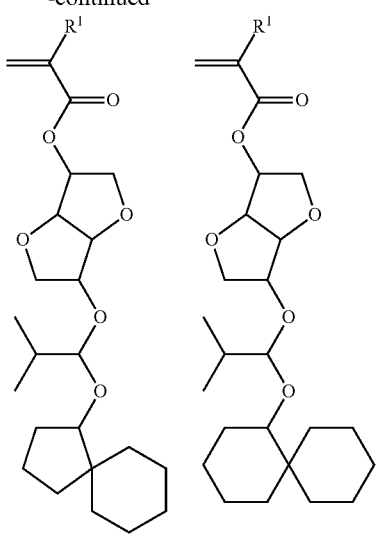
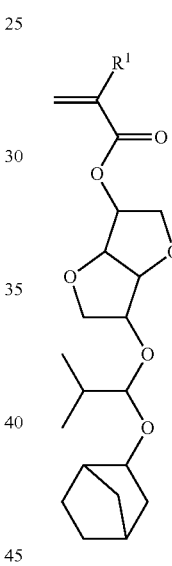
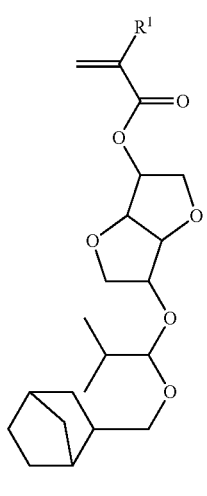
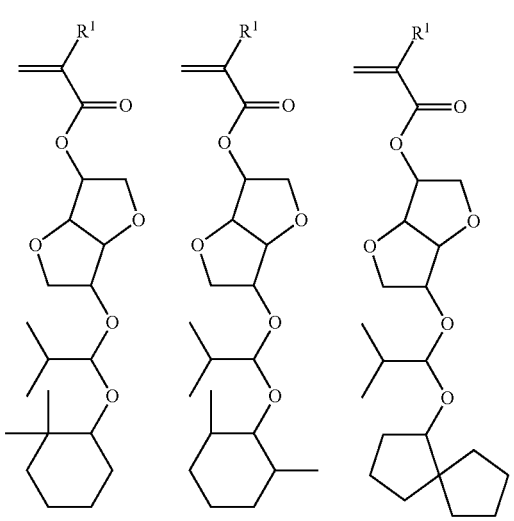
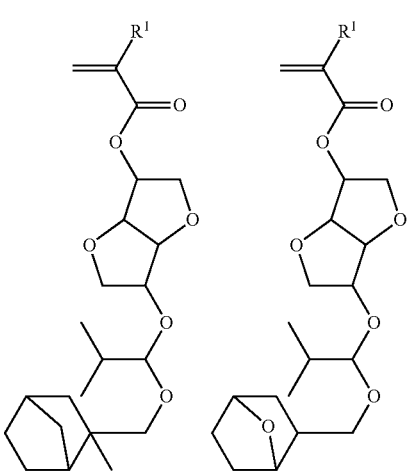

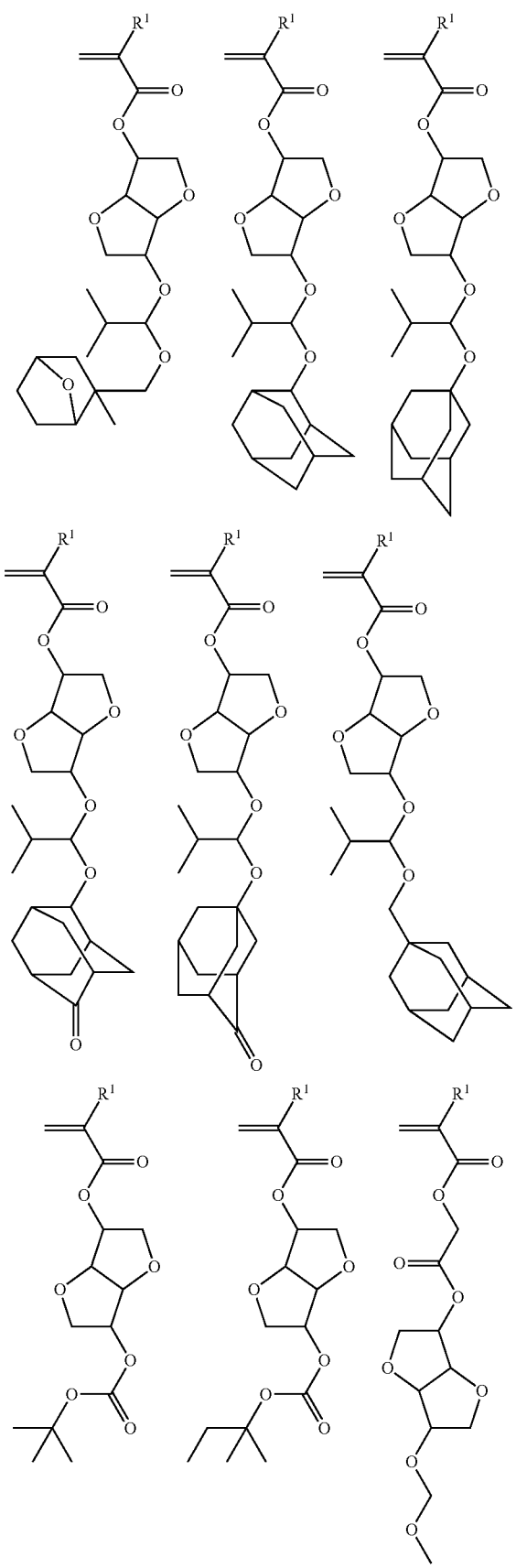
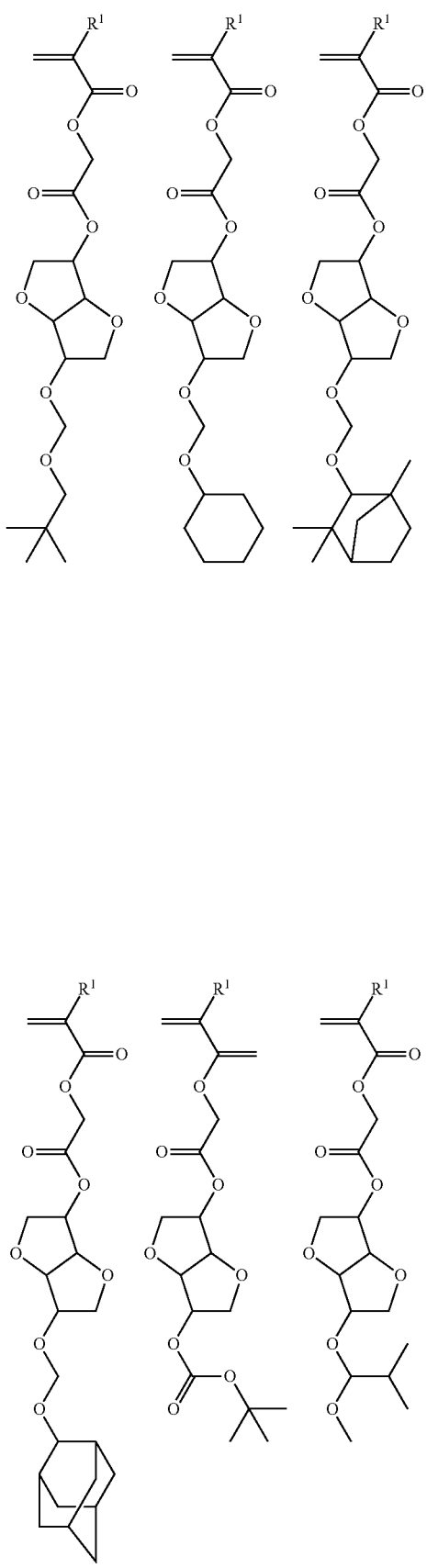

23
-continued
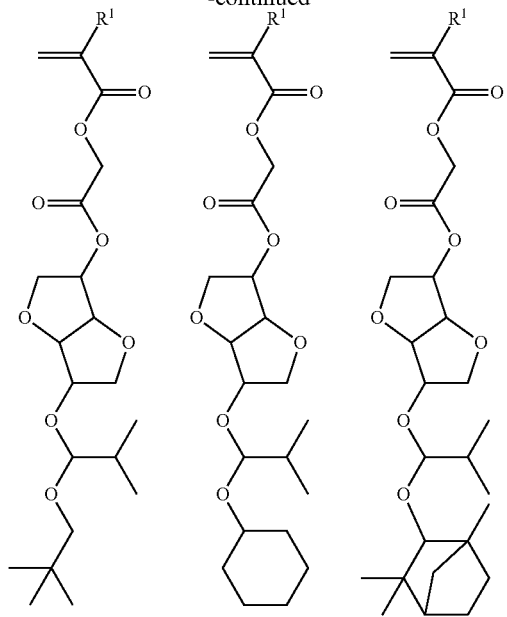
24
-continued
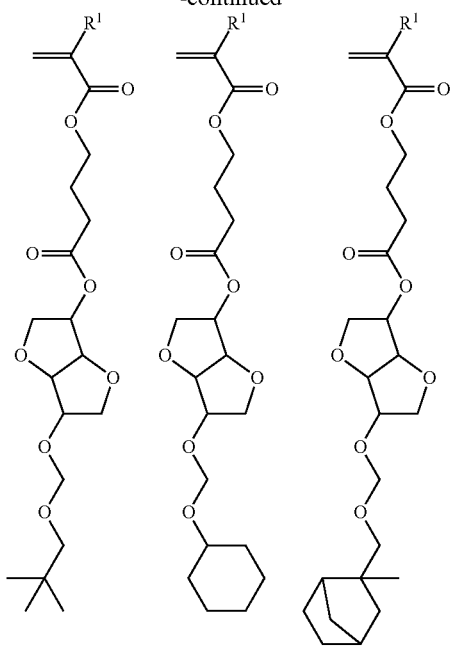
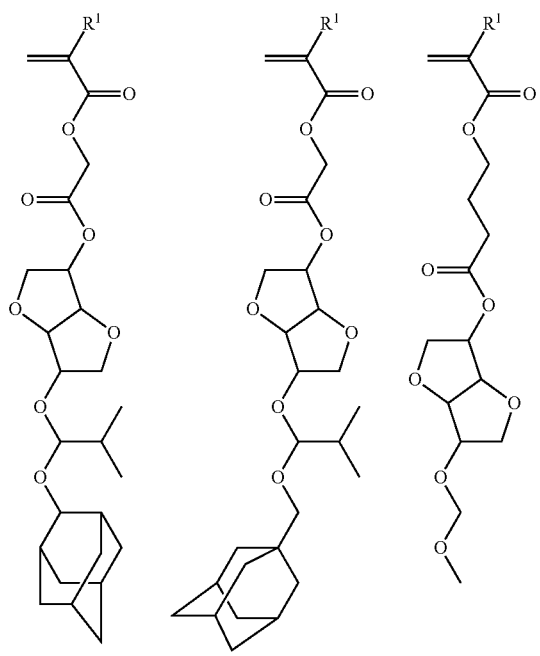
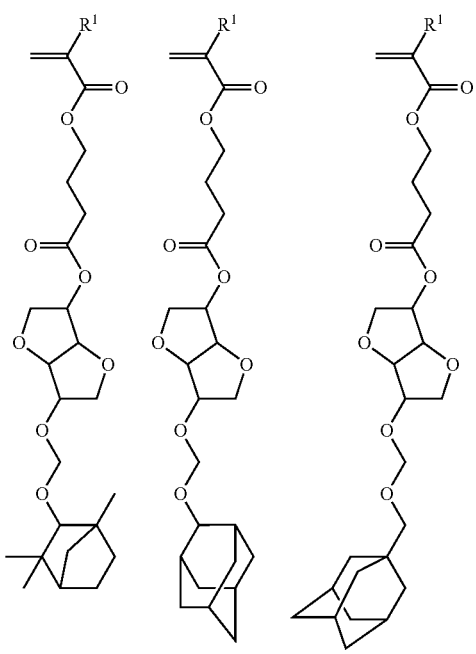

25
-continued
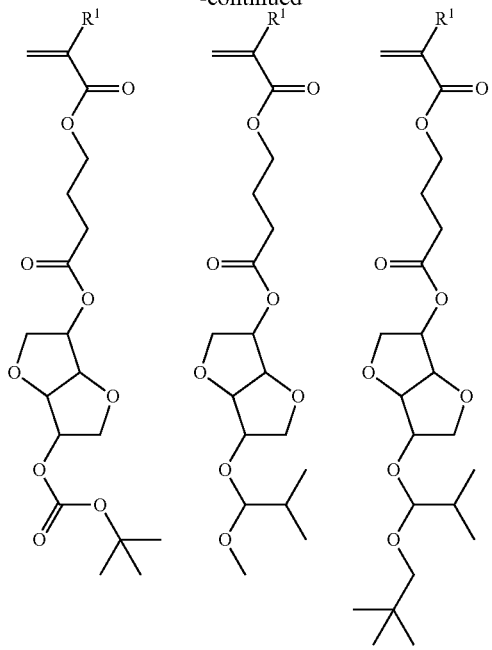
26
-continued
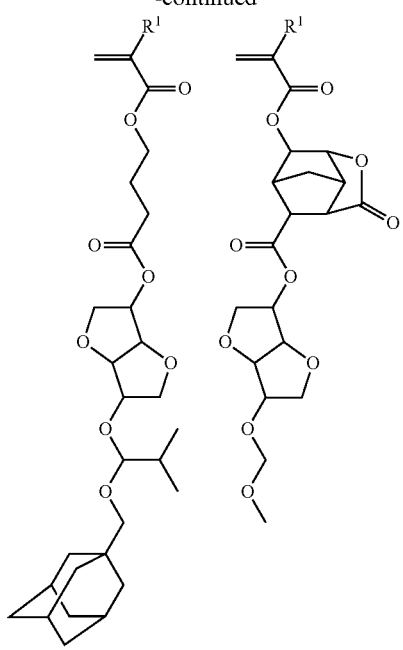
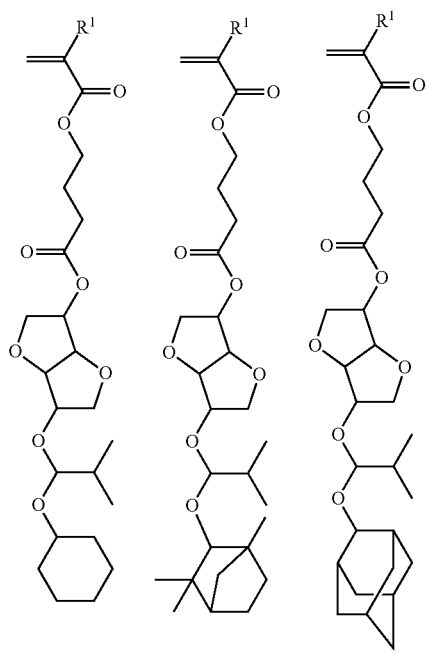
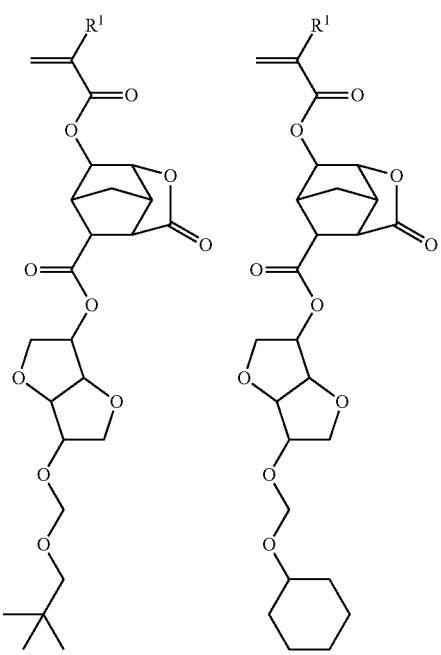

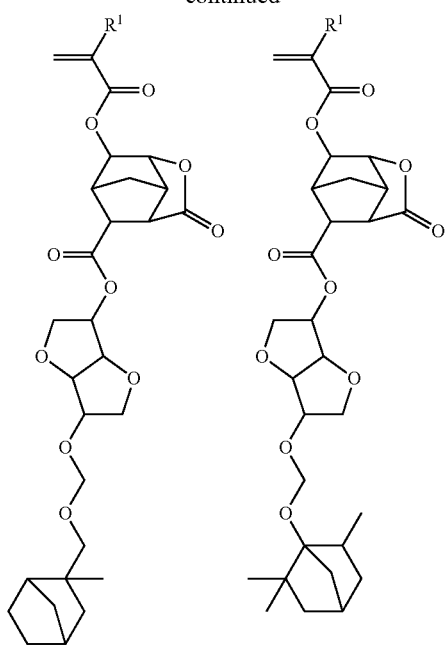
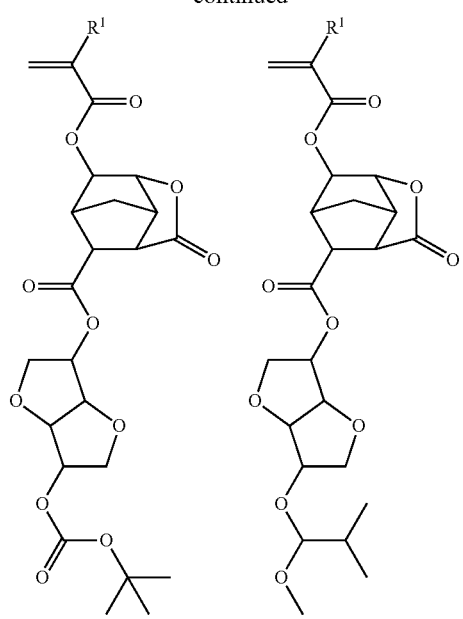
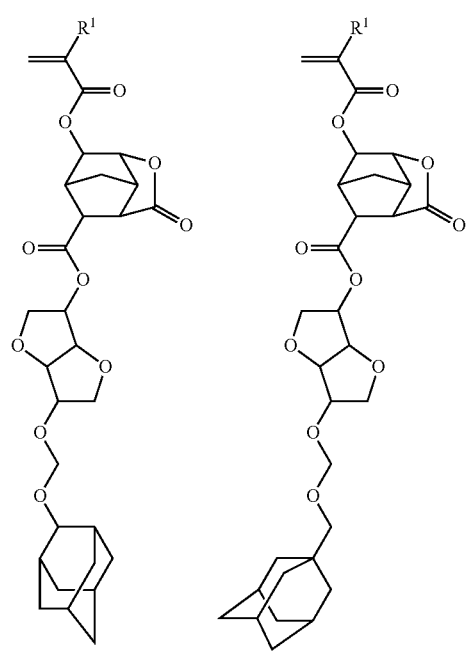
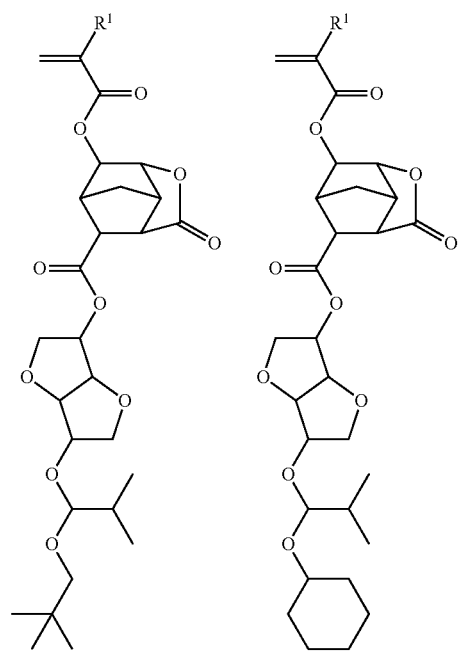

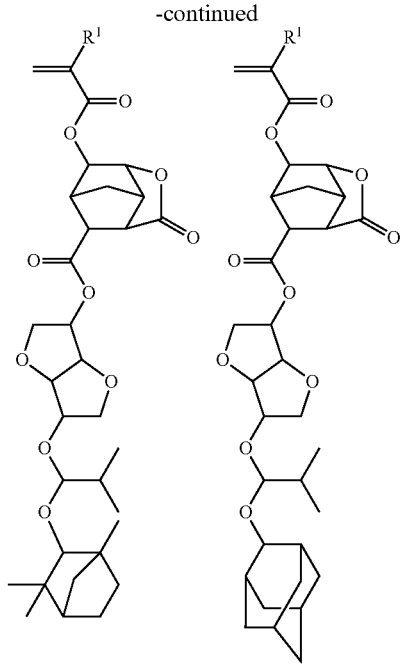
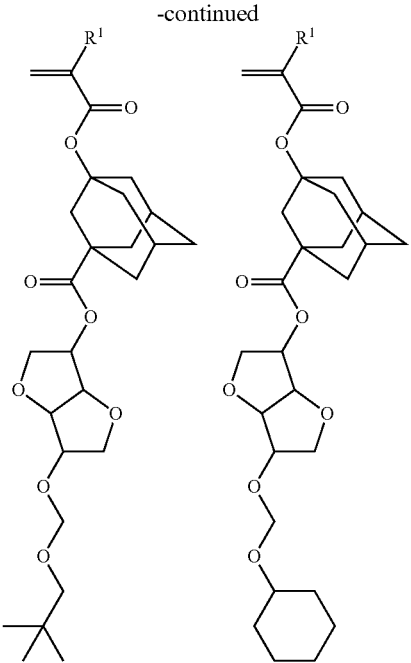
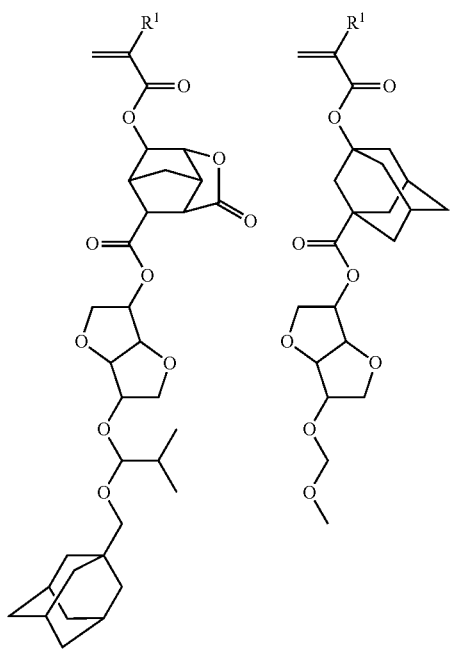
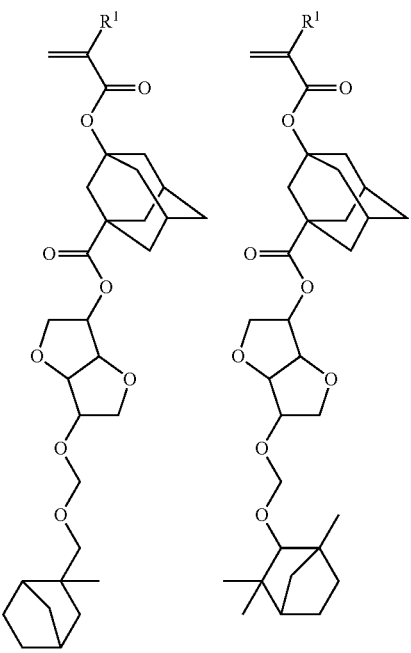

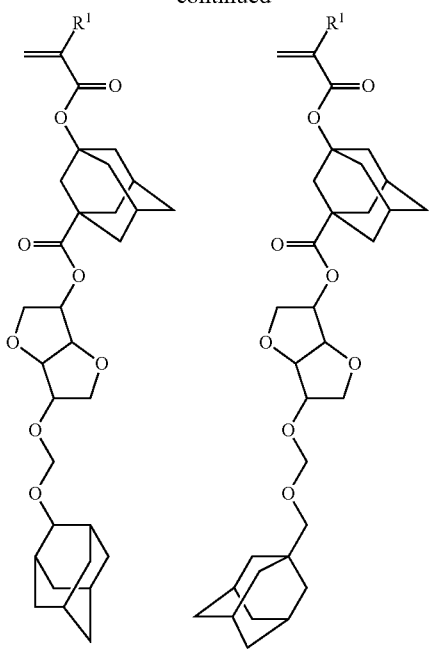
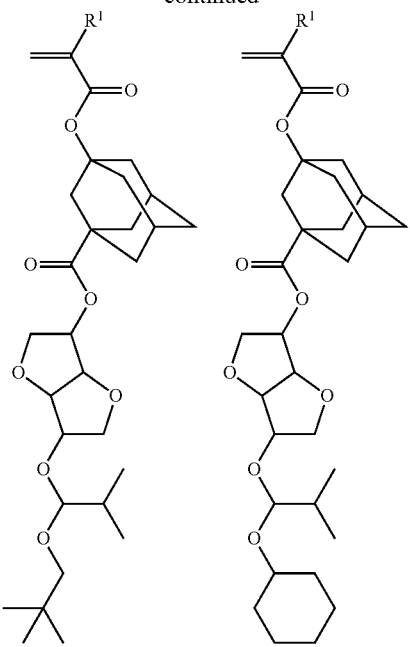
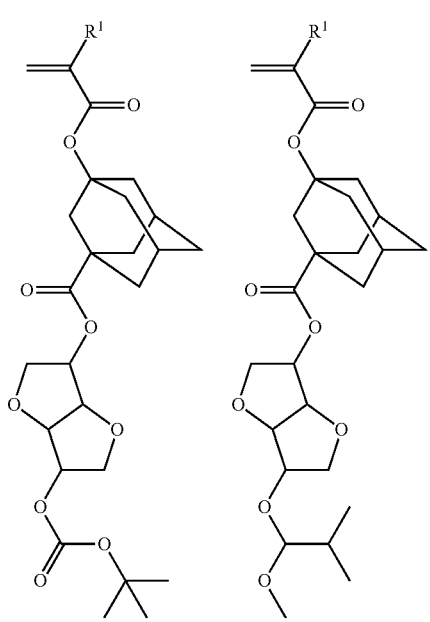
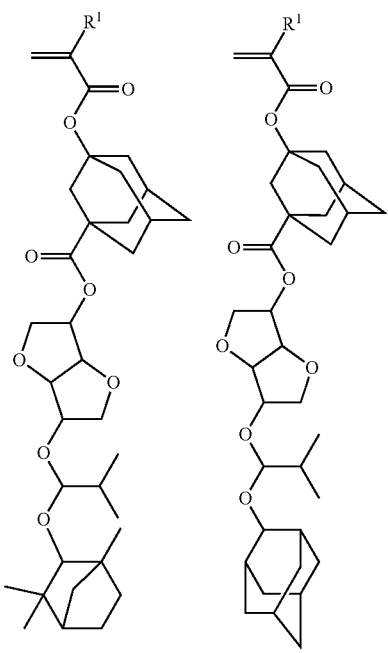

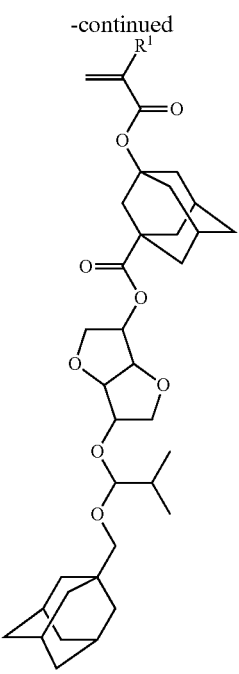

Herein R$^1$ is as defined above.

The polymerizable ester compounds of formula (1) may be produced by the process including steps i) to iv) as shown by the following reaction scheme although the process is not limited thereto.

Herein R$^1$, R$^2$, Aa and k$^1$ are as defined above; T$^3$ is halogen; and R$^5$ is halogen, hydroxyl or —OR$^6$ wherein R$^6$ is methyl, ethyl or a group of the formula (8).

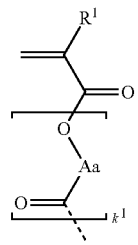

(8)

Step i) is a reaction of a diol compound (3) with a protecting agent (4) to form an alcohol compound (5).

Examples of the diol compound (3) used herein include isosorbide (1,4:3,6-dianhydro-D-sorbitol), isomannide (1,4:3,6-dianhydro-D-mannitol), and isoidide (1,4:3,6-dianhydro-L-iditol). Inter alia, isosorbide is most preferred for consistent supply and cost.

Exemplary halogen atoms of T$^3$ include chlorine, bromine and iodine. Inter alia, chlorine is most preferred for ease of handling.

The reaction of step i) runs readily by any well-known procedure. When R$^2$ in formula (5) is a group of the formula (9), that is, the protecting agent (4) has the formula (10),

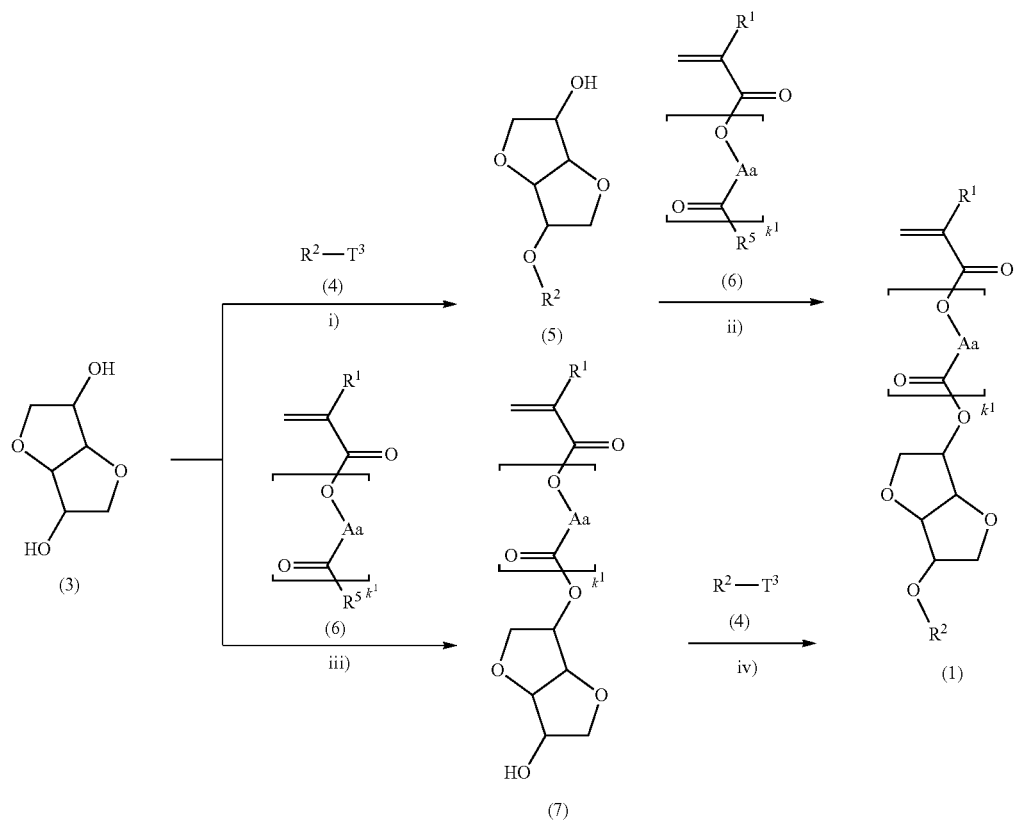

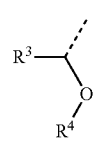

(9)

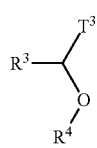

(10)

wherein $R^3$, $R^4$, and $T^3$ are as defined above, the reaction may be conducted in a solventless system or in a solvent, by sequentially or simultaneously adding diol compound (3), protecting agent (10), and a base such as triethylamine, pyridine, N,N-diisopropylethylamine or 4-dimethylaminopyridine, and optionally cooling or heating.

An amount of protecting agent (10) used is preferably 0.5 to 10 moles, more preferably 1.0 to 3.0 moles per mole of diol compound (3). With less than 0.5 mole of the protecting agent used, a large fraction of the reactant may be left unreacted, leading to a substantial drop of yield. Using more than 10 moles of the protecting agent may be uneconomical because of an increased cost of the reactant and decreased pot yields.

Suitable solvents which can be used herein include hydrocarbons such as toluene, xylene, hexane and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used alone or in admixture. To the reaction system, a phase transfer catalyst such as tetrabutylammonium hydrogen sulfate may be added. An appropriate amount of the phase transfer catalyst added is 0.0001 to 1.0 mole, and more preferably 0.001 to 0.5 mole per mole of the reactant, diol compound (3). Less than 0.0001 mole of the catalyst may exert little or no addition effect whereas more than 1.0 mole may be uneconomical because of an increased expense.

Preferably the reaction time is determined so as to attain increased yields by monitoring the reaction process by thin-layer chromatography (TLC) or gas chromatography (GC). Usually, the reaction time is about 30 minutes to about 40 hours. From the reaction mixture, the alcohol compound (5) is recovered through an ordinary aqueous workup. If necessary, the compound may be purified by a standard technique such as distillation, recrystallization or chromatography.

Step ii) is a reaction of alcohol compound (5) with an esterifying agent (6) to form the desired polymerizable ester compound (1).

The reaction may be readily conducted by a well-known technique. The preferred esterifying agent (6) is an acid chloride (corresponding to formula (6) wherein $R^5$ is chlorine) or a carboxylic anhydride (corresponding to formula (6) wherein $R^5$ is —$OR^6$ and $R^6$ has the formula (8).

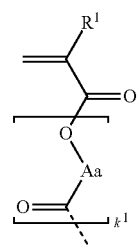

(8)

When an acid chloride is used as the esterifying agent, the reaction may be conducted in a solventless system or in a solvent such as methylene chloride, acetonitrile, toluene or hexane, by sequentially or simultaneously adding alcohol compound (5), a corresponding acid chloride such as methacrylic acid chloride or methacryloyloxyacetic acid chloride, and a base such as triethylamine, pyridine or 4-dimethylaminopyridine, and optionally cooling or heating. When a carboxylic anhydride is used as the esterifying agent, the reaction may be conducted in a solventless system or in a solvent such as methylene chloride, acetonitrile, toluene or hexane, by sequentially or simultaneously adding alcohol compound (5), a corresponding carboxylic anhydride such as methacrylic anhydride or methacryloyloxyacetic anhydride, and a base such as triethylamine, pyridine or 4-dimethylaminopyridine, and optionally heating or cooling.

Step iii) is a reaction of alcohol compound (3) with an esterifying agent (6) to form an ester compound (7).

The reaction may be readily conducted by a well-known technique. The preferred esterifying agent (6) is an acid chloride (corresponding to formula (6) wherein $R^5$ is chlorine) or a carboxylic acid (corresponding to formula (6) wherein $R^5$ is hydroxyl). When an acid chloride is used as the esterifying agent, the reaction may be conducted in a solventless system or in a solvent such as methylene chloride, toluene, hexane, diethyl ether, tetrahydrofuran or acetonitrile, by sequentially or simultaneously adding alcohol compound (3), a corresponding acid chloride such as methacrylic acid chloride or methacryloyloxyacetic acid chloride, and a base such as triethylamine, pyridine or 4-dimethylaminopyridine, and optionally cooling or heating. When a carboxylic acid is used as the esterifying agent, the reaction may be conducted in a solvent such as toluene or hexane, by heating alcohol compound (3) and a corresponding carboxylic acid such as methacrylic acid or methacryloyloxyacetic acid, in the presence of an acid catalyst, and optionally removing the water formed during reaction from the system. Examples of the acid catalyst used herein include mineral acids such as hydrochloric acid, sulfuric acid, nitric acid and perchloric acid, and organic acids such as p-toluenesulfonic acid and benzenesulfonic acid.

Step iv) is a reaction of ester compound (7) with a protecting agent (4) to form the desired polymerizable ester compound (1).

Suitable halogen atoms represented by $T^3$ include chlorine, bromine and iodine. Inter alia, chlorine is most preferred for ease of handling.

The reaction of step iv) runs readily by any well-known procedure. When $R^2$ in formula (1) is a group of the formula (9), that is, the protecting agent (4) has the formula (10),

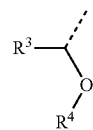

(9)

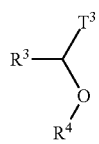

(10)

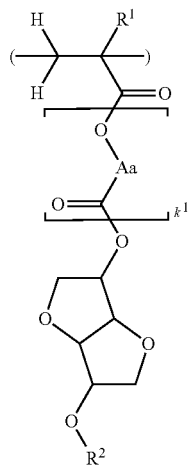

(2a)

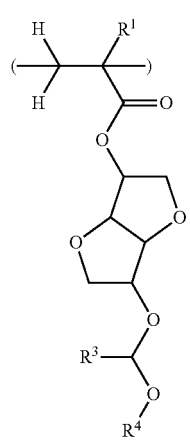

(2b)

wherein R³, R⁴, and T³ are as defined above, the reaction may be conducted in a solventless system or in a solvent, by sequentially or simultaneously adding ester compound (7), protecting agent (10), and a base such as triethylamine, pyridine, N,N-diisopropylethylamine or 4-dimethylaminopyridine, and optionally cooling or heating.

An amount of protecting agent (10) used is preferably 0.5 to 10 moles, more preferably 1.0 to 3.0 moles per mole of ester compound (7). With less than 0.5 mole of the protecting agent used, a large fraction of the reactant may be left unreacted, leading to a substantial drop of yield. Using more than 10 moles of the protecting agent may be uneconomical because of an increased cost of the reactant and decreased pot yields.

Suitable solvents which can be used herein include hydrocarbons such as toluene, xylene, hexane and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide, and dimethyl sulfoxide; and water, which may be used alone or in admixture. To the reaction system, a phase transfer catalyst such as tetrabutylammonium hydrogen sulfate may be added. An appropriate amount of the phase transfer catalyst added is 0.0001 to 1.0 mole, and more preferably 0.001 to 0.5 mole per mole of the reactant, ester compound (7). Less than 0.0001 mole of the catalyst may exert little or no addition effect whereas more than 1.0 mole may be uneconomical because of an increased expense.

Preferably the reaction time is determined so as to attain increased yields by monitoring the reaction process by TLC or GC. Usually, the reaction time is about 30 minutes to about 40 hours. From the reaction mixture, the ester compound (1) is recovered through an ordinary aqueous workup. If necessary, the compound may be purified by a standard technique such as distillation, recrystallization or chromatography.

Polymer

A second embodiment of the invention is a polymer comprising recurring units derived from the polymerizable ester compound having formula (1) or (2).

Specifically the polymer is defined as comprising recurring units having the general formula (2a) or (2b).

Herein $R^1$ is hydrogen, fluorine, methyl or trifluoromethyl, $R^2$ is an acid labile group, $R^3$ is hydrogen or a $C_1$-$C_{15}$ straight, branched or cyclic, monovalent hydrocarbon group, $R^4$ is a $C_1$-$C_{15}$ straight, branched or cyclic, monovalent hydrocarbon group in which a constituent —$CH_2$— may be substituted by —O— or —C(=O)—, Aa is a $C_1$-$C_{10}$, preferably $C_1$-$C_6$ straight, branched or cyclic, divalent hydrocarbon group in which a constituent —$CH_2$— may be substituted by —O— or —C(=O)—, and $k^1$ is 0 or 1.

In addition to the recurring units having formula (2a) or (2b), the polymers of the invention may further comprise recurring units of at least one type selected from the general formulas (2A) to (2D).

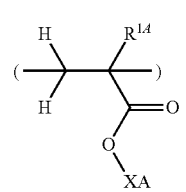

(2A)

(2B)

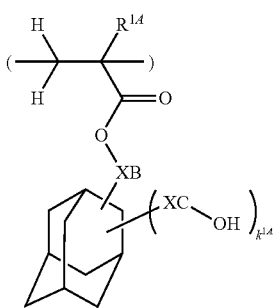

(2C)

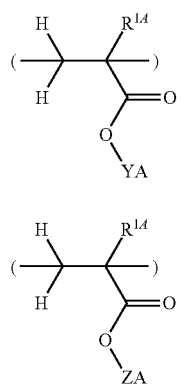

(2D)

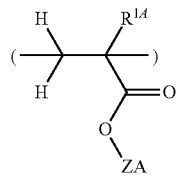

Herein $R^{14}$ is hydrogen, fluorine, methyl or trifluoromethyl; XA is an acid labile group; XB and XC are each independently a single bond, or a $C_1$-$C_4$ straight or branched divalent hydrocarbon group; YA is a substituent group having a lactone or sultone structure; ZA is hydrogen, a $C_1$-$C_{15}$ fluoroalkyl group, or a $C_1$-$C_{15}$ fluoroalcohol-containing substituent group; and $k^{14}$ is an integer of 1 to 3.

Under the action of acid, a polymer comprising recurring units of formula (2A) is decomposed to generate carboxylic acid, turning to be an alkali soluble polymer. The acid labile group XA may be selected from a variety of such groups. Examples of the acid labile group are groups of the following general formulas (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

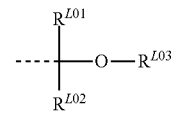

(L2)

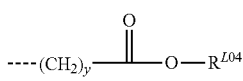

(L3)

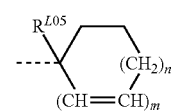

(L4)

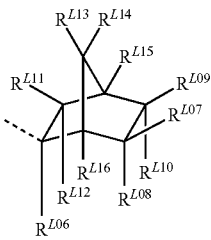

In these formulas, the broken line denotes a valence bond. $R^{L01}$ and $R^{L02}$ are hydrogen or straight, branched or cyclic alkyl groups of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or the like. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is a substituted or unsubstituted, straight, branched or cyclic alkyl group of 1 to 10 carbon atoms or a substituted or unsubstituted aryl group of 6 to 20 carbon atoms. $R^{L06}$ is a substituted or unsubstituted, straight, branched or cyclic alkyl group of 1 to 10 carbon atoms or a substituted or unsubstituted aryl group of 6 to 20 carbon atoms. $R^{L07}$ to $R^{L16}$ independently represent hydrogen or a substituted or unsubstituted monovalent hydrocarbon group of 1 to 15 carbon atoms. The subscript y is an integer of 0 to 6, m is 0 or 1, n is an integer of 0 to 3, and 2 m+n is equal to 2 or 3.

In formula (L1), exemplary alkyl groups of $R^{L01}$ and $R^{L02}$ include methyl, ethyl, n-propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or the like. Suitable straight, branched or cyclic alkyl groups are as exemplified for $R^{L01}$ and $R^{L02}$. Illustrative examples of the substituted alkyl groups are shown below.

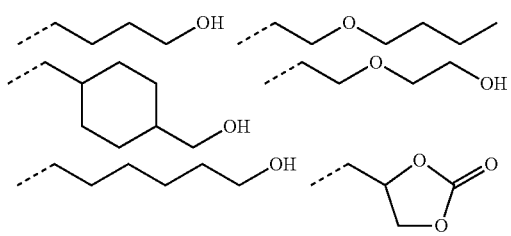

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), exemplary tertiary alkyl groups of $R^{L04}$ are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), the optionally substituted straight, branched or cyclic $C_1$-$C_{10}$ alkyl groups of $R^{L05}$ include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which one or more hydrogen atom is substituted by hydroxyl, alkoxy, carboxy, alkoxycarbonyl, oxo, amino, alkylamino, cyano, mercapto, alkylthio, sulfo or other radicals or in which one or more methylene moiety is substituted by oxygen or sulfur atom. Examples of the optionally substituted $C_6$-$C_{20}$ aryl groups include phenyl, methylphenyl, naphthyl, anthryl, phenanthryl, and pyrenyl.

In formula (L4), examples of the optionally substituted, straight, branched or cyclic $C_1$-$C_{10}$ alkyl group or optionally substituted $C_6$-$C_{20}$ aryl group of $R^{L06}$ are the same as exemplified for $R^{L05}$.

Examples of the monovalent $C_1$-$C_{15}$ hydrocarbon groups of $R^{L07}$ to $R^{L16}$ include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other radicals.

Alternatively, $R^{L07}$ to $R^{L16}$ taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group, typically alkylene, when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

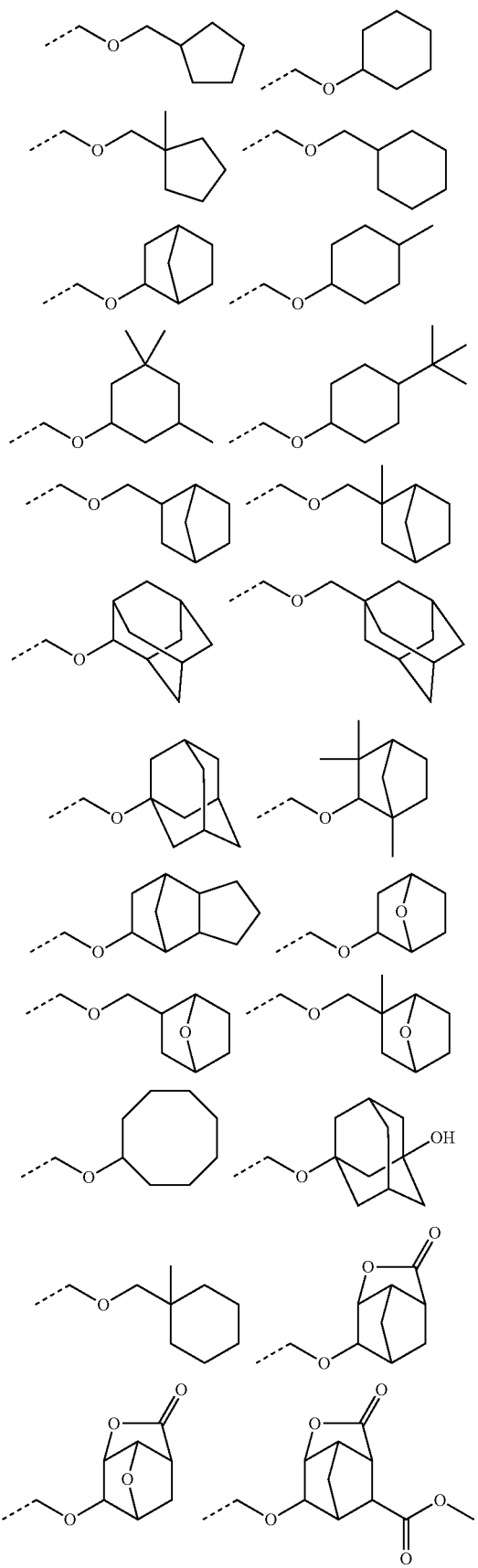

-continued

-continued

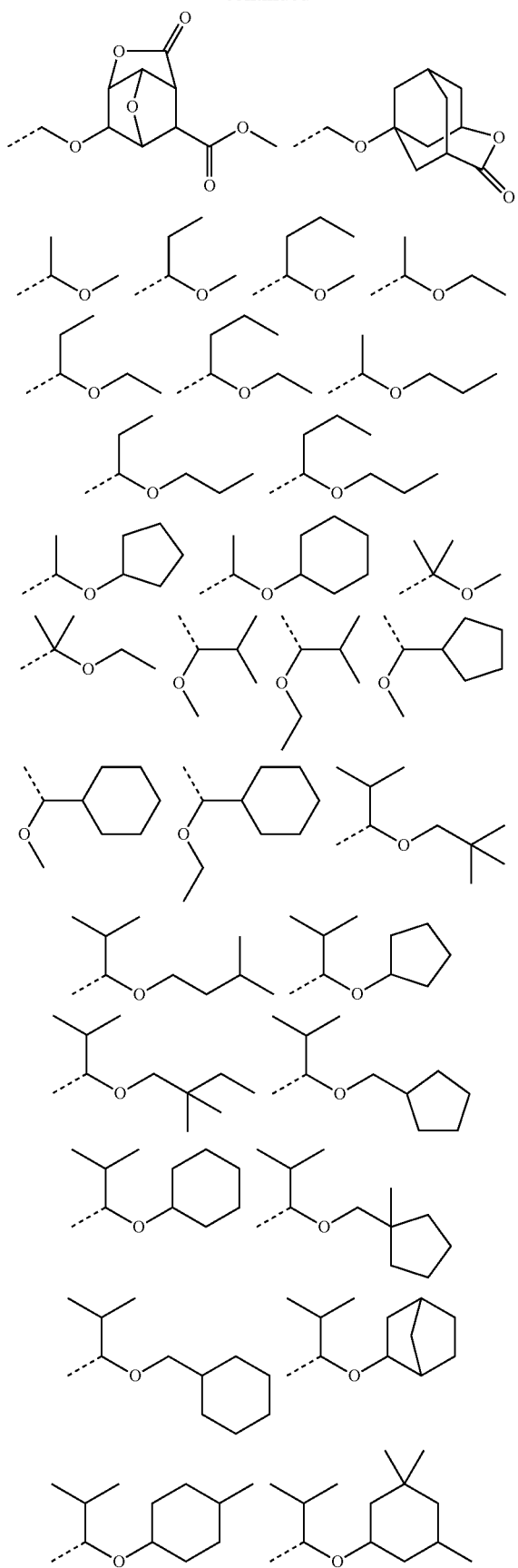
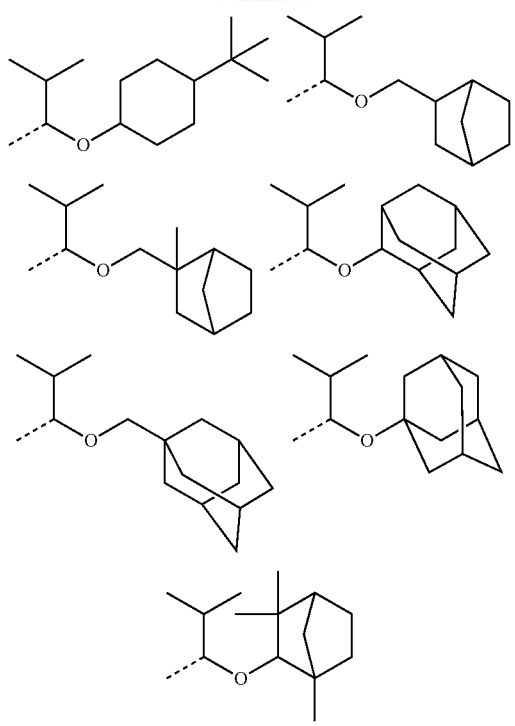

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

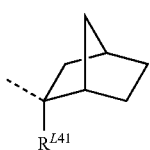

(L4-1)

(L4-2)

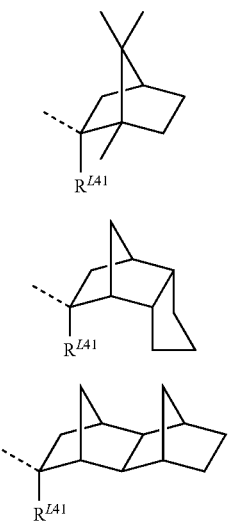

(L4-3)

(L4-4)

(L4-4-2)

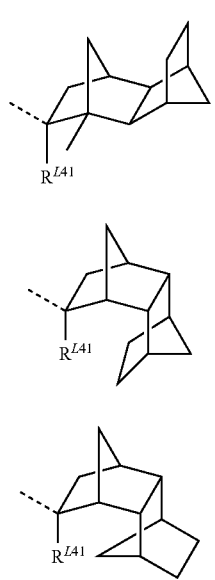

(L4-4-3)

(L4-4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulas (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2) wherein $R^{L41}$ is as defined above.

(L4-3-1)

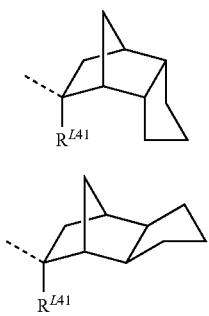

(L4-3-2)

Similarly, the general formula (L4-4) represents one or a mixture of two or more selected from groups having the following general formulas (L4-4-1) to (L4-4-4) wherein $R^{L41}$ is as defined above.

(L4-4-1)

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50% is preferred, with an exo proportion of at least 80% being more preferred.

(L4-1-endo)

(L4-2-endo)

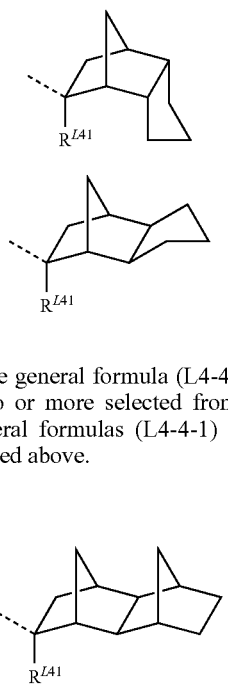

(L4-3-endo)

(L4-4-endo)

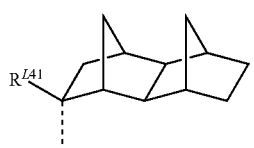

Herein $R^{L41}$ is as defined above.

Illustrative examples of the acid labile group of formula (L4) are given below.

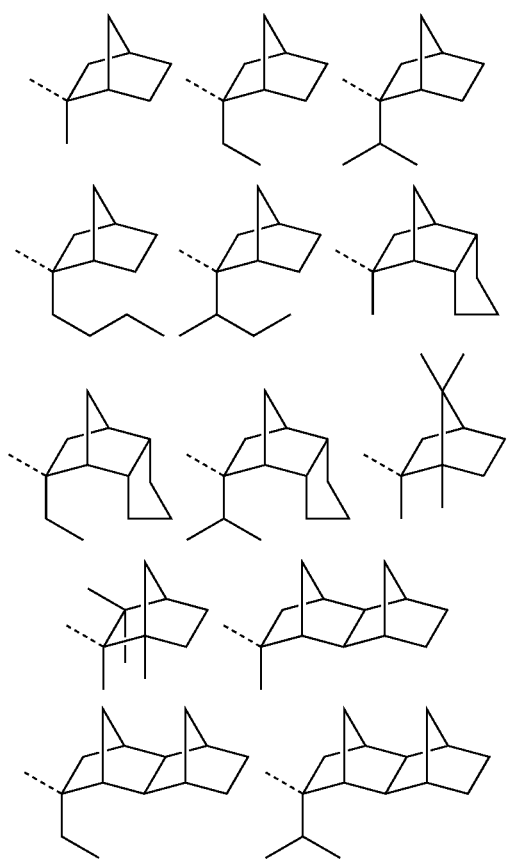

Examples of the $C_4$-$C_{20}$ tertiary alkyl groups, trialkylsilyl groups in which each alkyl moiety has 1 to 6 carbon atoms, and $C_4$-$C_{20}$ oxoalkyl groups are as exemplified for $R^{L04}$.

Illustrative examples of the recurring units of formula (2A) are given below, but not limited thereto.

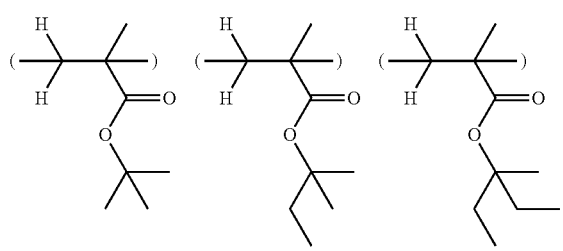

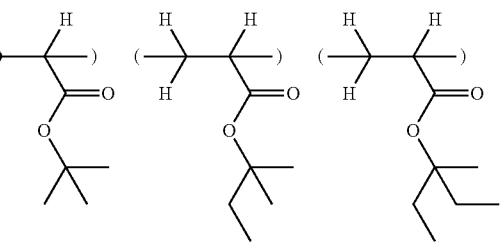

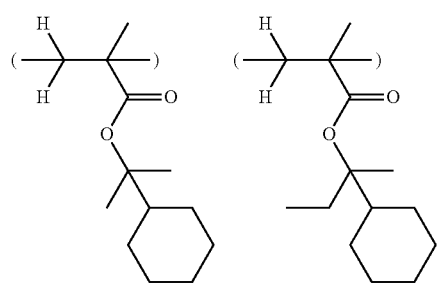

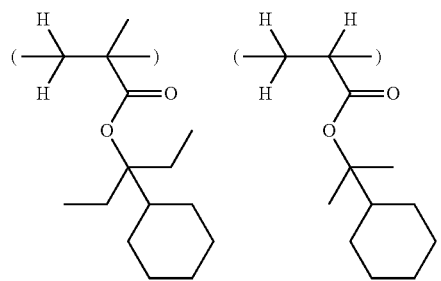

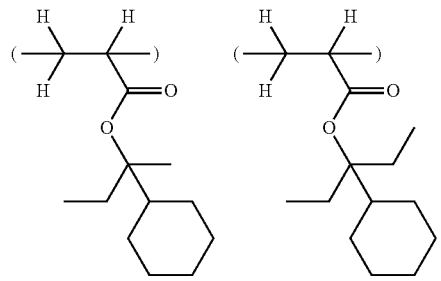

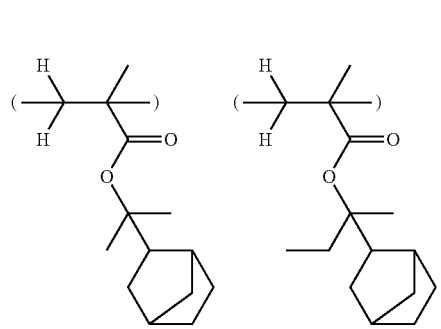

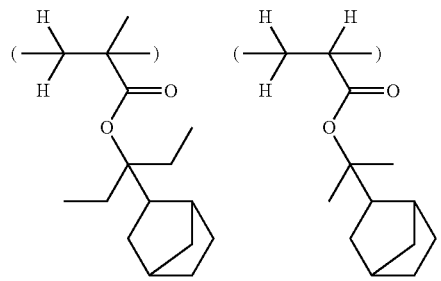

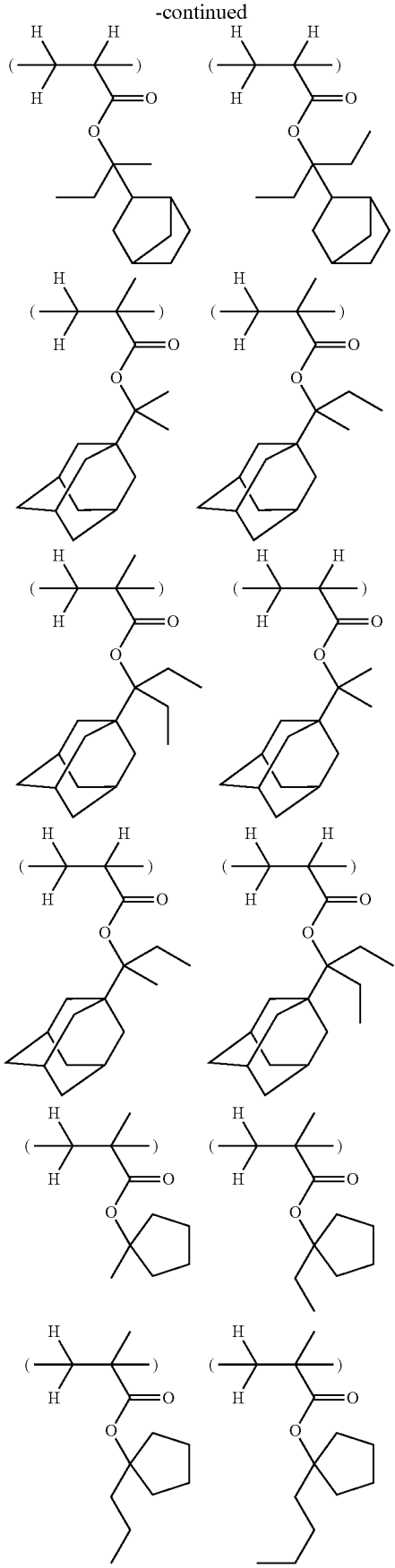
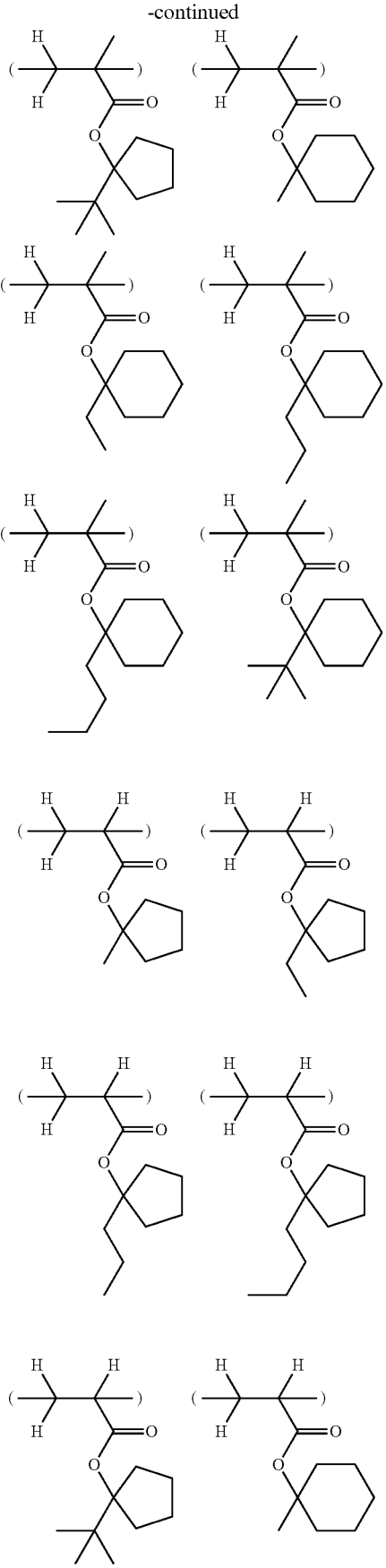

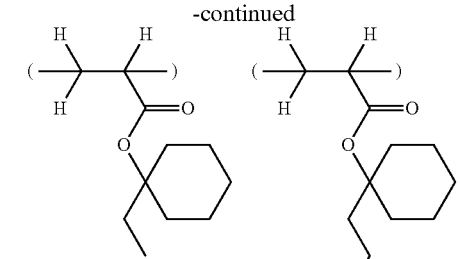
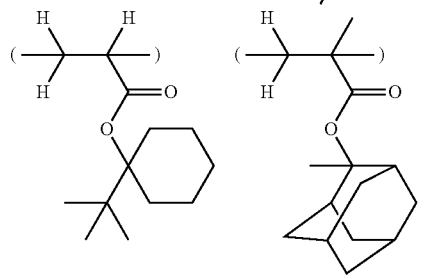
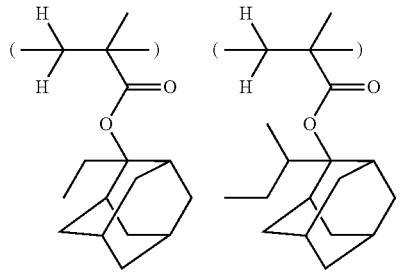
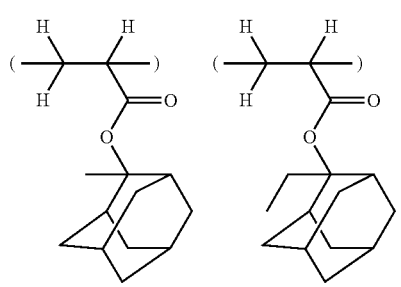
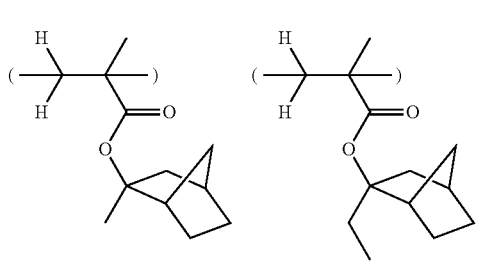
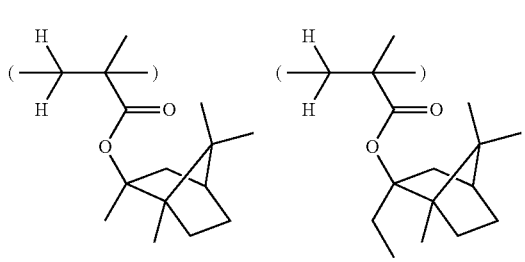
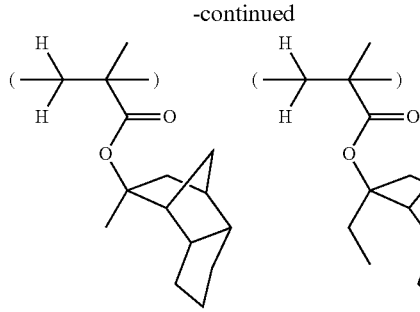
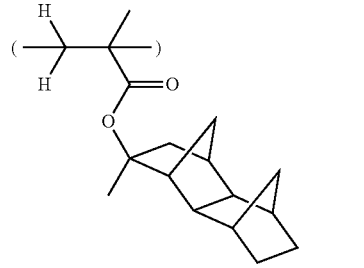
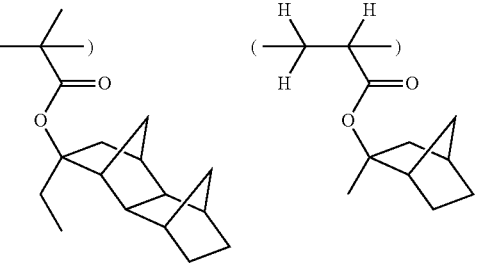
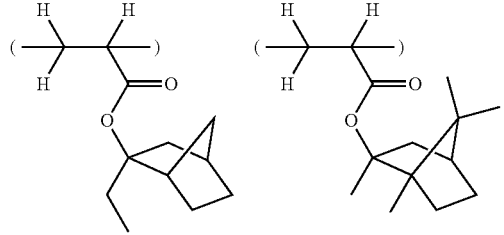
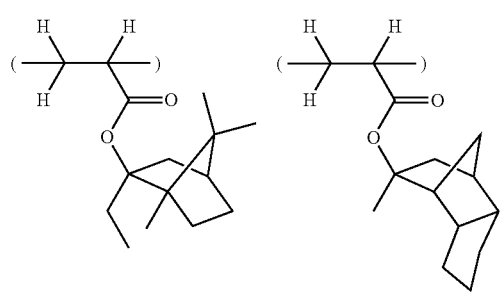
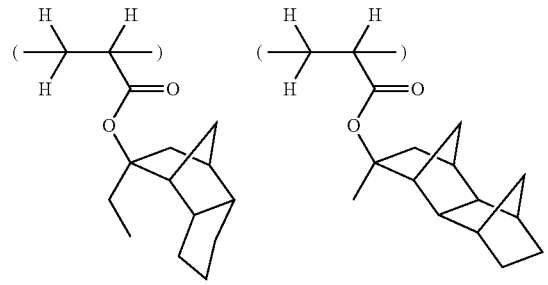

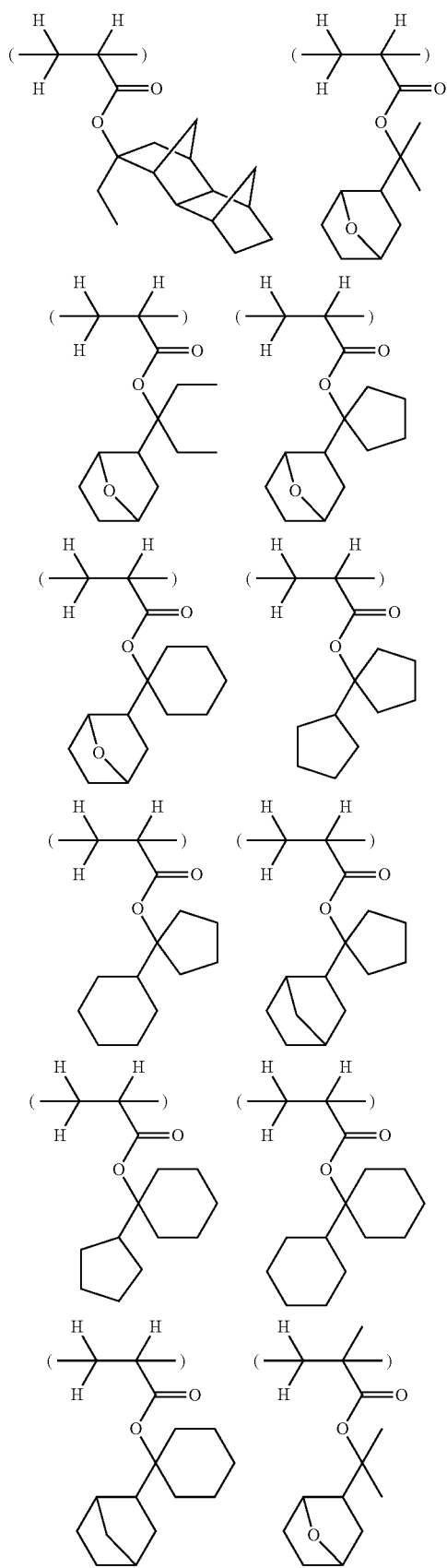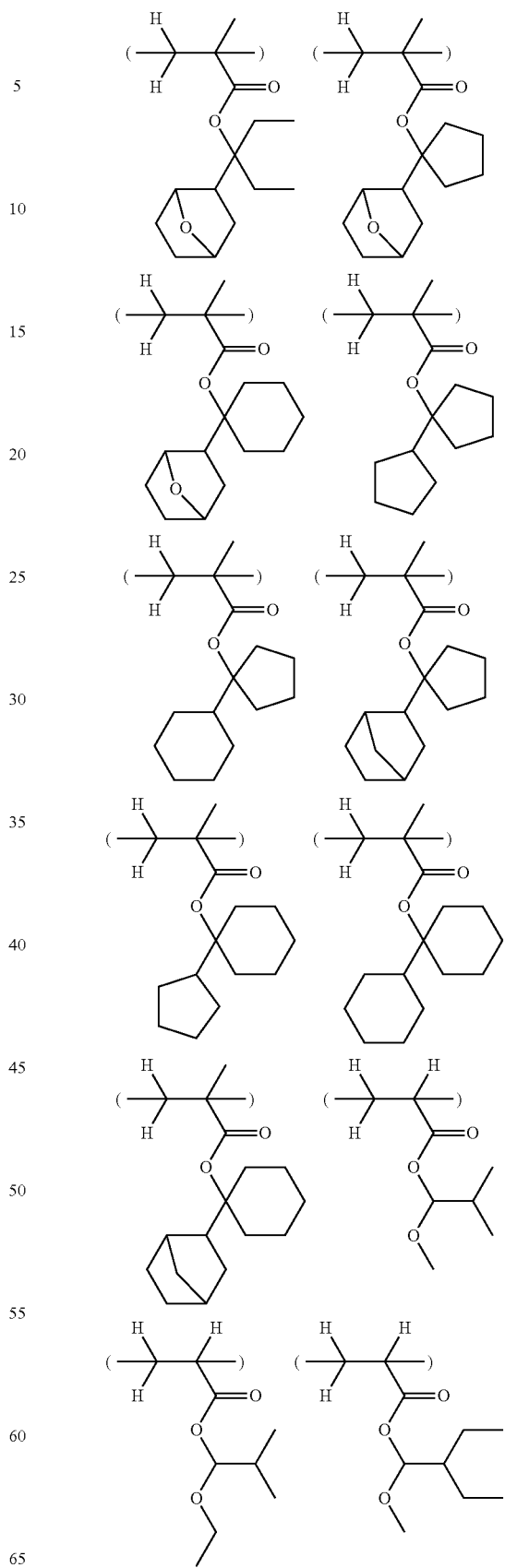

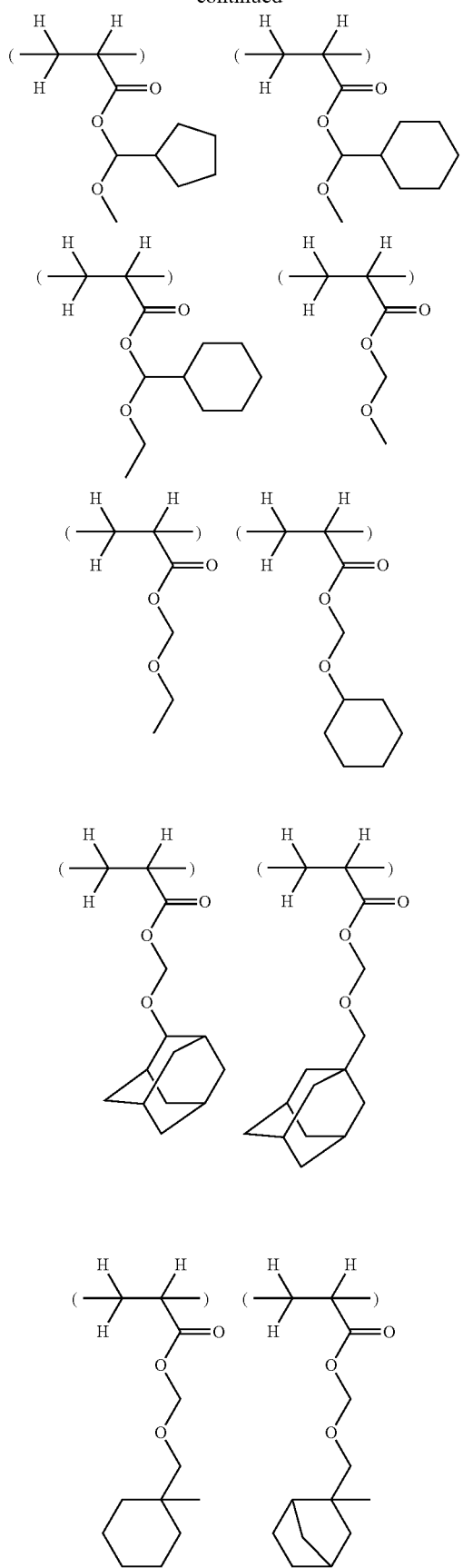
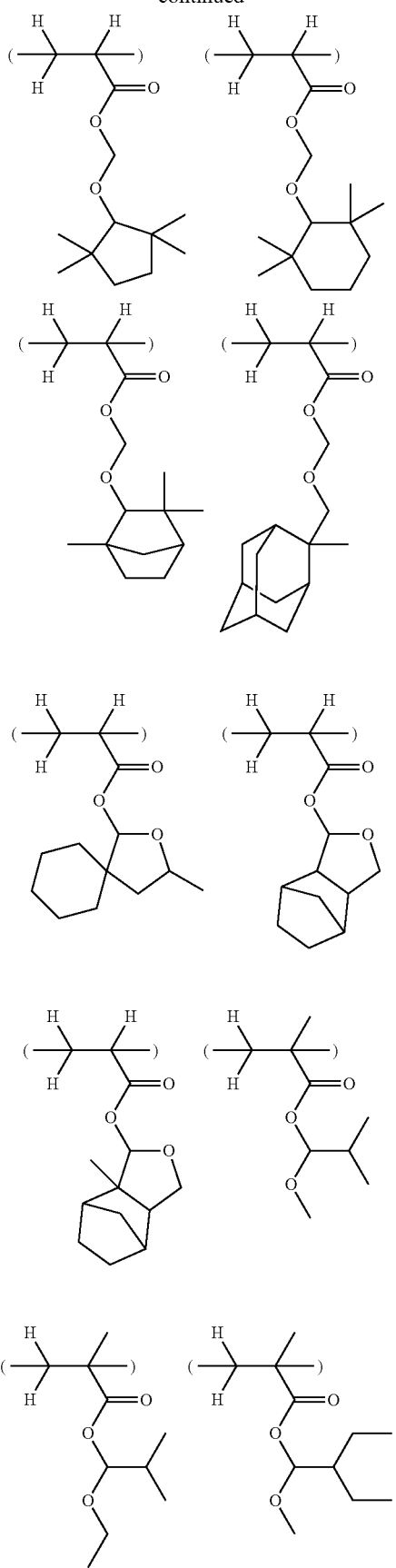

-continued
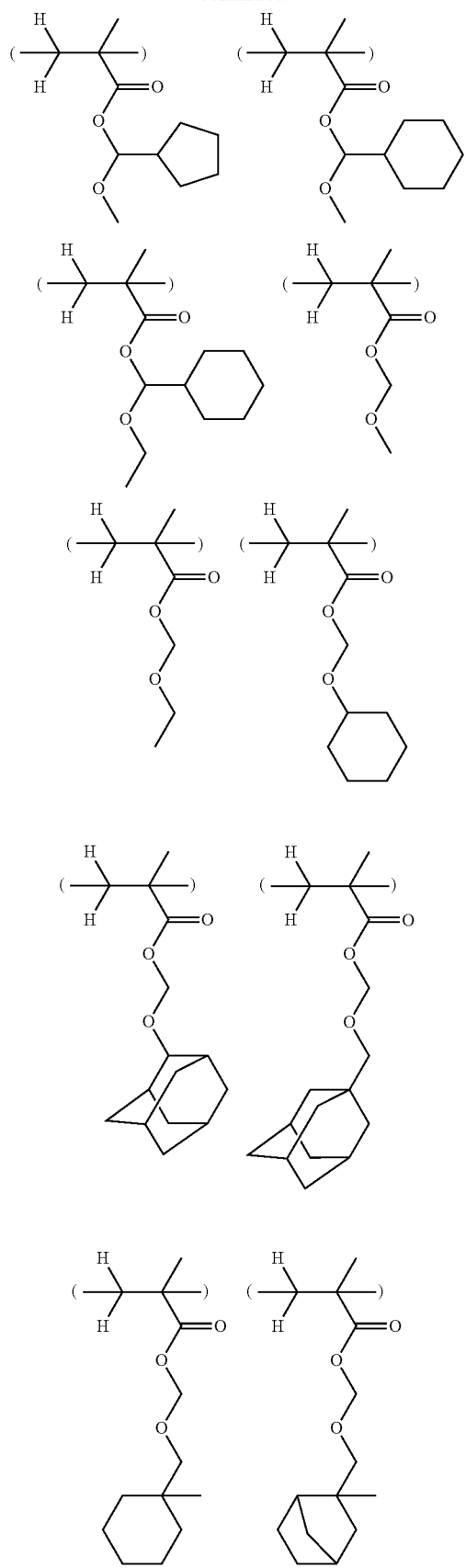
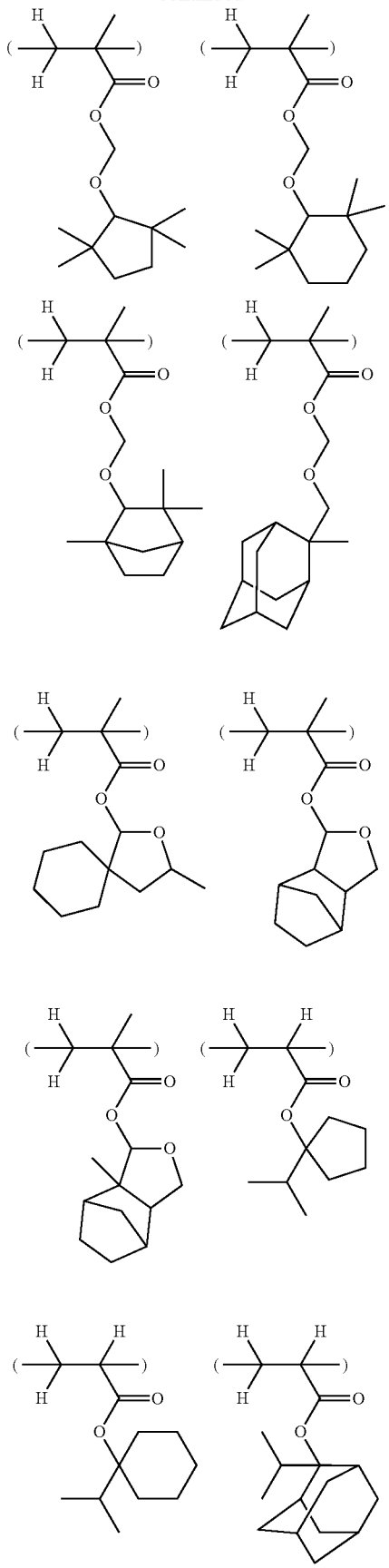

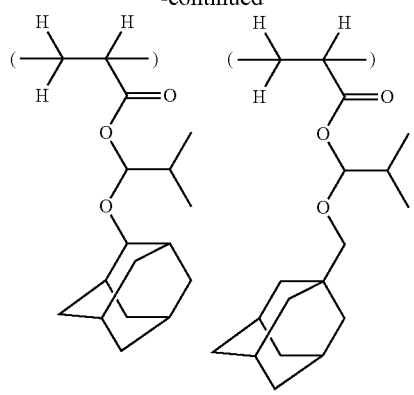
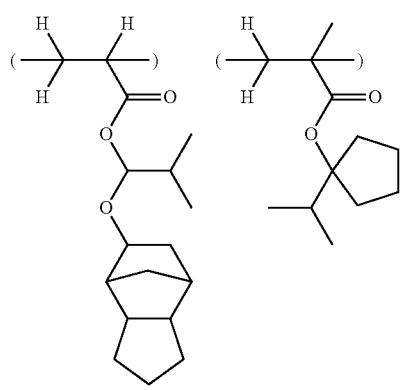
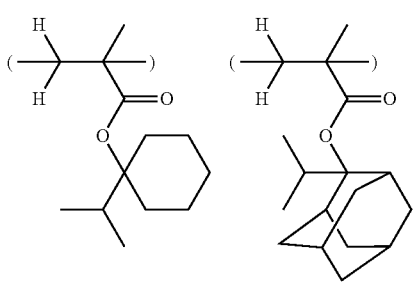
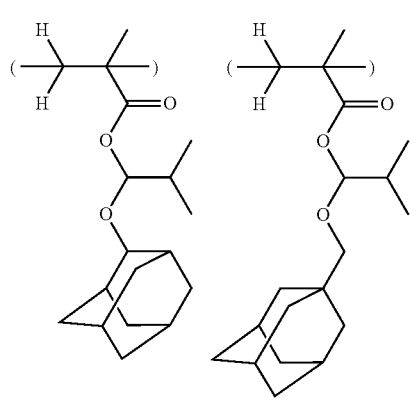
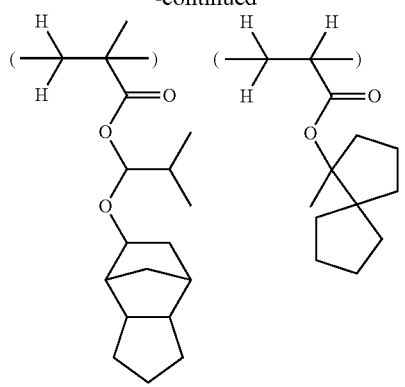
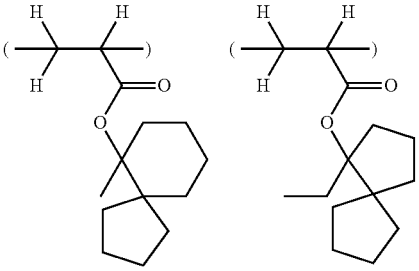
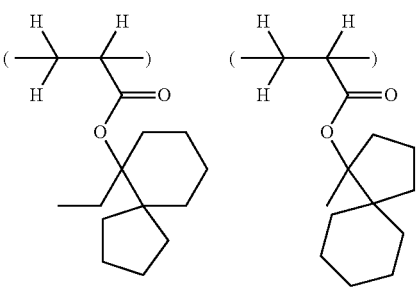
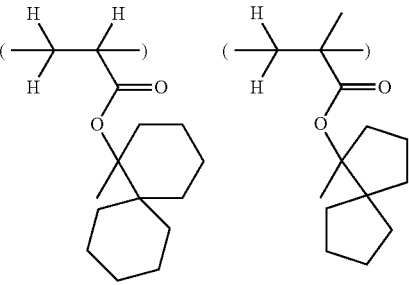
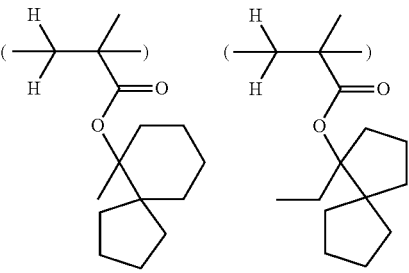

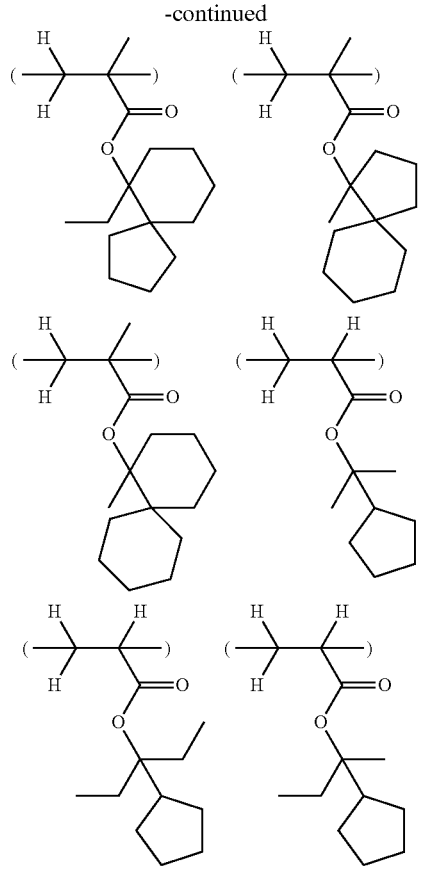
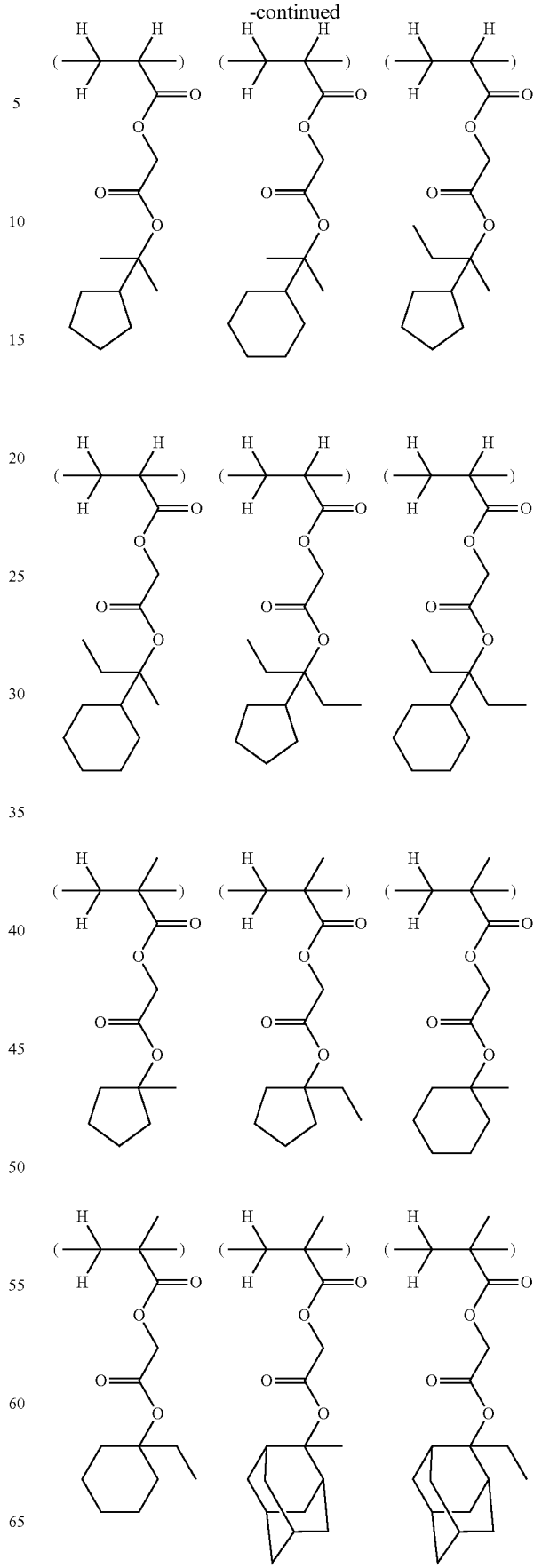

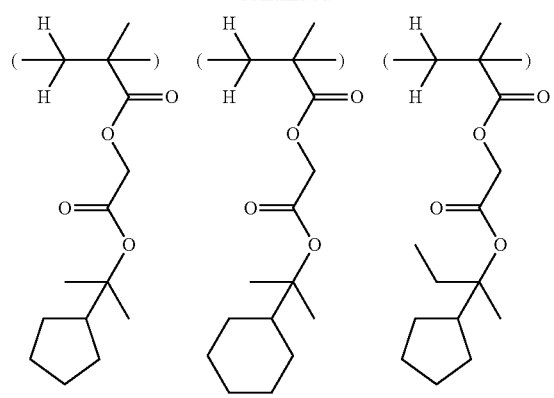
Illustrative examples of the recurring units of formula (2B) are given below, but not limited thereto.
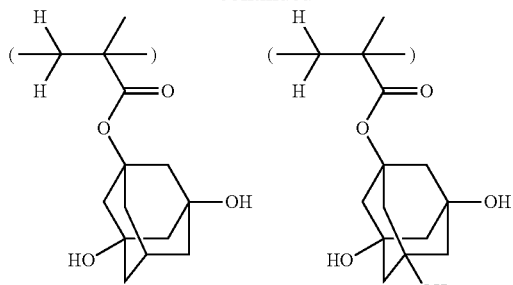
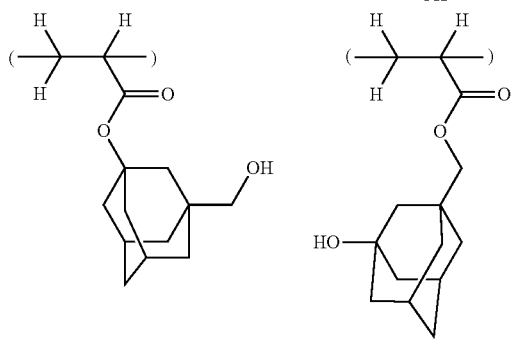
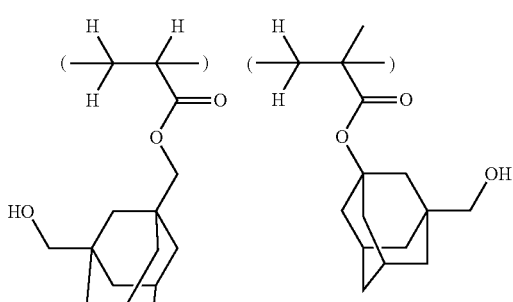
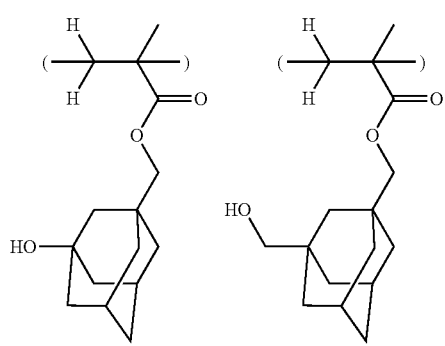
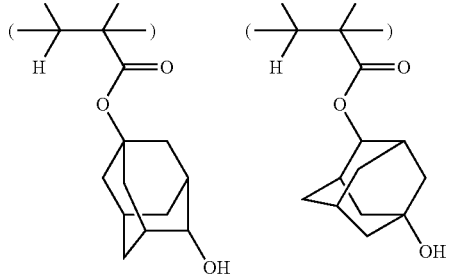

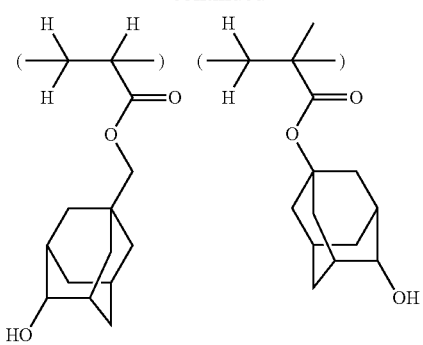
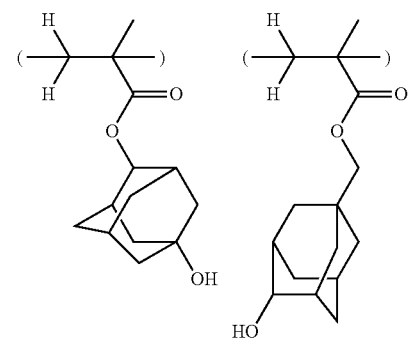
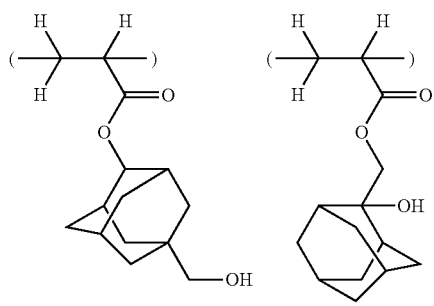
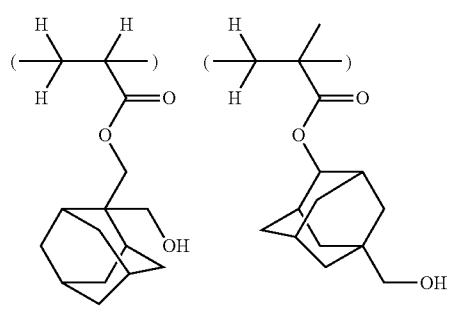
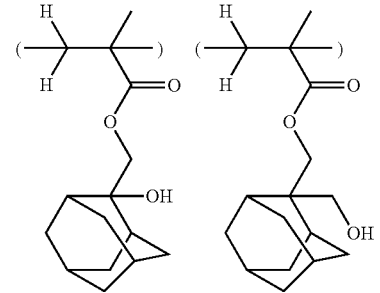
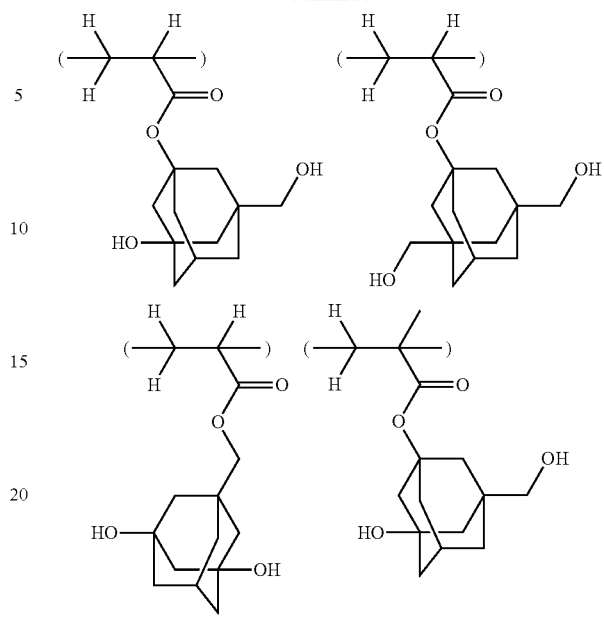
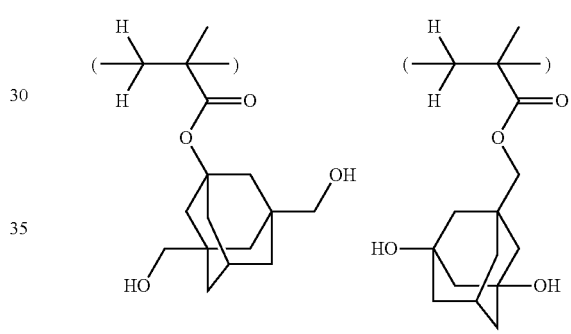
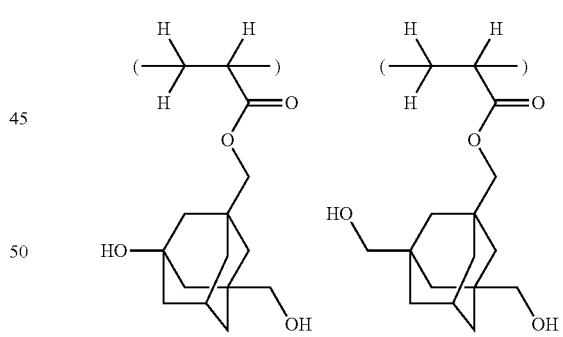
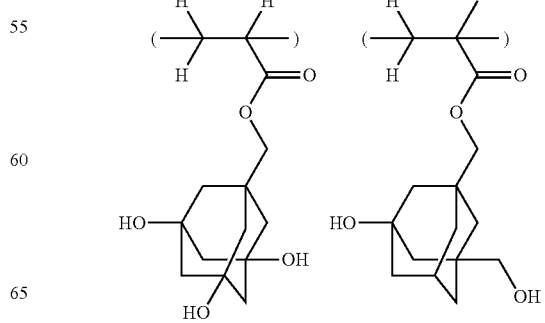

-continued
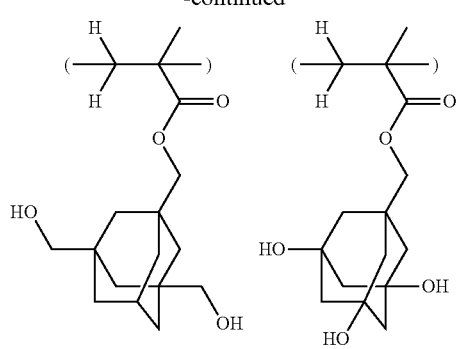
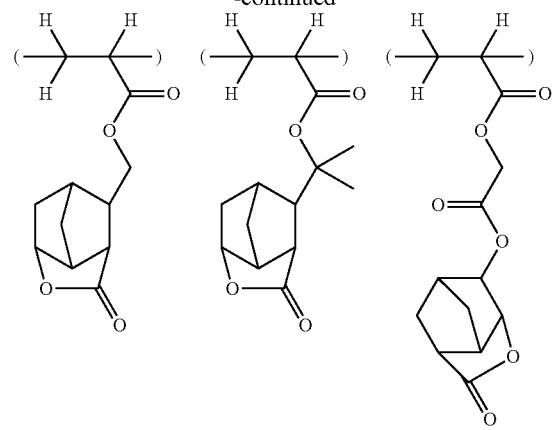
Illustrative examples of the recurring units of formula (2C) are given below, but not limited thereto.
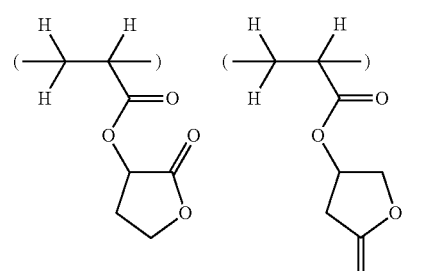
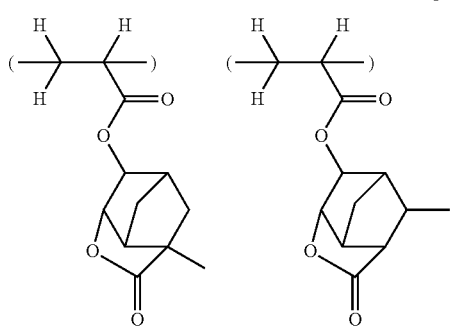
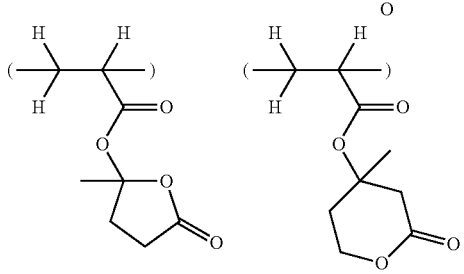
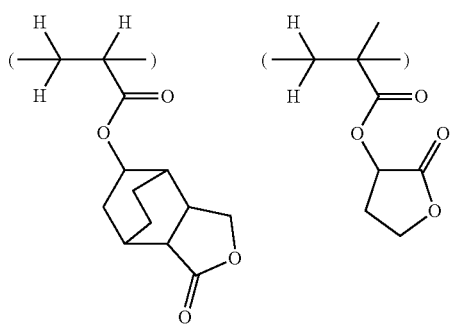
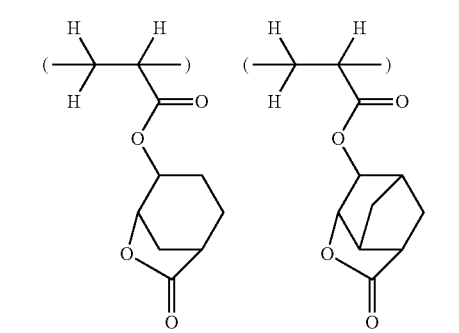
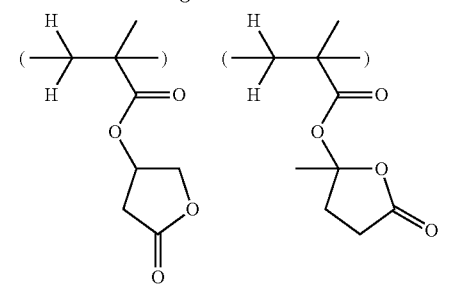
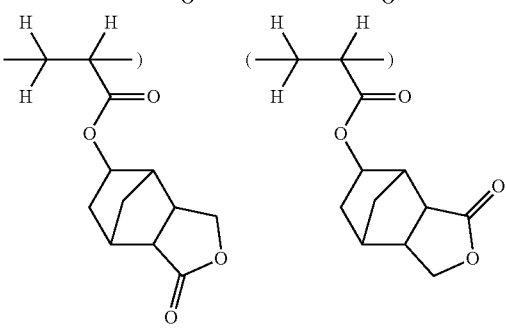
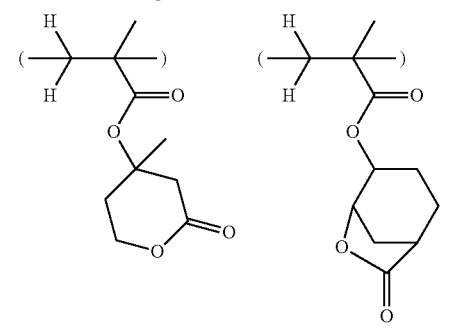

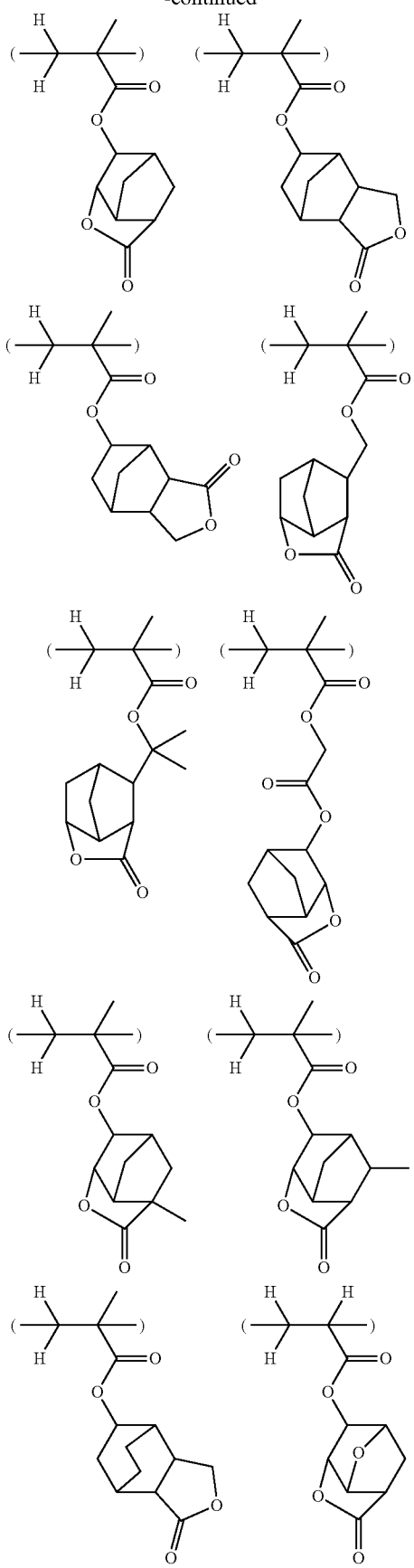
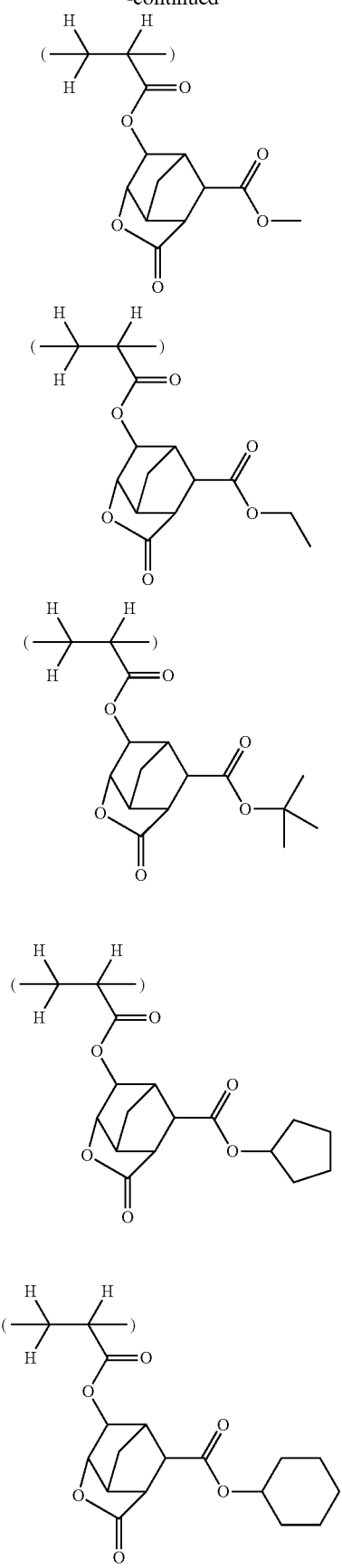

-continued
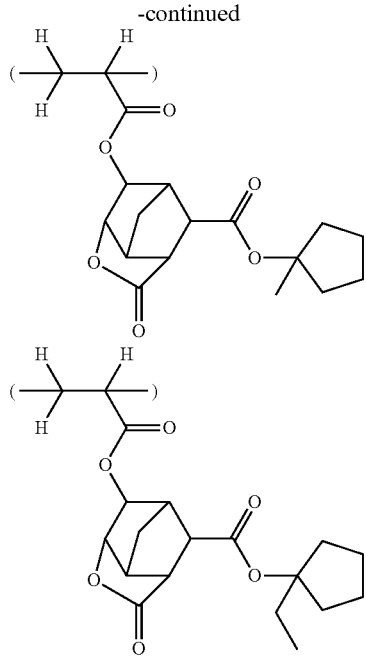
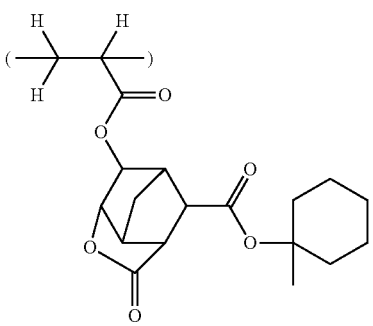
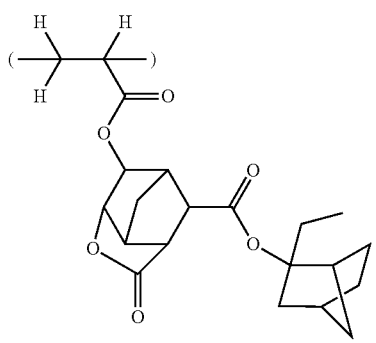
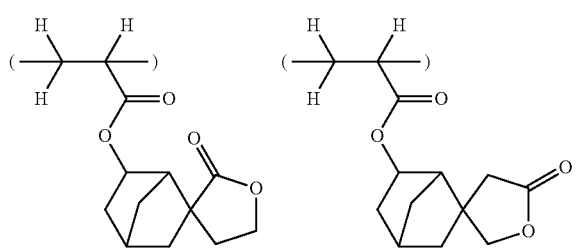
-continued
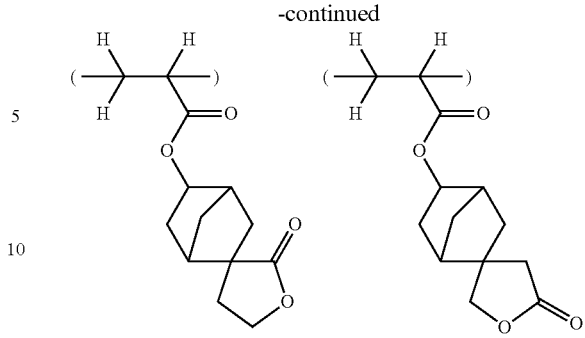
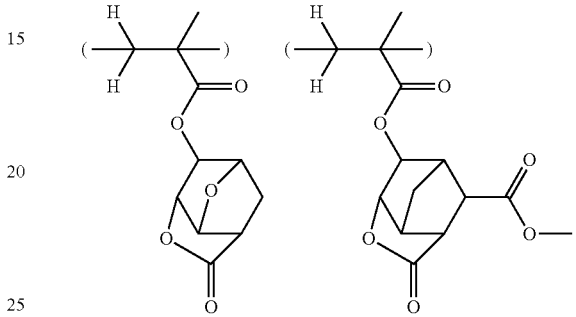
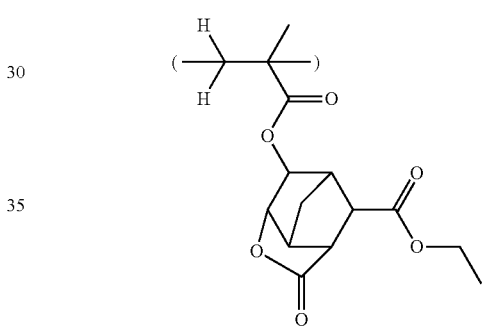
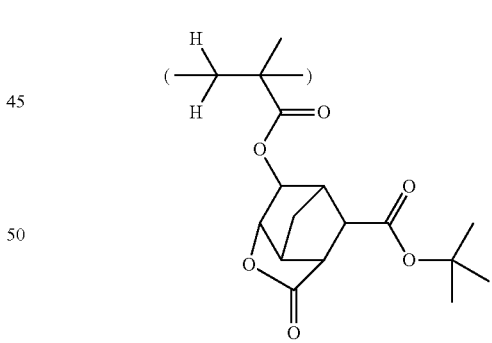
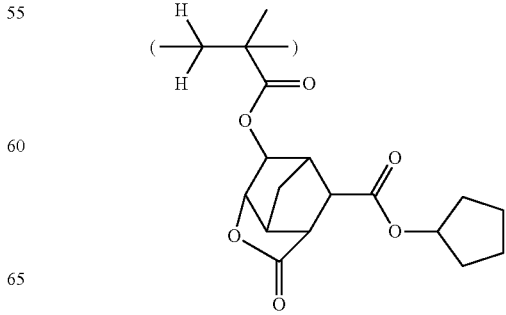

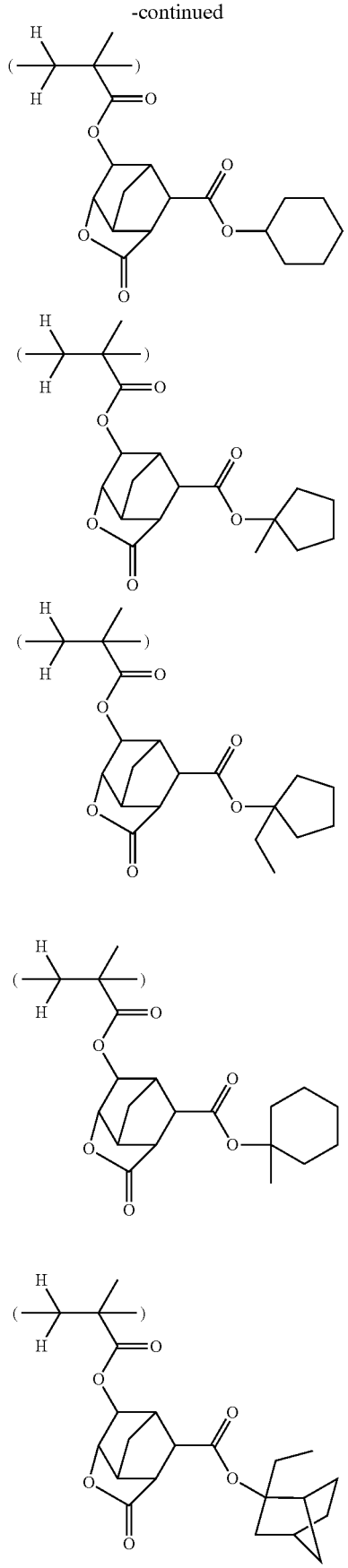
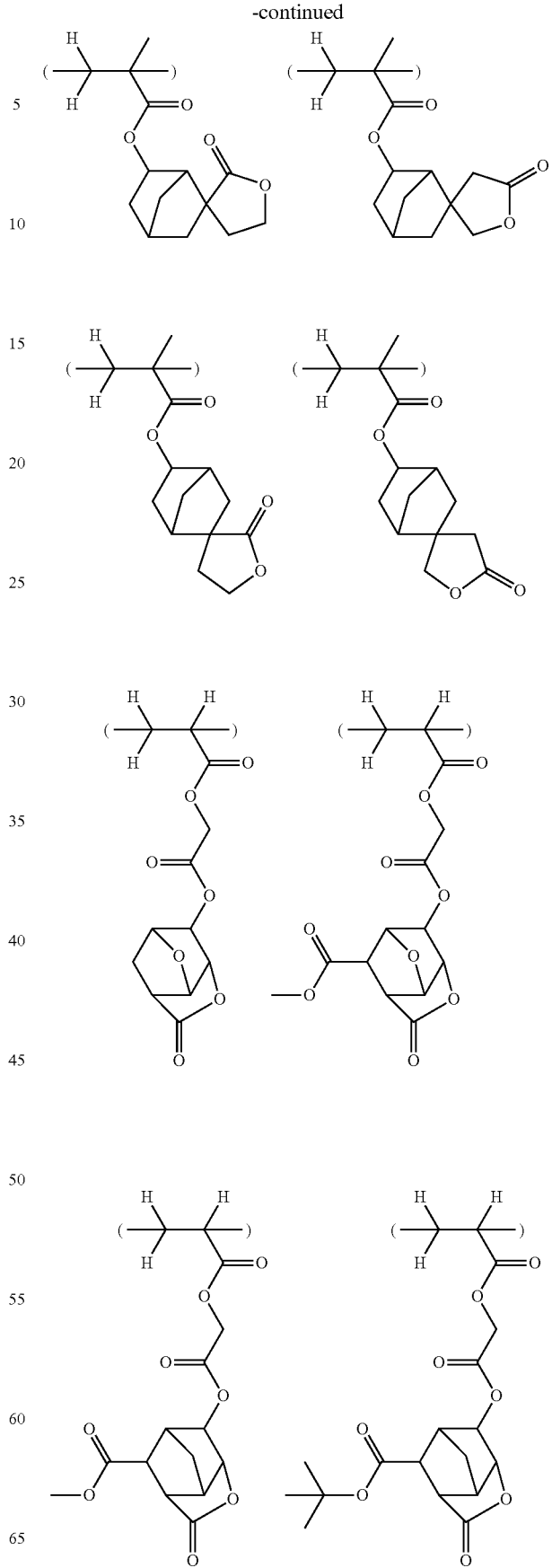

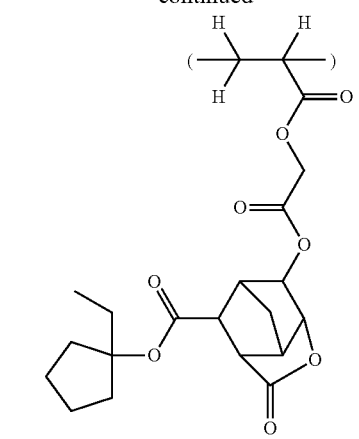
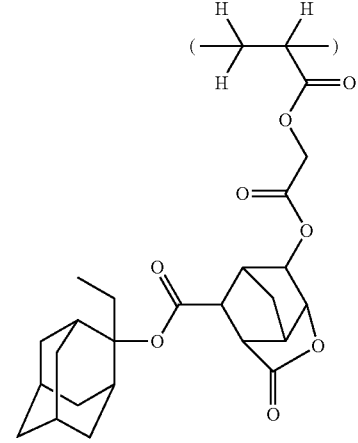
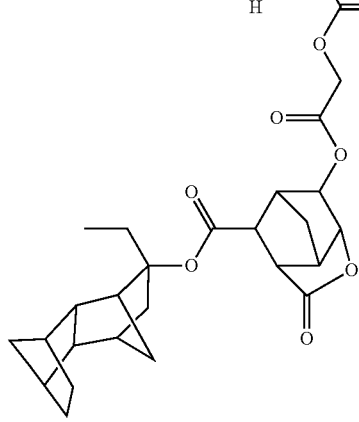
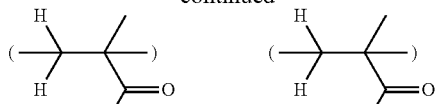
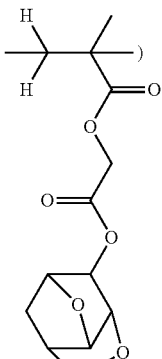
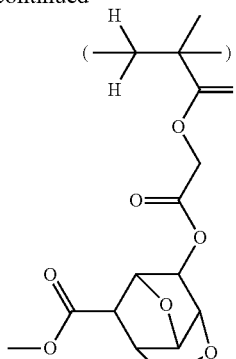
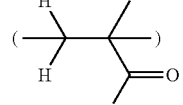
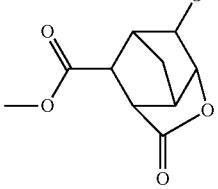
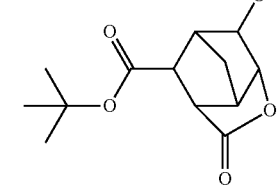
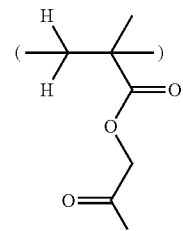
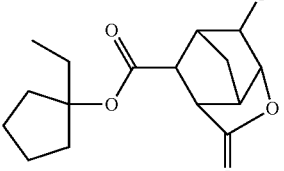
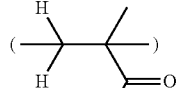
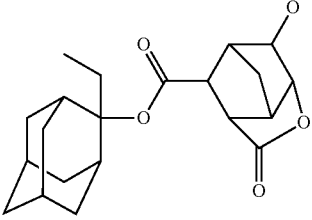

-continued
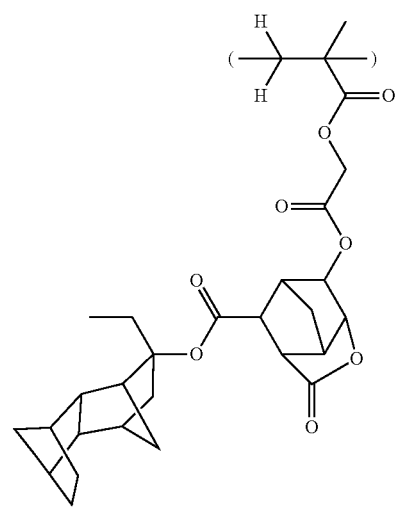
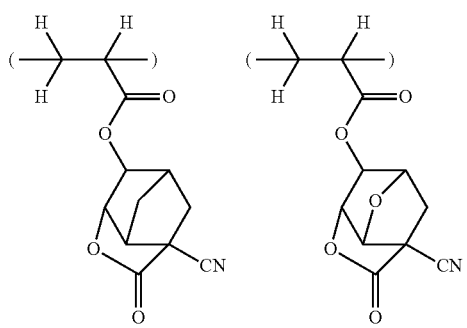
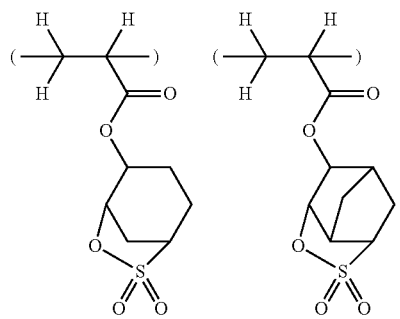
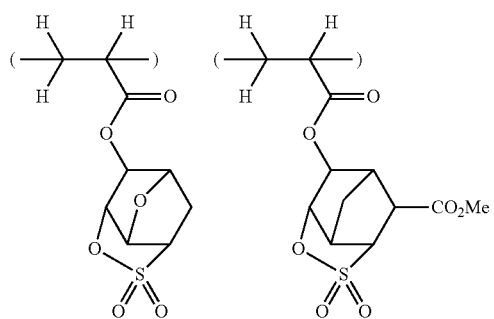
-continued
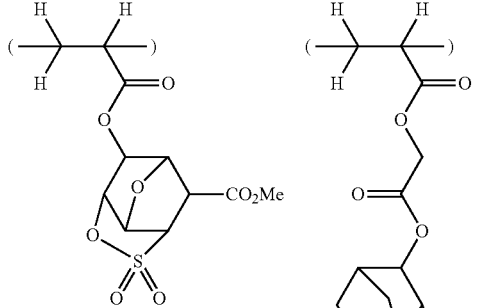
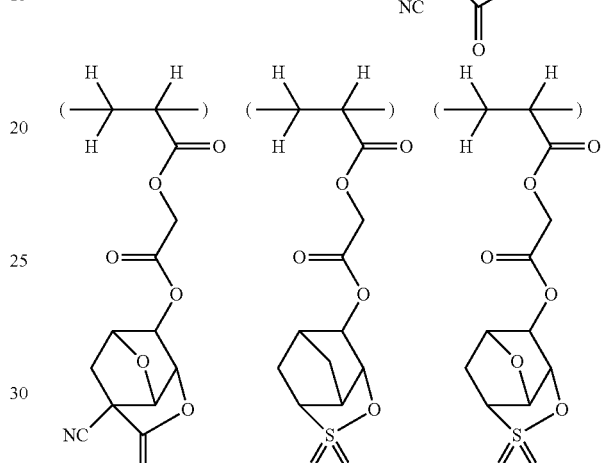
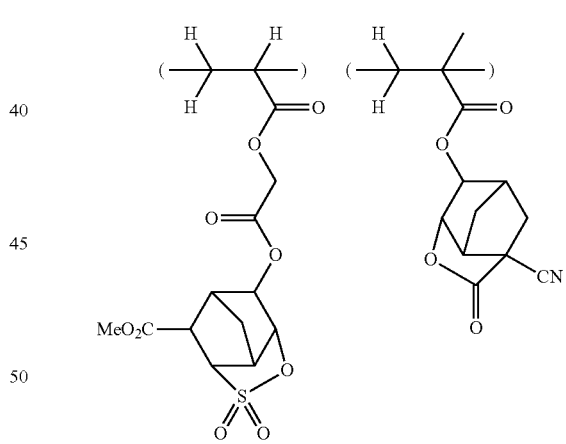
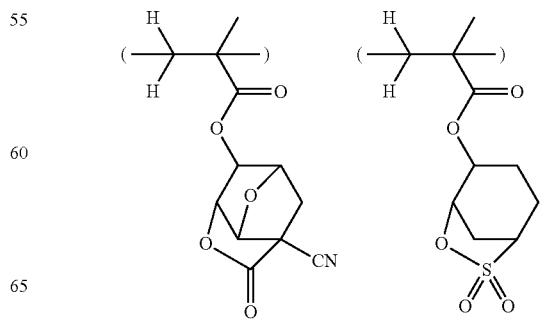

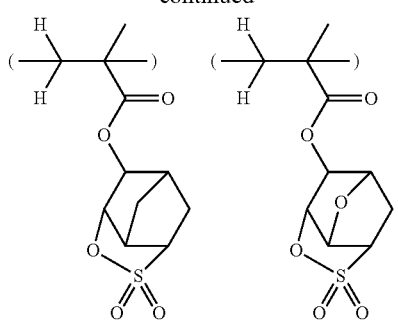
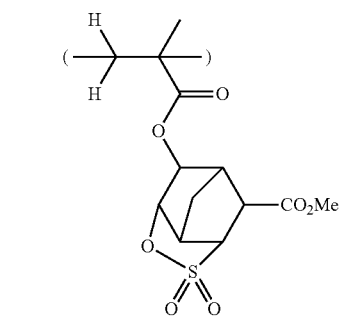
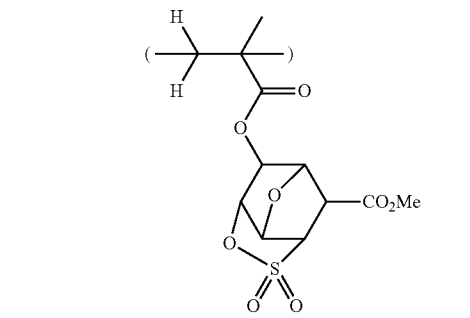
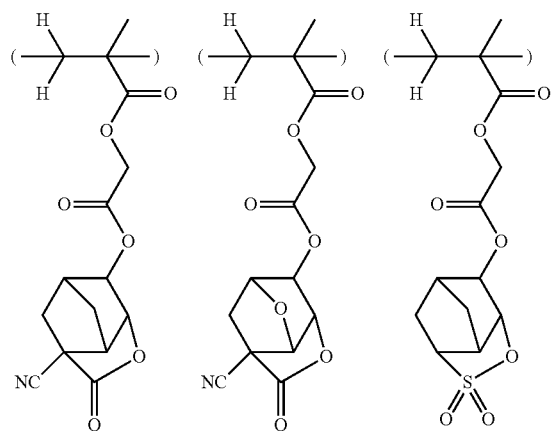
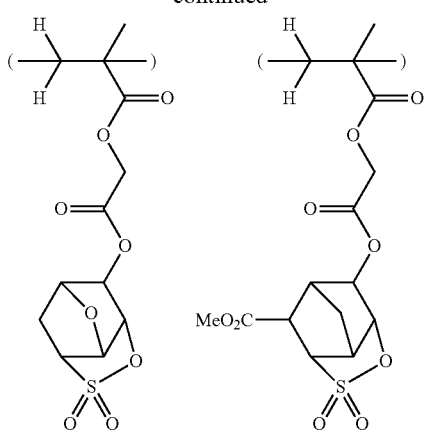
Herein Me stands for methyl.
Illustrative examples of the recurring units of formula (2D) are given below, but not limited thereto.
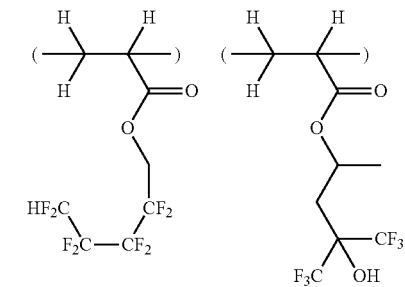

-continued
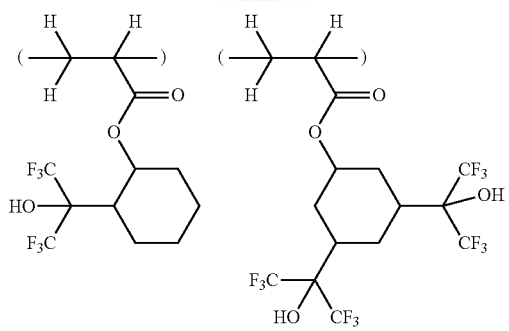
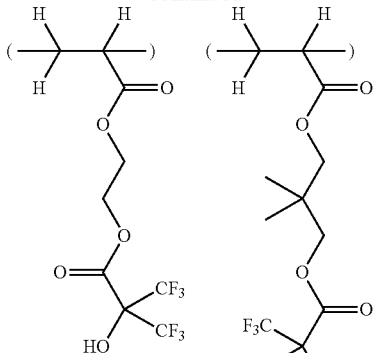
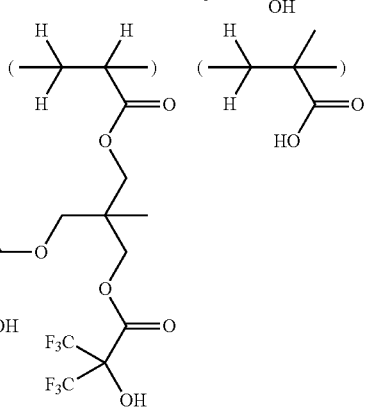
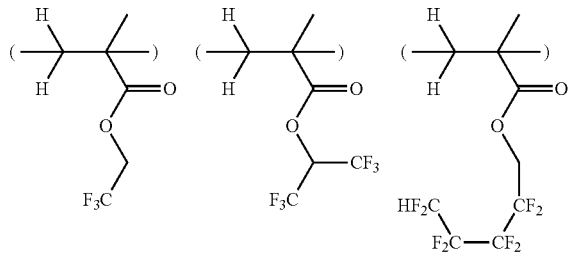
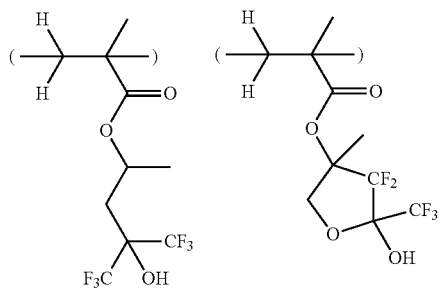
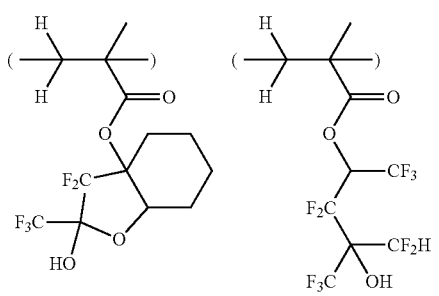

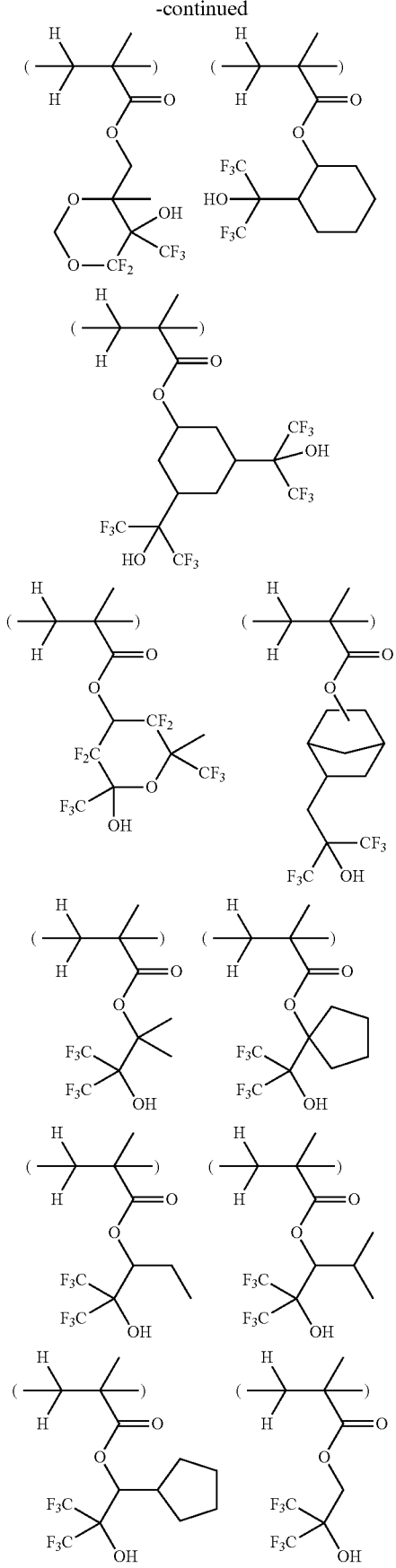
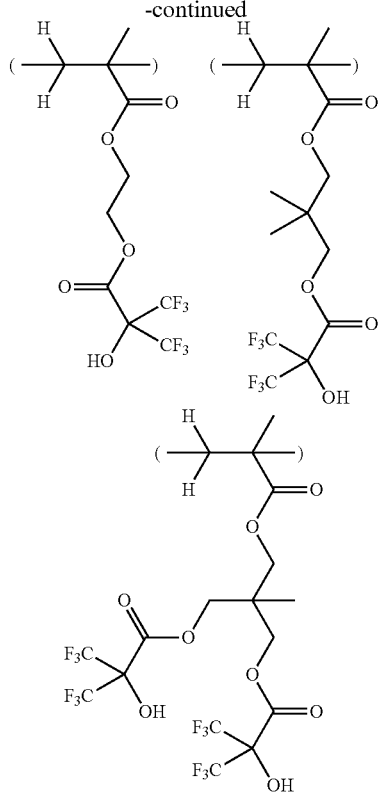
The polymer may further have copolymerized therein at least one sulfonium salt selected from the general formulas (d1) to (d3).
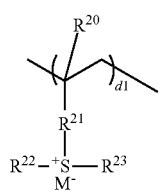
(d1)
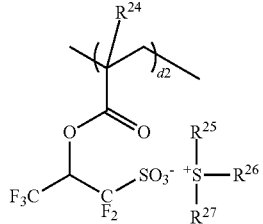
(d2)
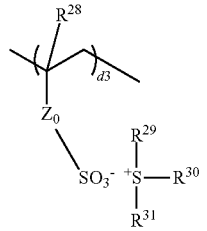
(d3)
Herein $R^{20}$, $R^{24}$ and $R^{28}$ each are hydrogen or methyl. $R^{21}$ is a single bond, phenylene, —O—$R^{33}$—, or —C(=O)—

Y—R$^{33}$— wherein Y is oxygen or NH, and R$^{33}$ is a $C_1$-$C_6$ straight, branched or cyclic alkylene group, alkenylene group or phenylene group, which may contain a carbonyl (—CO—), ester (—COO—), ether (—O—) or hydroxyl radical. R$^{22}$, R$^{23}$, R$^{25}$, R$^{26}$, R$^{27}$, R$^{29}$, R$^{30}$, and R$^{31}$ are each independently a $C_1$-$C_{12}$ straight, branched or cyclic alkyl group which may contain a carbonyl, ester or ether radical, or $C_6$-$C_{12}$ aryl group, $C_7$-$C_{20}$ aralkyl group or thiophenyl group. $Z_0$ is a single bond, methylene, ethylene, phenylene, fluorinated phenylene, —O—R$^{32}$—, or —C(=O)—$Z_1$—R$^{32}$— wherein $Z_1$ is oxygen or NH, and R$^{32}$ is a $C_1$-$C_6$ straight, branched or cyclic alkylene, alkenylene or phenylene group, which may contain a carbonyl, ester, ether or hydroxyl radical. M$^-$ is a non-nucleophilic counter ion.

In addition to the foregoing units, the polymers of the invention may further comprise recurring units derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.1$^{7,10}$]dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured versus polystyrene standards by gel permeation chromatography (GPC) using tetrahydrofuran as solvent. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:
(I) constituent units of one or more types having formula (2a) and/or (2b) derived from monomers of formula (1) and/or (2) in a proportion of more than 0 mol % to 100 mol %, preferably 5 to 70 mol %, and more preferably 10 to 50 mol %,
(II) constituent units of one or more types having formulas (2A) to (2D) in a proportion of 0 mol % to less than 100 mol %, preferably 30 to 95 mol %, and more preferably 50 to 90 mol %,
(III) constituent units of one or more types having formulas (d1) to (d3) in a proportion of 0 mol % to 30 mol %, preferably 0 to 20 mol %, and more preferably 0 to 10 mol %, and
(IV) constituent units of one or more types derived from other monomers in a proportion of 0 to 80 mol %, preferably 0 to 70 mol %, and more preferably 0 to 50 mol %,
based on the total moles of constituent units.

The polymers of the invention are prepared by copolymerization reaction using the compound of formula (1) and/or (2) as a first monomer and polymerizable double bond-bearing compounds as second and subsequent monomers. The copolymerization reaction to produce the inventive polymers may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the positive resist composition contains (A) the inventive polymer as a base resin, (B) an acid generator, (C) an organic solvent, and optionally (D) a nitrogen-containing organic compound and (E) a surfactant. It is understood that acid generator (B) may be omitted when the polymer used has recurring units of formula (d1), (d2) or (d3) copolymerized.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymerization (ROMP) polymers, and (iv) vinyl ether-maleic anhydride-(meth) acrylic acid derivative copolymers.

Of these, the hydrogenated ROMP polymers are synthesized by the method illustrated in JP-A 2003-66612. Illustrative examples of such hydrogenated polymers include those polymers having the recurring units shown below, but are not limited thereto.

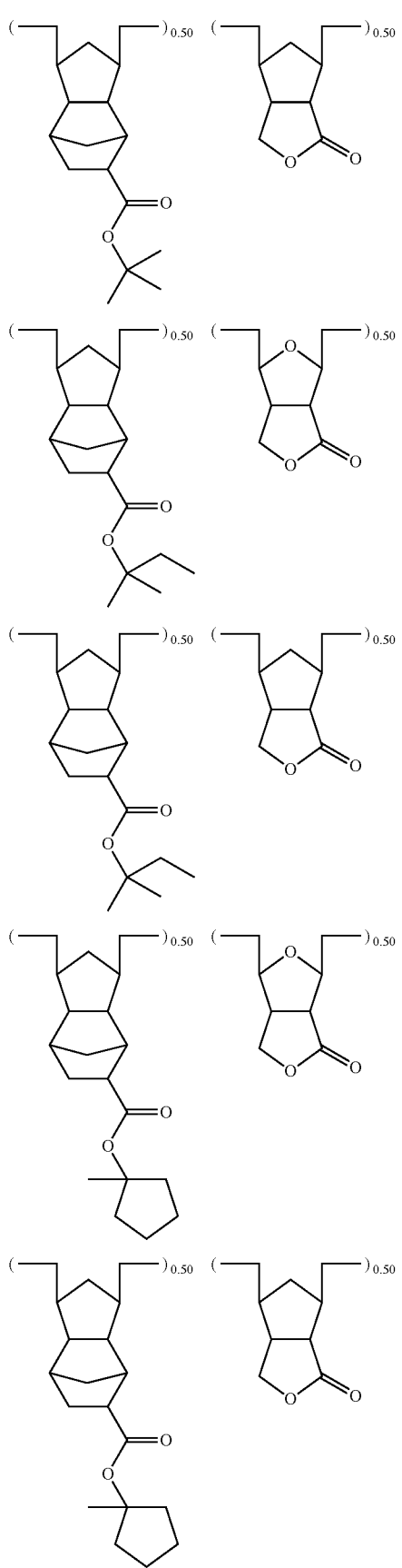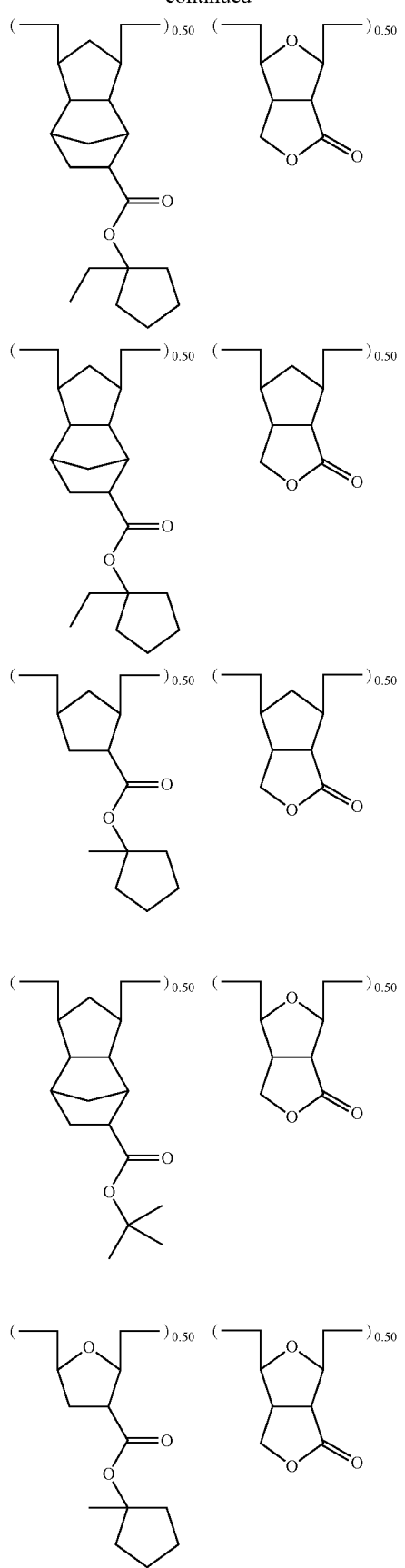

-continued
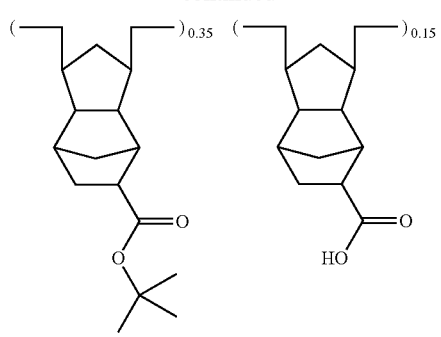
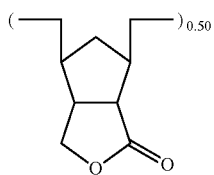
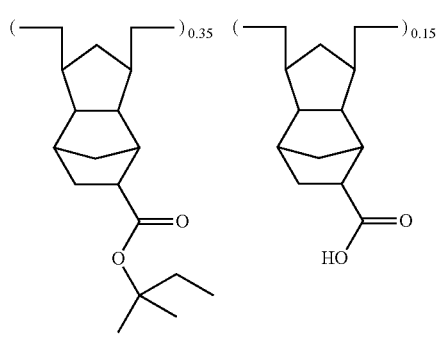
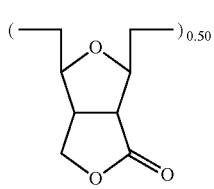
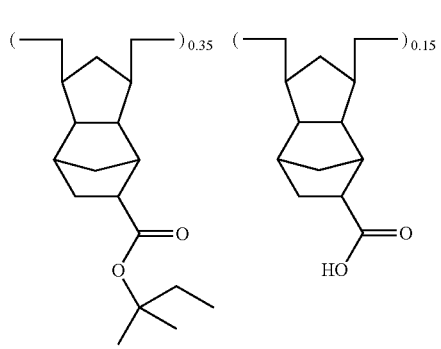
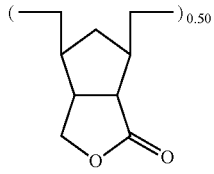
-continued
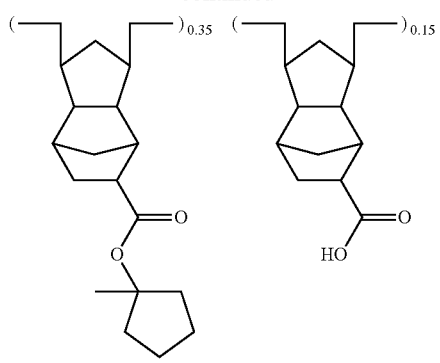
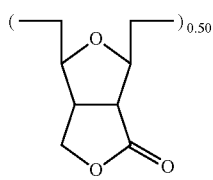
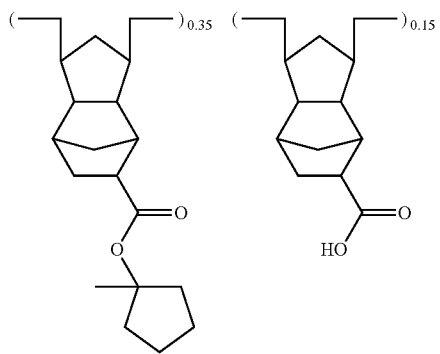
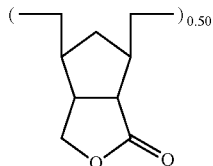
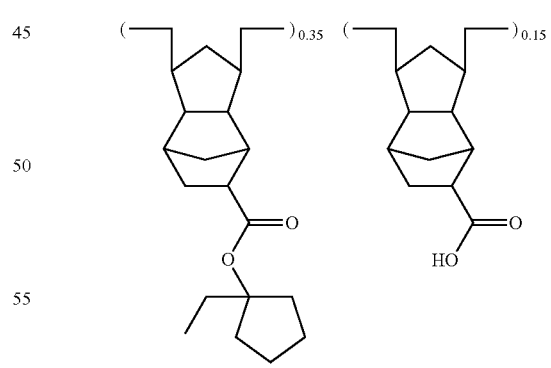
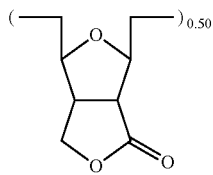

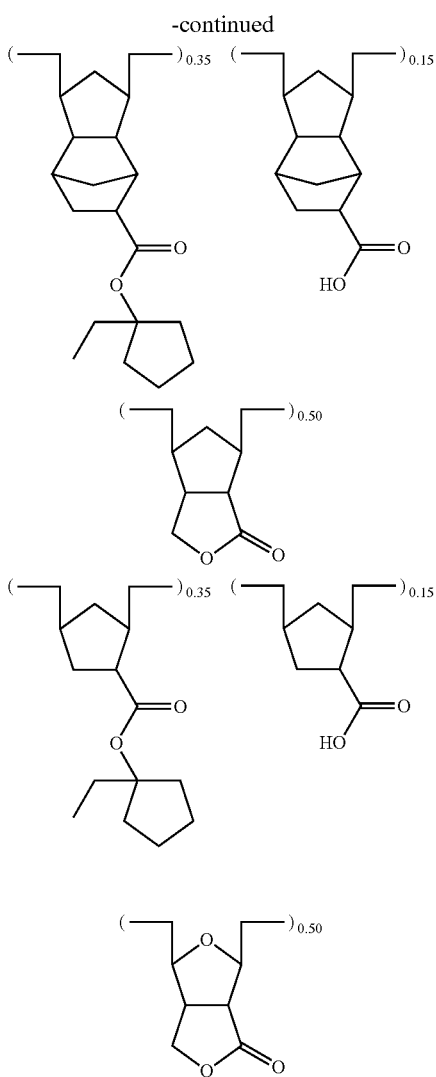

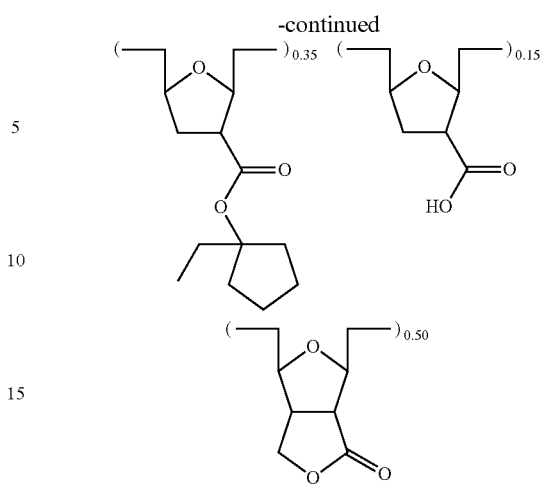

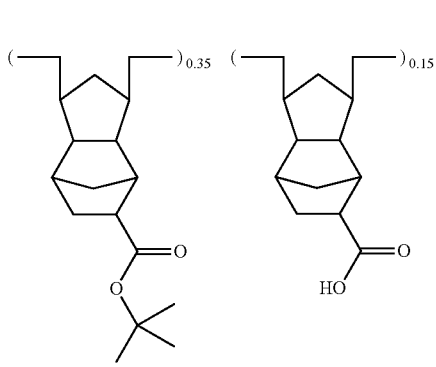

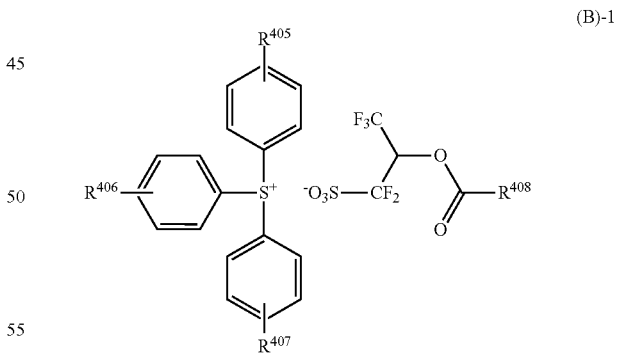

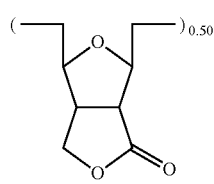

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The polymer is not limited to one type and a mixture of two or more polymers may be added. The use of plural polymers allows for adjustment of resist properties.

Acid Generator

As the acid generator (B), a photoacid generator is typically used. It is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. Exemplary PAGs are given in US 20090274978 (JP-A 2009-269953, paragraphs [0151] to [0156]).

Among others, acid generators having the general formula (B-1) are preferred.

Herein $R^{405}$, $R^{406}$, and $R^{407}$ are each independently hydrogen or a straight, branched or cyclic, monovalent $C_1$-$C_{20}$ hydrocarbon group, typically an alkyl or alkoxy group, which may contain a heteroatom. $R^{408}$ is a straight, branched or cyclic, monovalent $C_7$-$C_{30}$ hydrocarbon group which may contain a heteroatom.

Examples of the optionally heteroatom-containing $C_1$-$C_{20}$ hydrocarbon groups represented by $R^{405}$, $R^{406}$, and $R^{407}$ include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional radical such as —OH, —NH$_2$, —CHO, or —CO$_2$H. Examples of the optionally heteroatom-containing $C_7$-$C_{30}$ hydrocarbon groups represented by $R^{408}$ are given below, but are not limited thereto.

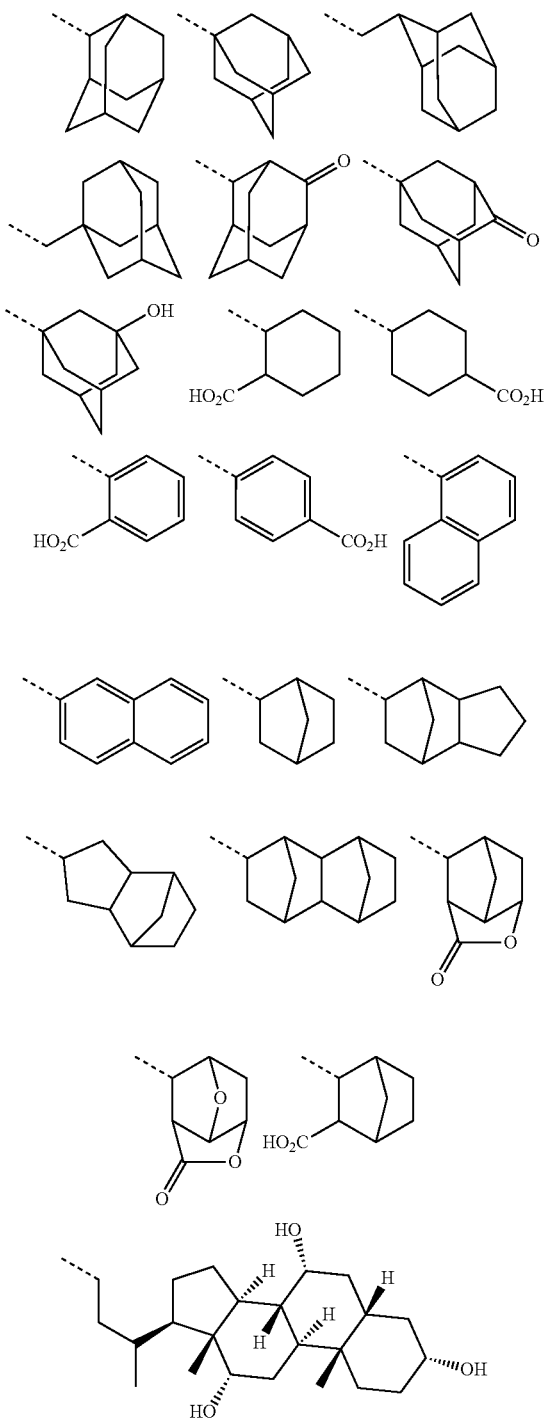

Illustrative examples of acid generator (B-1) are shown below, but not limited thereto.

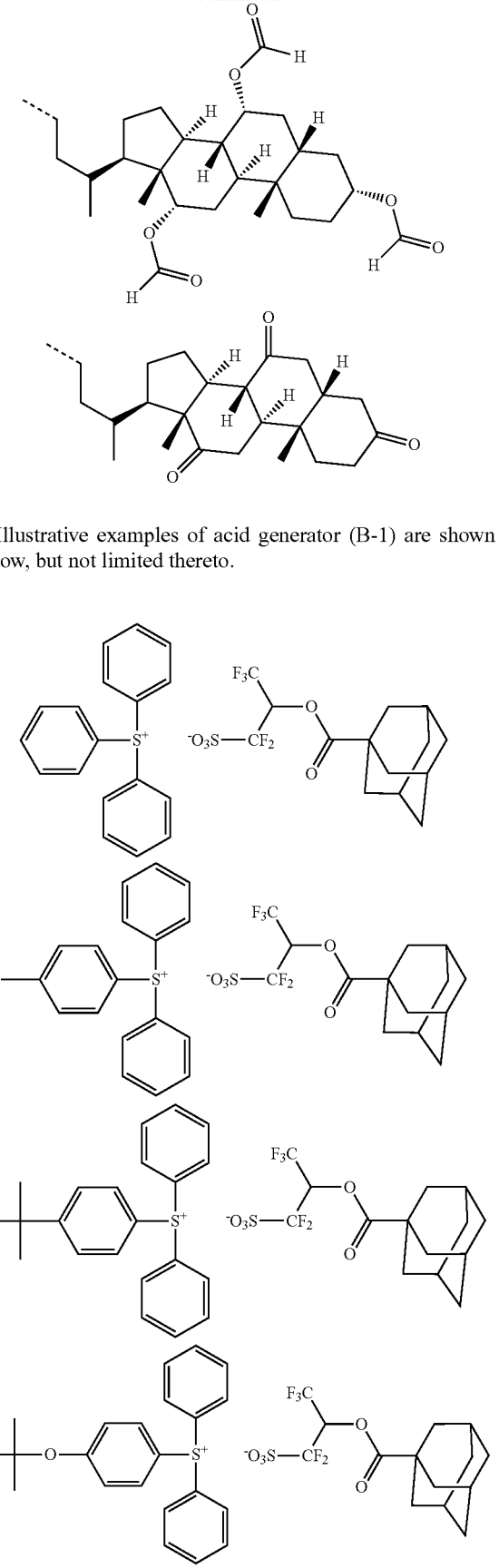

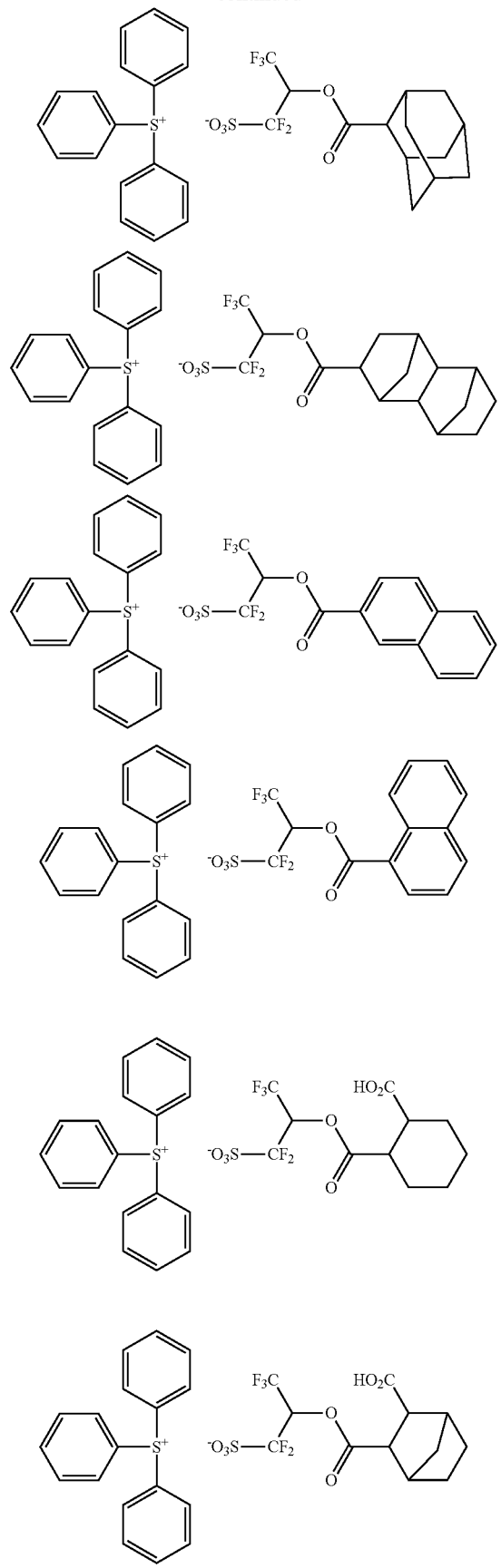
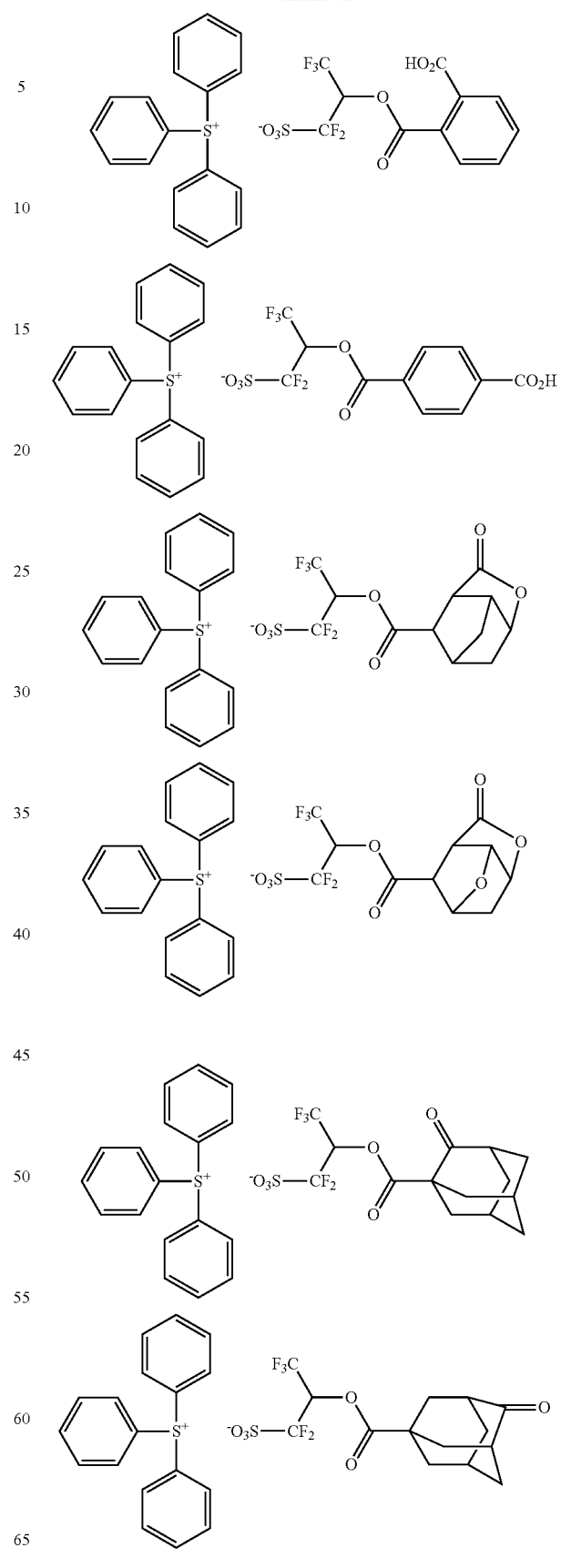

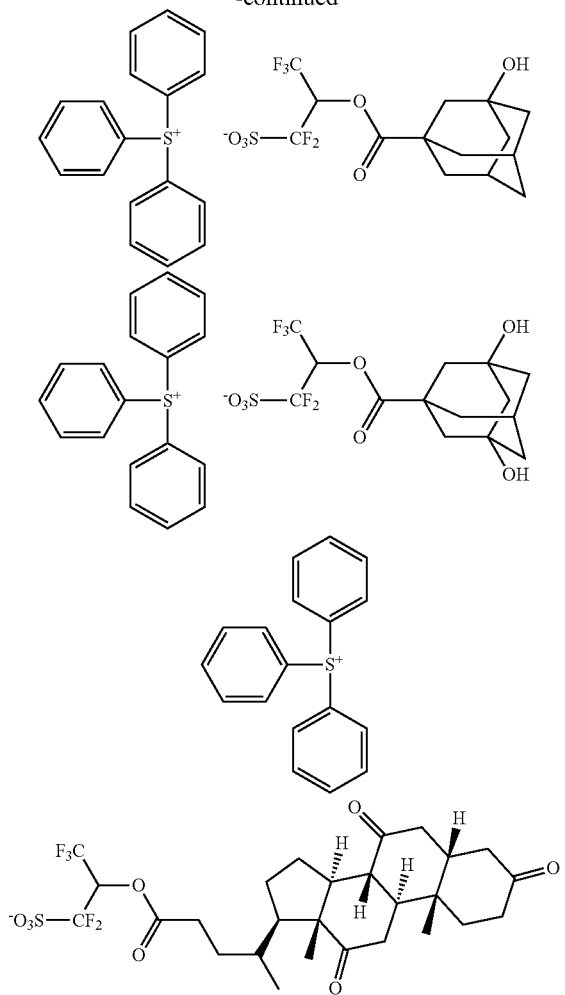

It is noted that an acid diffusion controlling function may be provided when two or more PAGs are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated by the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid is used, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In the resist composition, the PAG may be added in an amount of 0.1 to 40 parts, and more preferably 0.1 to 20 parts by weight per 100 parts by weight of the base resin. As long as the amount of the PAG is up to 40 parts by weight, the resist film keeps a high transmittance and eliminates a risk of resolution being degraded. The PAGs may be used alone or in admixture of two or more. The transmittance of the resist film can be controlled by using a PAG having a low transmittance at the exposure wavelength and adjusting the amount of the PAG added.

In the resist composition, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996). Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior. In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is 200 to 1,000 parts, especially 400 to 800 parts by weight per 100 parts by weight of the base resin.

Nitrogen-Containing Compound

A nitrogen-containing organic compound (D) may be optionally used in the resist composition. The nitrogen-containing organic compound, also referred to as "quencher," is preferably a compound capable of suppressing the rate of diffusion when the acid generated by the PAG diffuses within the resist film. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile.

Examples of the nitrogen-containing organic compound include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Examples are described in JP-A 2009-269953, paragraphs [0122] to [0141].

The nitrogen-containing organic compound is preferably formulated in an amount of 0.001 to 8 parts, and especially 0.01 to 4 parts by weight, per 100 parts by weight of the base resin. Less than 0.001 part of the compound may achieve no addition effect whereas more than 8 parts may lead to too low a sensitivity.

Surfactant

Optionally, the resist composition may further comprise (E) a surfactant. Illustrative, non-limiting examples of the surfactant include nonionic surfactants, for example, perfluoroalkylpolyoxyethylene ethanols, fluorinated alkyl esters, perfluoroalkylamine oxides, perfluoroalkyl EO adducts, and fluorinated organosiloxane compounds. Suitable surfactants are commercially available, for example, under the trade name of Fluorad FC-430 and FC-431 (3M-Sumitomo Co., Ltd.), Surflon S-141, S-145, KH-10, KH-20, KH-30, and KH-40 (Asahi Glass Co., Ltd.), Unidyne DS-401, DS-403 and DS-451 (Daikin Co., Ltd.), Megaface F-8151 (DIC Corp.), X-70-092 and X-70-093 (Shin-Etsu Chemical Co., Ltd.). Of these, preference is given to Fluorad FC-430, KH-20, KH-30, and X-70-093.

In the resist composition, an additive polymer may be added as another optional ingredient. This additive polymer tends to segregate in the sub-surface region of the resist coating and has the functions of tailoring the hydrophilic/hydrophobic balance of the surface, enhancing water repellency, and/or preventing low-molecular-weight fractions from flowing into or out of the resist film when the resist film is in contact with water or another liquid. Such a segregating polymer may be added in conventional amounts as long as the objects of the invention are not compromised. The amount is preferably up to 15 parts, more preferably up to 10 parts by weight per 100 parts by weight of the base resin.

The segregating polymer is preferably selected from homopolymers and copolymers comprising fluorine-containing units of one or more types, and copolymers comprising fluorine-containing units and other units. Exemplary fluorine-containing units and other units are illustrated below, but not limited thereto.

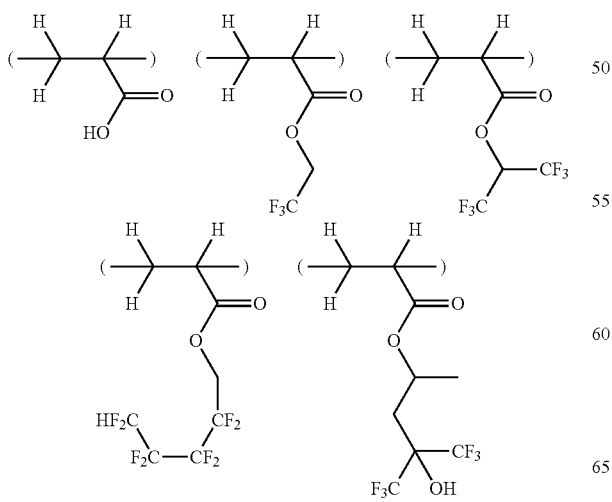

-continued

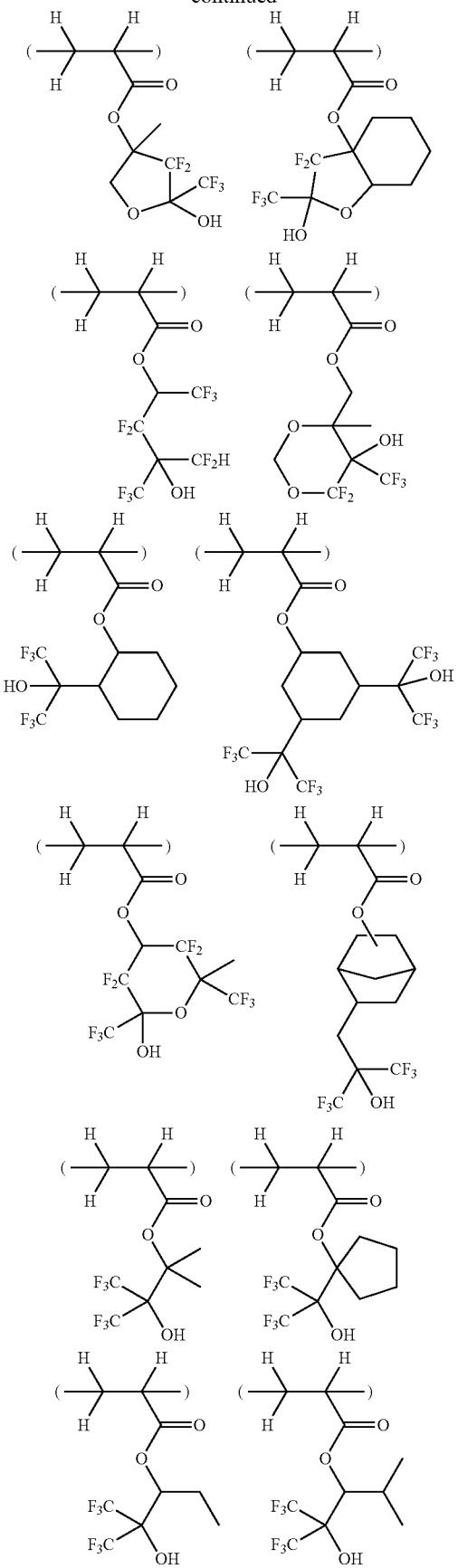

101
-continued
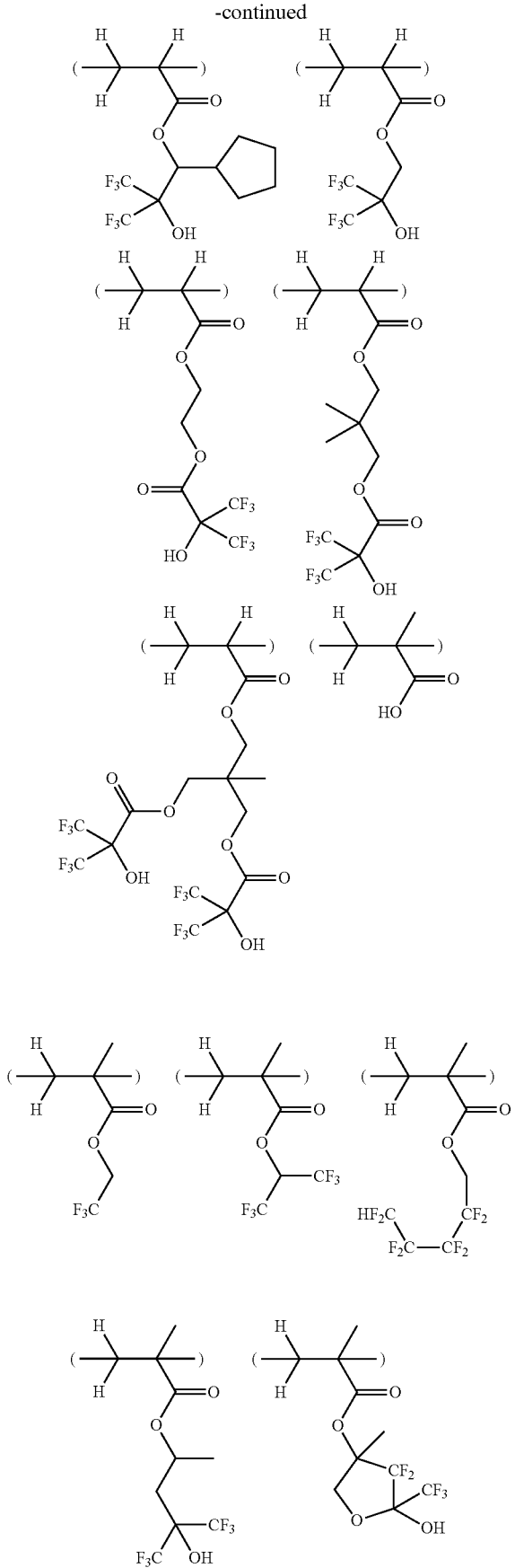
102
-continued
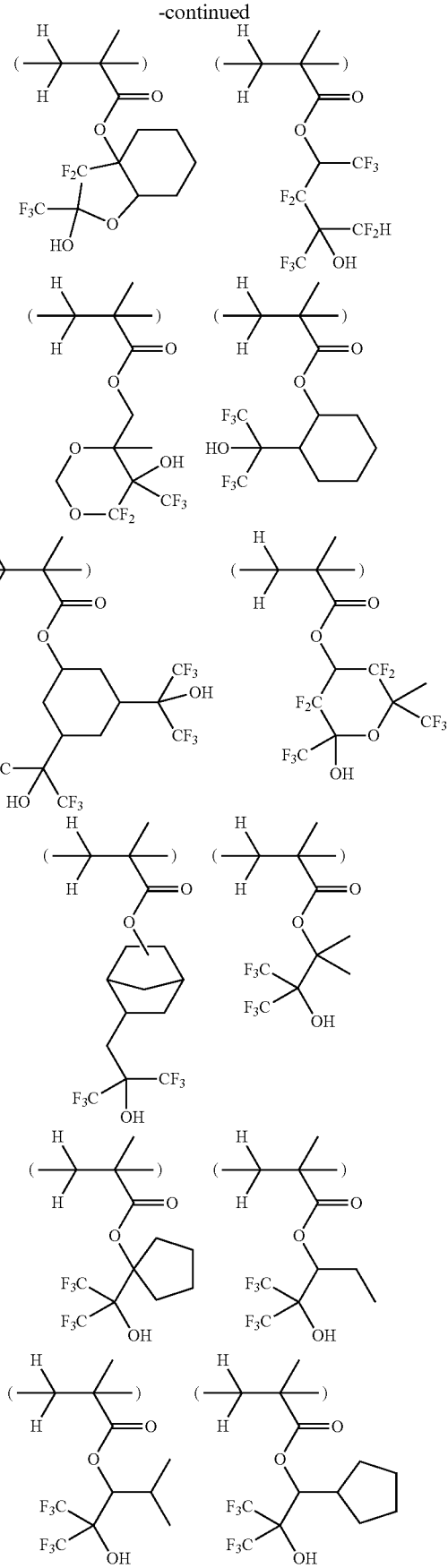

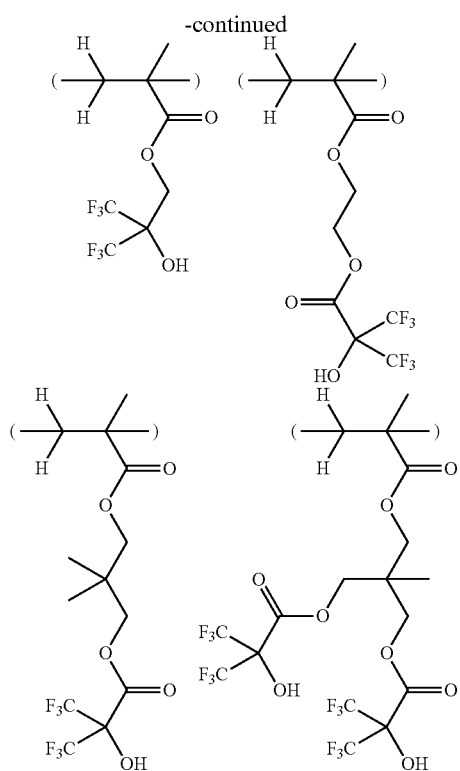

Preferably the segregating polymer has a Mw of 1,000 to 50,000, and more preferably 2,000 to 20,000, as measured by GPC versus polystyrene standards. Outside the range, the surface modifying effect may be insufficient or development defects may form.

While the resist composition of the invention typically comprises a polymer or base resin, acid generator, organic solvent and organic nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be performed by well-known lithography processes. The process generally involves coating, prebaking, exposure, post-exposure baking (PEB), and development. If necessary, any additional steps may be added.

For pattern formation, the resist composition is first applied onto a substrate (on which an integrated circuit is to be formed, e.g., Si, $SiO_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 60 to 150° C. for 1 to 10 minutes, preferably 80 to 140° C. for 1 to 5 minutes. The resulting resist film is generally 0.01 to 2.0 μm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom.

On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist, and the organic film in this case may be an organic antireflective coating. After the photoresist film is formed, deionized water rinsing (or post-soaking) may be carried out for extracting the acid generator and the like from the film surface or washing away particles, or a protective film may be coated.

With a mask having a desired pattern placed above the resist film, the resist film is then exposed to actinic radiation such as UV, deep-UV, electron beam, x-ray, excimer laser light, γ-ray and synchrotron radiation. The exposure dose is preferably about 1 to 200 $mJ/cm^2$, more preferably about 10 to 100 $mJ/cm^2$. The film is further baked (PEB) on a hot plate at 60 to 150° C. for 1 to 5 minutes, preferably 80 to 120° C. for 1 to 3 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate. It is appreciated that the resist composition of the invention is suited for micro-patterning using such high-energy radiation as deep UV with a wavelength of 254 to 193 nm, EUV with a wavelength of 157 nm, electron beam, soft x-ray, x-ray, excimer laser light, γ-ray and synchrotron radiation, and best suited for micropatterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves exposing a prebaked resist film to light through a projection lens, with deionized water or similar liquid interposed between the resist film and the projection lens. Since this allows projection lenses to be designed to a numerical aperture (NA) of 1.0 or higher, formation of finer patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking for preventing any dissolution from the resist and improving water slip on the film surface.

The resist protective coating used in the immersion lithography is preferably formed from a solution of a polymer having 1,1,1,3,3,3-hexafluoro-2-propanol residue which is insoluble in water, but dissolvable in an alkaline developer, in a solvent selected from alcohols of at least 4 carbon atoms, ethers of 8 to 12 carbon atoms, and mixtures thereof.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

EXAMPLE

Examples of the invention are given below by way of illustration and not by way of limitation. "Mw" is a weight average molecular weight as measured by GPC versus polystyrene standards, and "pbw" is parts by weight. Me stands for methyl.

Synthesis Example 1

Polymerizable ester compounds within the scope of the invention were synthesized according to the following formulation.

Synthesis Example 1-1

Synthesis of Monomer 1

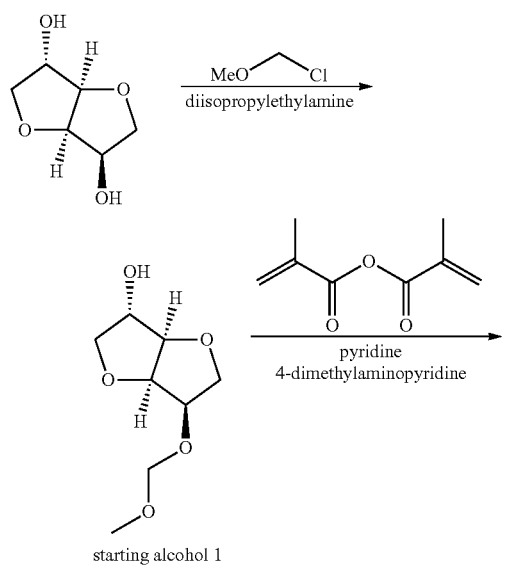

starting alcohol 1

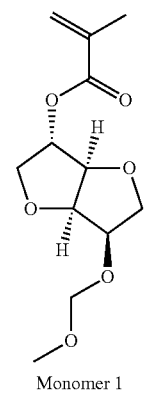

Monomer 1

Synthesis Example 1-1-1

Synthesis of Starting Alcohol 1

A mixture of 103 g of isosorbide, 91 g of N,N-diisopropylethylamine, 36 g of acetonitrile, and 40 g of tetrahydrofuran (THF) was heated at 40° C., to which 14.2 g of methoxymethyl chloride was added dropwise. Stirring was continued at 40° C. for 10 hours, whereupon sodium hydrogen carbonate aqueous solution was added to quench the reaction. This was followed by ordinary aqueous workup and purification by silica gel column chromatography, obtaining 51 g of starting alcohol 1 (yield 89%).

It is noted that the product as purified consisted of a major isomer of the above formula and a minor isomer in a ratio of 58:42 mol %.

Synthesis Example 1-1-2

Synthesis of Monomer 1

In 350 mL of toluene were dissolved 13.8 g of the starting alcohol 1, 9.2 g of pyridine, and 0.88 g of 4-(dimethylamino)pyridine. To this solution at 50-60° C., 12.8 g of methacrylic anhydride was added dropwise. The solution was stirred at 60° C. for one day, whereupon sodium hydrogen carbonate aqueous solution was added to quench the reaction. After ordinary aqueous workup, the solvent was distilled off. Purification by distillation gave 17.9 g of Monomer 1 (yield 96%).

It is noted that the product as purified consisted of a major isomer of the above formula and a minor isomer in a ratio of 57:43 mol %.

boiling point: 100-102° C./14 Pa

IR (D-ATR): ν=2953, 2888, 1721, 1637, 1454, 1403, 1379, 1316, 1297, 1163, 1103, 1040, 917 cm$^{-1}$ $^1$H-NMR (600 MH in DMSO-d$_6$, only major isomer data): δ=6.03 (1H, s), 5.70 (1H, m), 5.06 (1H, d), 4.59-4.66 (3H, m), 4.46 (1H, d), 4.12-4.18 (1H, m), 3.65-3.93 (3H), 3.48 (1H, t), 3.25 (2H, s), 1.87 (3H, m) ppm

Synthesis Example 1-2

Synthesis of Monomer 2

Monomer 2 was produced by the same procedures as Synthesis Examples 1-1-1 and 1-1-2 except that acrylic anhydride was used instead of methacrylic anhydride. Two-step yield 62%.

Synthesis Example 1-3

Synthesis of Monomer 3

Monomer 3 was produced by the same procedures as Synthesis Examples 1-1-1 and 1-1-2 except that α-trifluoromethylacrylic anhydride was used instead of methacrylic anhydride. Two-step yield 51%.

Synthesis Example 1-4

Synthesis of Monomer 4

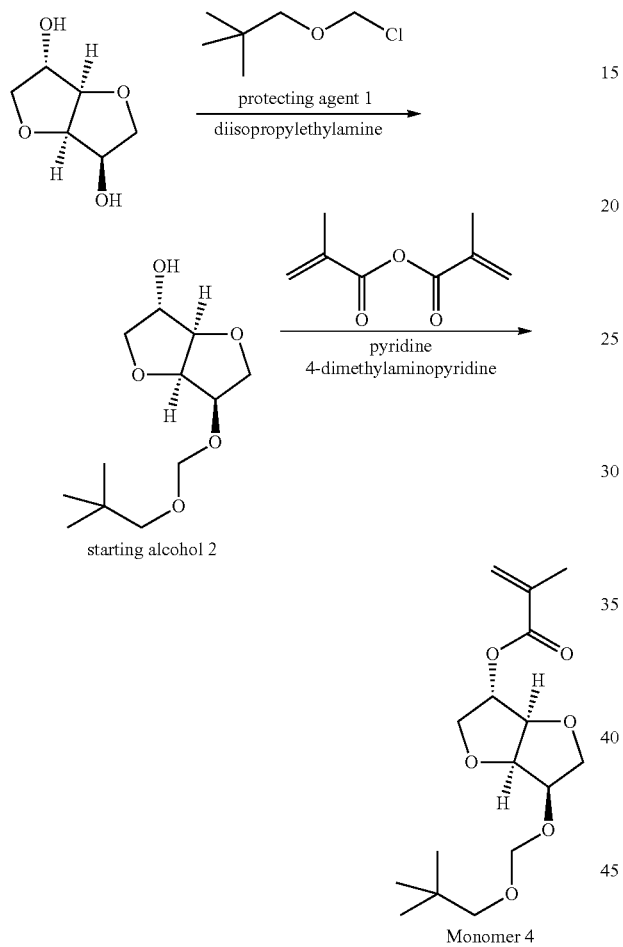

Monomer 4

Synthesis Example 1-4-1

Synthesis of Starting Alcohol 2

Starting alcohol 2 was prepared by the same procedure as Synthesis Example 1-1-1 except that protecting agent 1 was used instead of methoxymethyl chloride. Yield 82%.

Example 1-4-2

Synthesis of Monomer 4

Monomer 4 was prepared by the same procedure as Synthesis Example 1-1-2 except that starting alcohol 2 was used instead of starting alcohol 1. It is noted that the product as purified consisted of a major isomer of the above formula and a minor isomer in a ratio of 54:46 mol %.

boiling point: 122-124° C./15 Pa

IR (D-ATR): ν=2955, 2870, 1722, 1637, 1480, 1466, 1398, 1363, 1316, 1298, 1166, 1108, 1067, 1045, 939 $cm^{-1}$ $^1$H-NMR (600 MH in DMSO-$d_6$, only major isomer data): δ=6.00 (1H, s), 5.68 (1H, m), 5.03 (1H, d), 4.64-4.71 (2H, m), 4.59 (1H, t), 4.44 (1H, d), 4.12-4.17 (1H, m), 3.76-3.93 (2H), 3.45 (1H, t), 3.08-3.17 (2H, m), 1.83 (3H, s), 0.85 (9H, s) ppm

Synthesis Example 1-5

Synthesis of Monomer 5

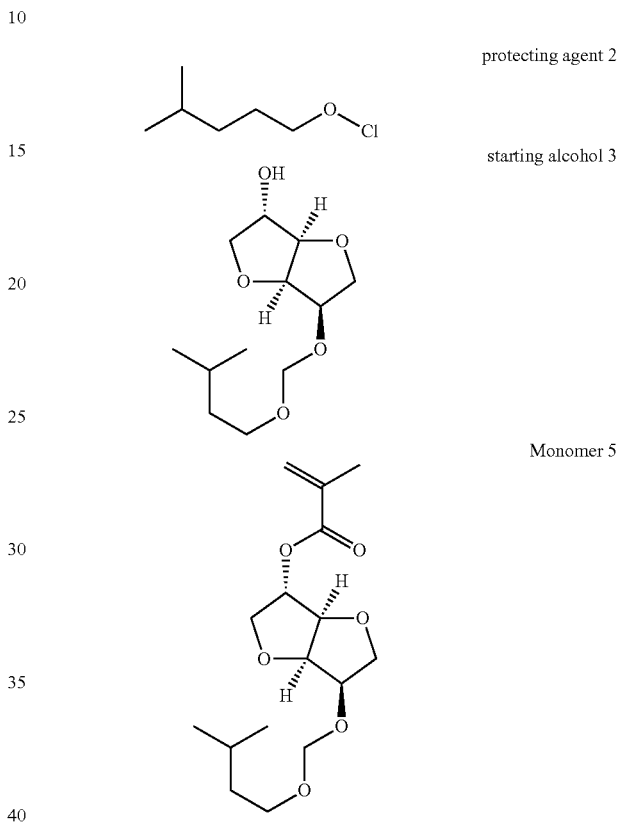

Monomer 5

Synthesis Example 1-5-1

Synthesis of Starting Alcohol 3

Starting alcohol 3 was prepared by the same procedure as Synthesis Example 1-1-1 except that protecting agent 2 was used instead of methoxymethyl chloride. Yield 78%. It is noted that the product as purified consisted of a major isomer of the above formula and a minor isomer in a ratio of 56:44 mol %.

IR (D-ATR): ν=3448, 2955, 2872, 1467, 1385, 1180, 1112, 1067, 885, 833, 776, 614 $cm^{-1}$ $^1$H-NMR (600 MH in DMSO-$d_6$, only major isomer data): δ=5.12 (1H, d), 4.62-4.67 (2H, m), 4.50 (1H, t), 4.25 (1H, d), 4.06-4.12 (3H, m), 4.01-4.04 (1H, m), 3.46-3.53 (3H, m), 3.36 (1H, t), 1.60-1.68 (1H, m), 1.36-1.41 (2H, m), 0.86 (3H, d), 0.85 (3H, d) ppm

Example 1-5-2

Synthesis of Monomer 5

Monomer 5 was prepared by the same procedure as Synthesis Example 1-1-2 except that starting alcohol 3 was used instead of starting alcohol 1. It is noted that the product as purified consisted of a major isomer of the above formula and a minor isomer in a ratio of 60:40 mol %.

boiling point: 132-134° C./15 Pa

IR (D-ATR): ν=2956, 2872, 1722, 1638, 1465, 1384, 1316, 1299, 1164, 1108, 1071, 1037, 941, 850, 814, 776, 654 cm$^{-1}$ $^1$H-NMR (600 MH in DMSO-d$_6$, only major isomer data): δ=6.03 (1H, s), 5.72-5.68 (1H, m), 5.06 (1H, d), 4.64-4.69 (2H, m), 4.60 (1H, t), 4.47 (1H, d), 4.16 (1H, dd-like), 3.93 (1H, dd), 3.80-3.89 (3H, m), 3.45-3.55 (2H, m), 1.84-1.88 (3H, m), 1.61-1.68 (1H, m), 1.39 (2H, dd), 0.87 (3H, d), 0.85 (3H, d) ppm Synthesis Example 1-6

Synthesis of Monomer 6

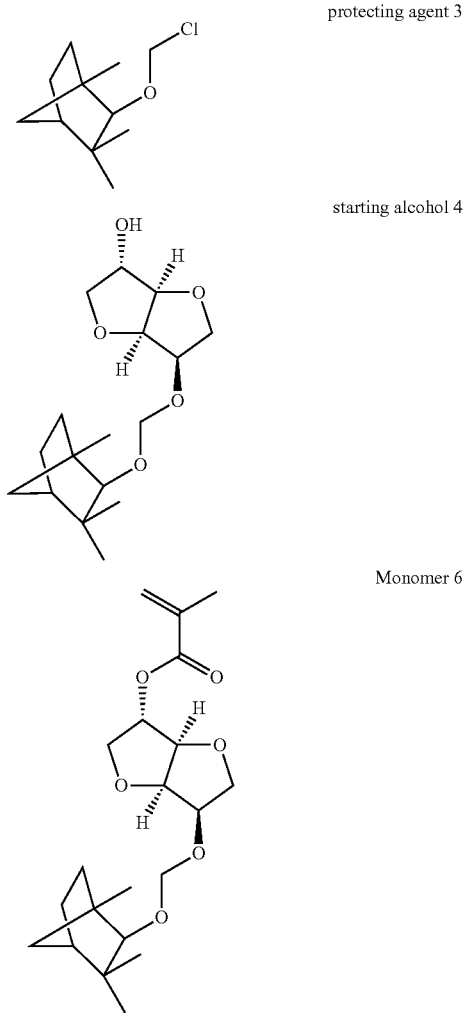

Synthesis Example 1-6-1

Synthesis of Starting Alcohol 4

Starting alcohol 4 was prepared by the same procedure as Synthesis Example 1-1-1 except that protecting agent 3 was used instead of methoxymethyl chloride. Yield 89%. It is noted that the product as purified consisted of a major isomer of the above formula and a minor isomer in a ratio of 61:39 mol %.

IR (D-ATR): ν=3429, 2950, 2871, 1461, 1373, 1170, 1113, 1039, 921, 885, 844, 775, 606 cm$^{-1}$ $^1$H-NMR (600 MH in DMSO-d$_6$, only major isomer data): δ=5.11 (1H, d), 4.69 (1H, m), 4.61 (1H, m), 4.56 (1H, m), 4.22-4.25 (2H), 4.02 (1H, m), 3.65-3.79 (3H), 3.41 (1H, m), 3.19 (1H, d), 1.54-1.67 (3H), 1.46 (1H, m), 1.35 (1H, m), 0.88-1.10 (2H), 1.02 (3H, s), 0.99 (3H, s), 0.82 (3H, s) ppm Example 1-6-2

Synthesis of Monomer 6

Monomer 6 was prepared by the same procedure as Synthesis Example 1-1-2 except that starting alcohol 4 was used instead of starting alcohol 1. Yield 98%. It is noted that the product as purified consisted of a major isomer of the above formula and a minor isomer in a ratio of 63:37 mol %.

IR (D-ATR): ν=2953, 2872, 1723, 1460, 1374, 1317, 1298, 1162, 1102, 1080, 1039, 1006, 939, 886, 813, 650 cm$^{-1}$ $^1$H-NMR (600 MH in DMSO-d$_6$, only major isomer data): δ=6.03 (1H, s), 5.70 (1H, m), 5.06 (1H, d), 4.60-4.76 (3H), 4.46 (1H, m), 4.29 (1H, m), 3.73-3.93 (3H), 3.54 (1H, m), 3.21 (1H, m), 1.87 (3H, m), 1.55-1.63 (3H), 1.47 (1H, m), 1.35 (1H, m), 0.88-1.10 (2H), 1.03 (3H, s), 0.99 (3H, s), 0.82 (3H, s) ppm Synthesis Example 1-7

Synthesis of Monomer 7

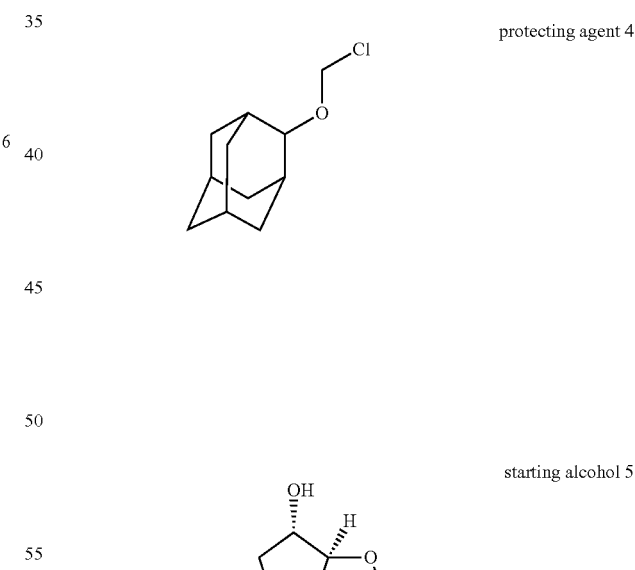

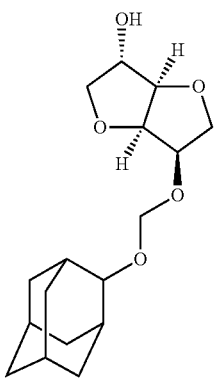

Monomer 7

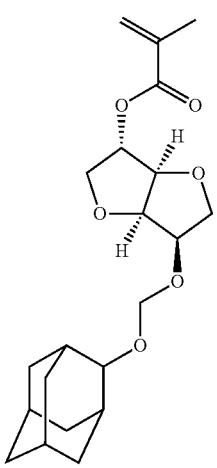

Synthesis Example 1-7-1

Synthesis of Starting Alcohol 5

Starting alcohol 5 was prepared by the same procedure as Synthesis Example 1-1-1 except that protecting agent 4 was used instead of methoxymethyl chloride. Yield 74%. It is noted that the product as purified consisted of a major isomer of the above formula and a minor isomer in a ratio of 60:40 mol %.

IR (D-ATR): ν=3419, 2902, 2851, 1449, 1383, 1170, 1083, 1029, 980, 928, 872, 845, 779 cm$^{-1}$ $^1$H-NMR (600 MH in DMSO-d$_6$, only major isomer data): δ=5.12 (1H, d), 4.72-4.75 (2H, m), 4.51 (1H, t), 4.25 (1H, d), 4.13-4.19 (1H, m), 4.00-4.03 (1H, m), 3.74-3.79 (1H, m), 3.62-3.73 (3H, m), 3.35 (1H, t), 1.87-1.98 (4H, m), 1.70-1.80 (4H, m), 1.58-1.68 (4H, m), 1.40-1.47 (2H, m) ppm

Example 1-7-2

Synthesis of Monomer 7

Monomer 7 was prepared by the same procedure as Synthesis Example 1-1-2 except that starting alcohol 5 was used instead of starting alcohol 1. Yield 96%. It is noted that the product as purified consisted of a major isomer of the above formula and a minor isomer in a ratio of 62:38 mol %.

IR (D-ATR): ν=2903, 2852, 1722, 1637, 1450, 1383, 1316, 1298, 1081, 1046, 1034, 980, 928, 894, 814, 653, 604 cm$^{-1}$ $^1$H-NMR (600 MH in DMSO-d$_6$, only major isomer data): δ=6.03 (1H, s), 5.67-5.72 (1H, m), 5.05 (1H, d), 4.74-4.78 (2H, m), 4.62 (1H, t), 4.47 (1H, d), 4.23 (1H, dd-like), 3.92 (1H, dd), 3.78-3.89 (2H, m), 3.67-3.71 (1H, m), 3.48 (1H, t), 1.84-1.99 (4H, m), 1.70-1.80 (4H, m), 1.58-1.68 (4H, m), 1.40-1.48 (2H, m) ppm

Synthesis Example 1-8

Synthesis of Monomer 8 protecting agent 5

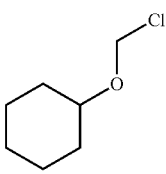

Monomer 8

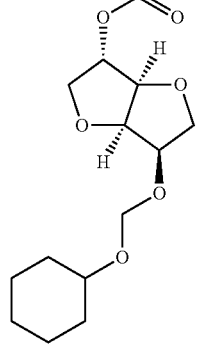

Monomer 8 was prepared by the same procedures as Synthesis Examples 1-1-1 and 1-1-2 except that protecting agent 5 was used instead of methoxymethyl chloride. Two-step yield 66%.

Synthesis Example 1-9

Synthesis of Monomer 9 protecting agent 6

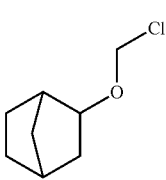

Monomer 9

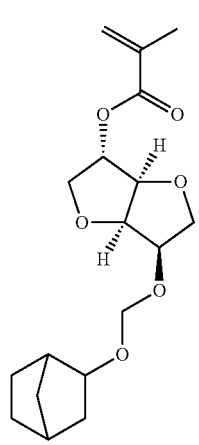

Monomer 9 was prepared by the same procedures as Synthesis Examples 1-1-1 and 1-1-2 except that protecting agent 6 was used instead of methoxymethyl chloride. Two-step yield 65%.

Synthesis Example 1-10

Synthesis of Monomer 10

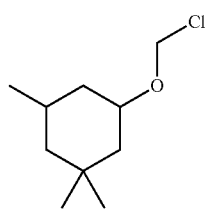

protecting agent 7

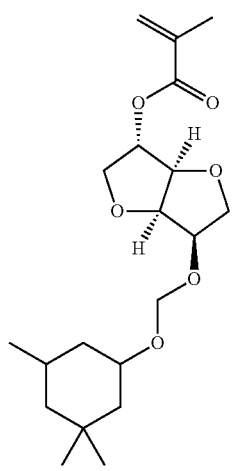

Monomer 10

Monomer 10 was prepared by the same procedures as Synthesis Examples 1-1-1 and 1-1-2 except that protecting agent 7 was used instead of methoxymethyl chloride. Two-step yield 61%.

Synthesis Example 1-11

Synthesis of Monomer 11

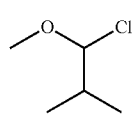

protecting agent 8

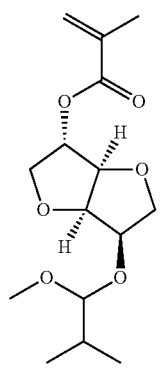

Monomer 11

Monomer 11 was prepared by the same procedures as Synthesis Examples 1-1-1 and 1-1-2 except that protecting agent 8 was used instead of methoxymethyl chloride. Two-step yield 80%.

Synthesis Example 1-12

Synthesis of Monomer 12

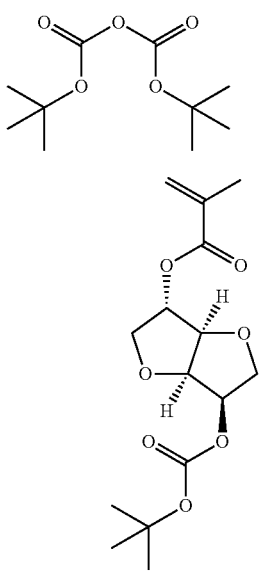

protecting agent 9

Monomer 12

Monomer 12 was prepared by the same procedures as Synthesis Examples 1-1-1 and 1-1-2 except that protecting agent 9 was used instead of methoxymethyl chloride. Two-step yield 62%.

Synthesis Example 1-13

Synthesis of Monomer 13

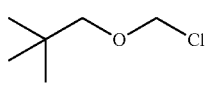

protecting agent 1 esterifying agent 1

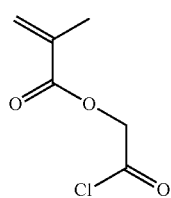

Monomer 13

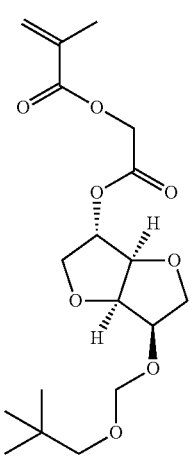

Monomer 13 was prepared by the same procedures as Synthesis Examples 1-1-1 and 1-1-2 aside from using protecting agent 1 instead of methoxymethyl chloride, and esterifying agent 1 instead of methacrylic anhydride. Two-step yield 59%.

Synthesis Example 1-14

Synthesis of Monomer 14 protecting agent 1

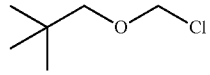

esterifying agent 2

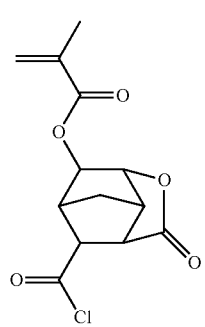

Monomer 14

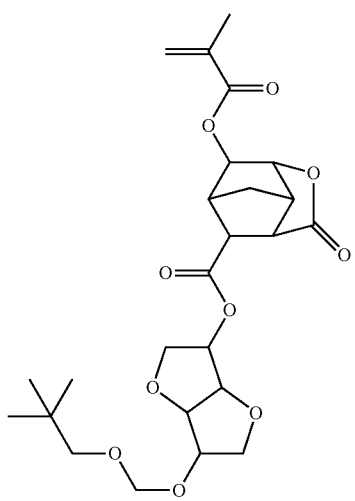

Monomer 14 was prepared by the same procedures as Synthesis Examples 1-1-1 and 1-1-2 aside from using protecting agent 1 instead of methoxymethyl chloride, and esterifying agent 2 instead of methacrylic anhydride. Two-step yield 60%.

Synthesis Example 1-15

Synthesis of Monomer 15 protecting agent 1

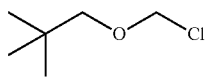

esterifying agent 3

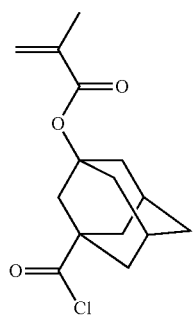

-continued

Monomer 15

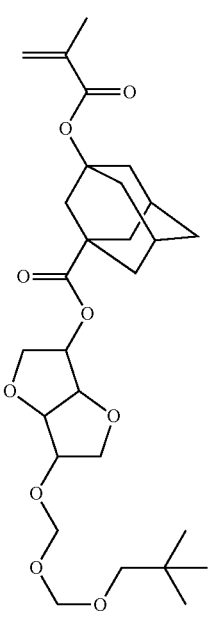

Monomer 15 was prepared by the same procedures as Synthesis Examples 1-1-1 and 1-1-2 aside from using protecting agent 1 instead of methoxymethyl chloride, and esterifying agent 3 instead of methacrylic anhydride. Two-step yield 63%.

Synthesis Example 1-16

Synthesis of Monomer 7

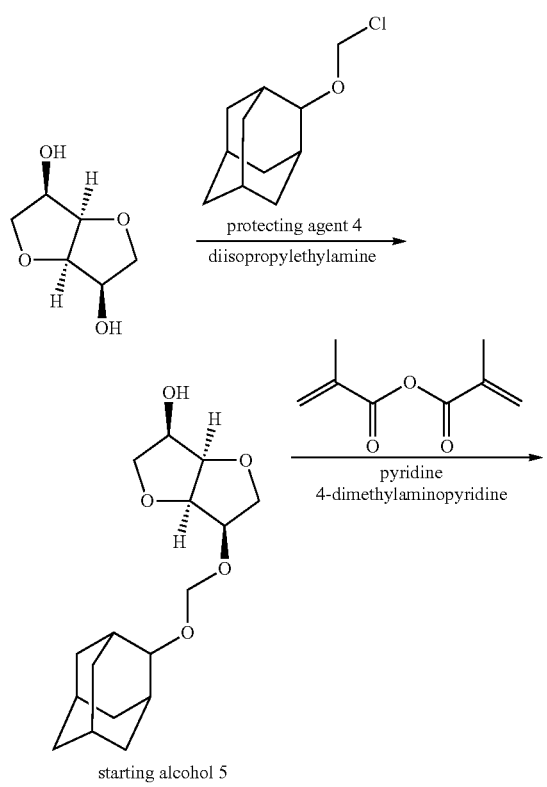

-continued

Monomer 7

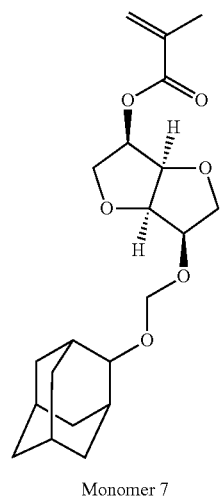

Synthesis Example 1-16-1

Synthesis of Starting Alcohol 5

Starting alcohol 5, which is a different isomer (of the above formula) from Synthesis Example 1-7-1, was prepared by the same procedure as Synthesis Example 1-1-1 aside from using isomannide instead of isosorbide, and protecting agent 4 instead of methoxymethyl chloride. Yield 78%.

$^1$H-NMR (600 MH in DMSO-$d_6$): δ=4.71-4.78 (3H, m), 4.43 (1H, t), 4.28 (1H, t), 4.14-4.20 (1H, m), 4.07-4.13 (1H, m), 3.89 (1H, t), 3.77 (1H, t), 3.70 (1H, m), 3.46 (1H, t), 3.34 (1H, t), 1.85-2.00 (4H, m), 1.70-1.80 (4H, m), 1.59-1.68 (4H, m), 1.40-1.47 (2H, m) ppm Example 1-16-2

Synthesis of Monomer 7

Monomer 7, which is a different isomer (of the above formula) from Synthesis Example 1-7-2, was prepared by the same procedure as Synthesis Example 1-1-2 except that starting alcohol 5 was used instead of starting alcohol 1. Yield 93%.

IR (D-ATR): ν=2903, 2852, 1722, 1637, 1450, 1383, 1315, 1296, 1167, 1114, 1096, 1079, 1050, 1038, 1025, 978, 928 cm$^{-1}$ $^1$H-NMR (600 MH in DMSO-$d_6$, only major isomer data): δ=6.03 (1H, m), 5.67-5.71 (1H, m), 5.09 (1H, q), 4.75 (2H, s), 4.66 (1H, t), 4.41 (1H, t), 4.12-4.17 (1H, m), 3.83-3.89 (2H, m), 3.76-3.81 (1H, m), 3.70 (1H, s), 3.40 (1H, t), 1.85-1.98 (7H, m), 1.71-1.80 (4H, m), 1.61-1.68 (4H, m), 1.43 (2H, d) ppm Monomer 1
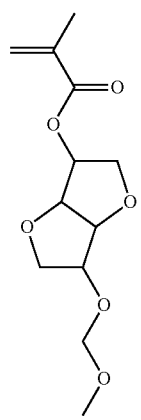
Monomer 2
Monomer 3
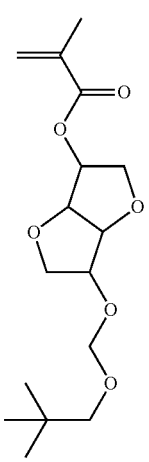
Monomer 4
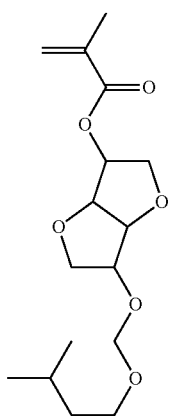
Monomer 5
Monomer 6
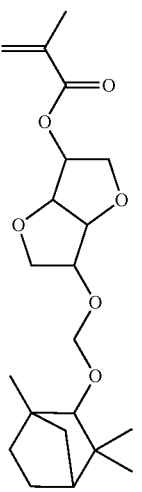

Monomer 7
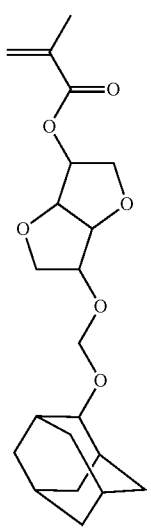
Monomer 8
Monomer 9
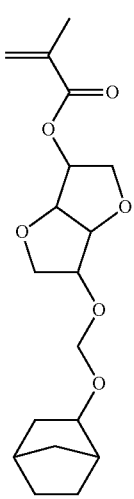
Monomer 10
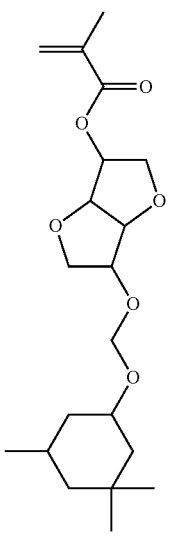
Monomer 11
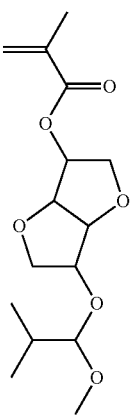
Monomer 12
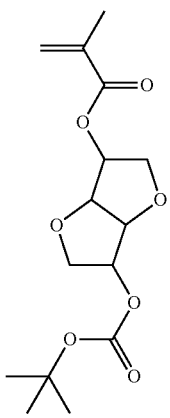

-continued

Monomer 13

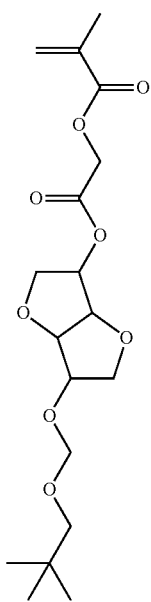

Monomer 14

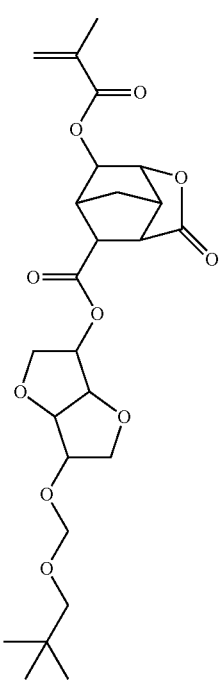

-continued

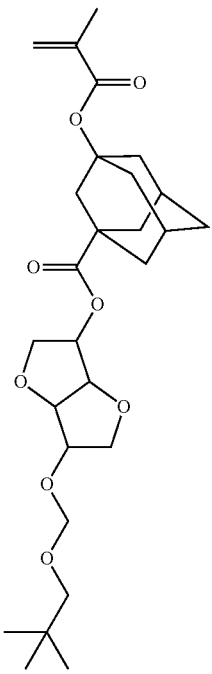

Momomer 15

Synthesis Example 2

Polymers within the scope of the invention were synthesized according to the following formulation.

Synthesis Example 2-1

Synthesis of Polymer 1

With stirring at 80° C. in nitrogen atmosphere, a solution of 36.4 g of Monomer 1, 13.6 g of 4,8-dioxatricyclo[4.2.1.0$^{3,7}$] nonan-5-on-2-yl methacrylate, 331 mg of 2,2'-azobisisobutyronitrile, and 394 mg of 2-mercaptoethanol in 87.5 g of PGMEA was added dropwise to 29.2 g of PGMEA over 4 hours. The mixture was stirred for a further 2 hours at 80° C. The reaction solution was cooled to room temperature, and with vigorous stirring, added dropwise to 1,000 mL of n-hexane. The resulting solids were collected by filtration and dried in vacuum at 50° C. for 15 hours, obtaining a polymer in white powder solid form, designated Polymer 1. The amount was 46.7 g in a yield of 93%. Polymer 1 had a compositional proportion and Mw as shown below.

Polymer 1

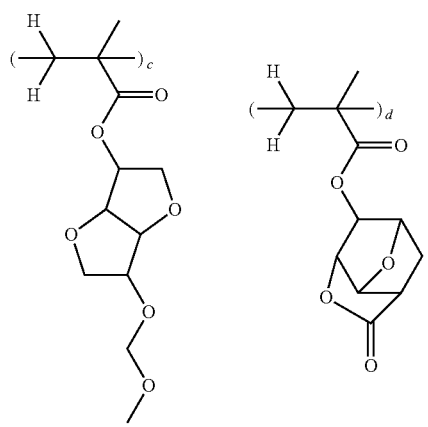

(c = 0.70, d = 0.30, Mw = 7,200)

Synthesis Examples 2-2 to 2-10 and Comparative Synthesis Examples 1-1 to 1-3

Synthesis of Polymers 2 to 10 and Comparative Polymers 1 to 3

Polymers 2 to 10 and Comparative Polymers 1 to 3 were synthesized by the same procedure as Synthesis Example 2-1 except that the type and proportion of monomers were changed. Their compositional proportion (in molar ratio) and Mw are shown below.

Polymer 2

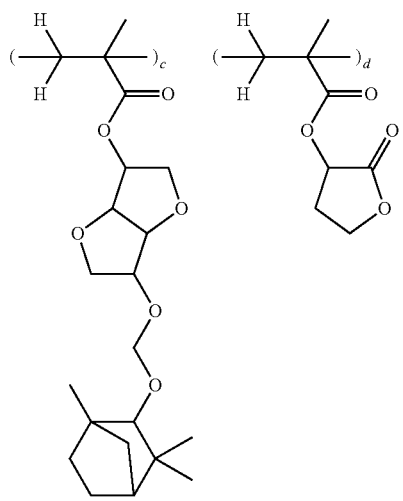

(c = 0.60, d = 0.40, Mw = 7,400)

Polymer 3

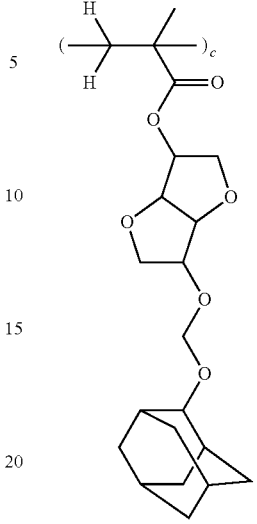 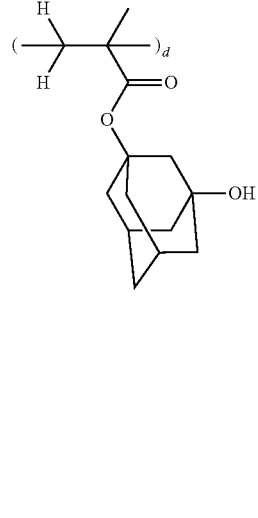

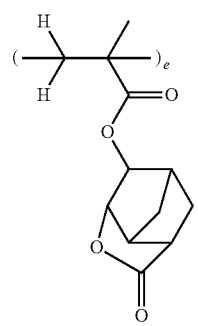

(c = 0.60, d = 0.10, e = 0.30, Mw = 7,600)

Polymer 4

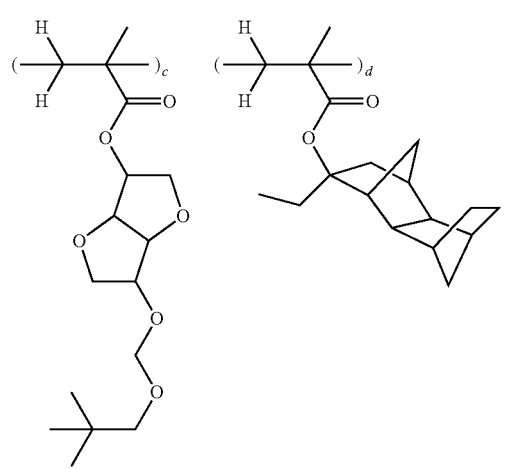

-continued
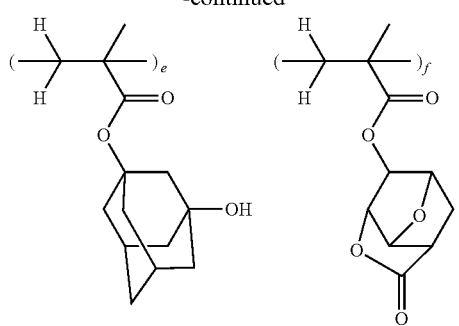
(c = 0.40, d = 0.20, e = 0.10, f = 0.30, Mw = 6,400)
Polymer 5
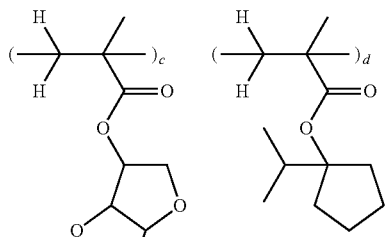
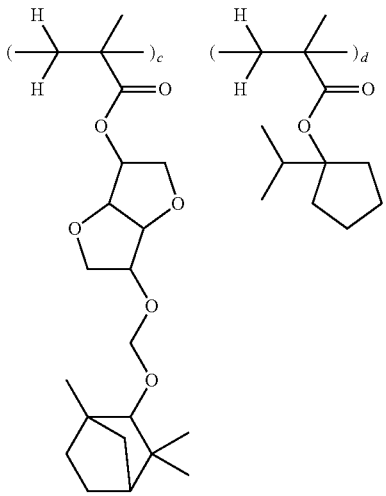
(c = 0.40, d = 0.20, e = 0.10, f = 0.30, Mw = 6,400)
Polymer 6
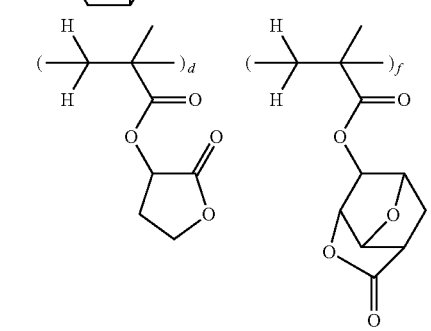
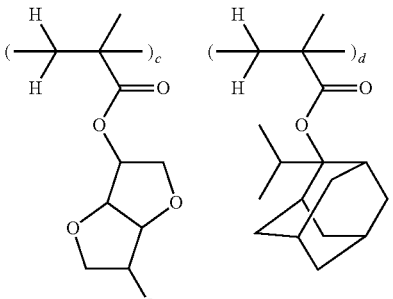
-continued
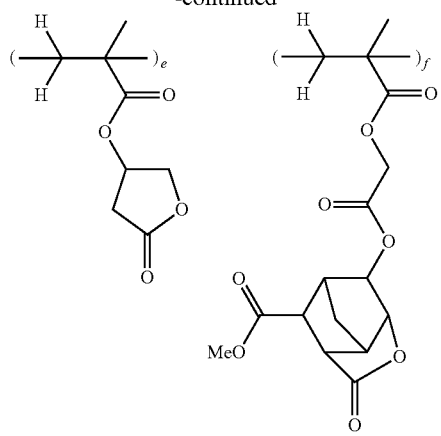
(c = 0.30, d = 0.20, e = 0.30, f = 0.20, Mw = 6,700)
Polymer 7
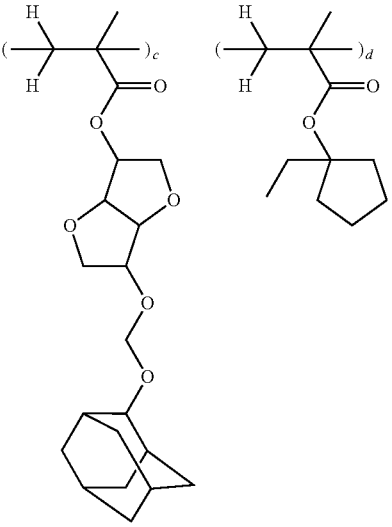
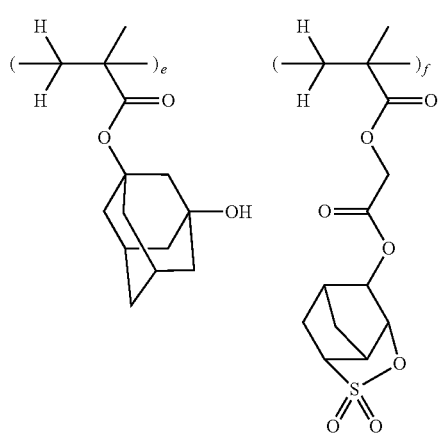
(c = 0.40, d = 0.20, e = 0.10, f = 0.30, Mw = 6,900)

Polymer 8
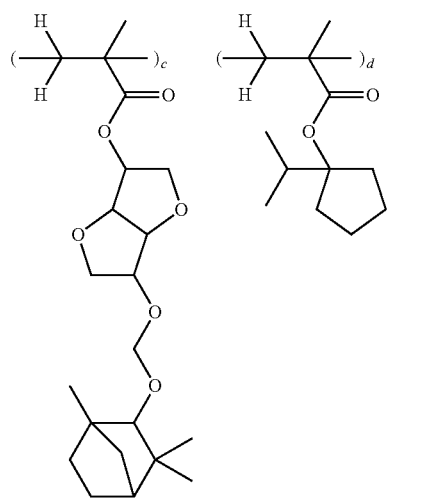
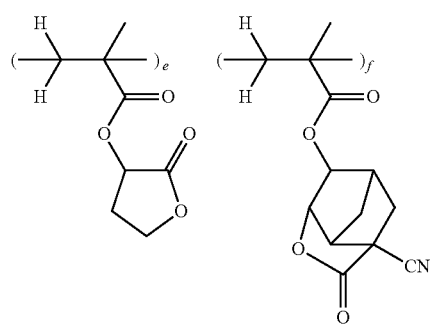
(c = 0.40, d = 0.20, e = 0.20, f = 0.20, Mw = 6,800)
Polymer 9
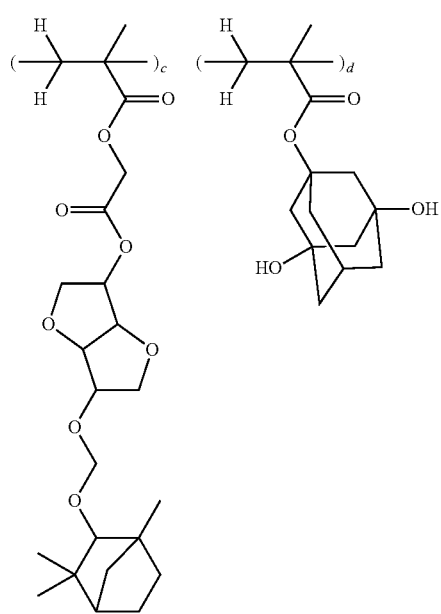
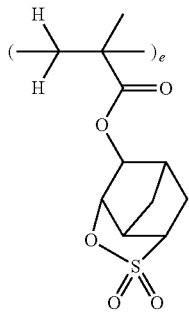
(c = 0.60, d = 0.20, e = 0.20, Mw = 6,800)
Polymer 10
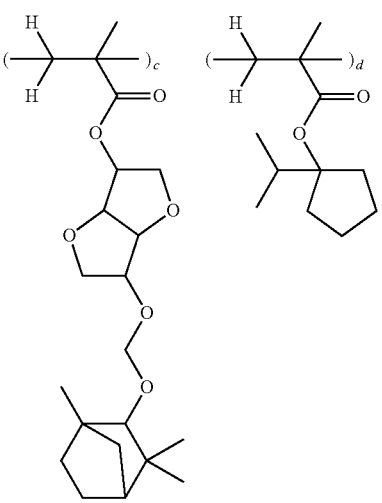
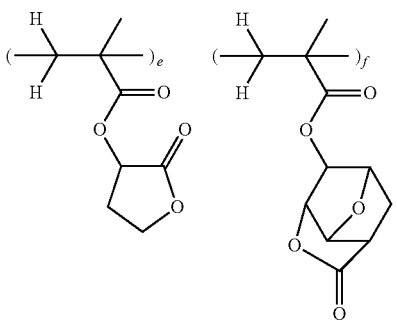
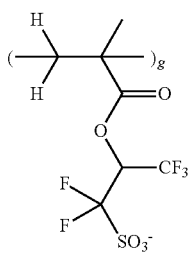
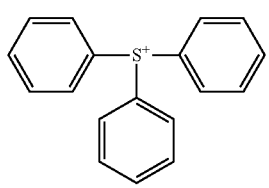
(c = 0.30, d = 0.20, e = 0.25, f = 0.20, g = 0.05, Mw = 6,700)

-continued

Comparative Polymer 1

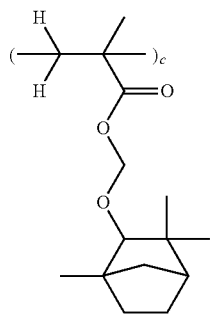

(c = 0.60, d = 0.40, Mw = 7,100)

Comparative Polymer 2

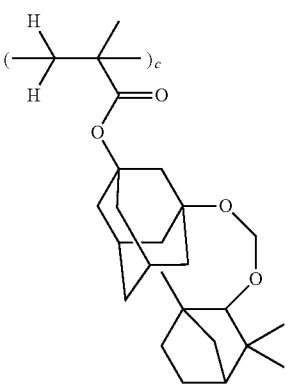

(c = 0.60, d = 0.40, Mw = 7,800)

Comparative Polymer 3

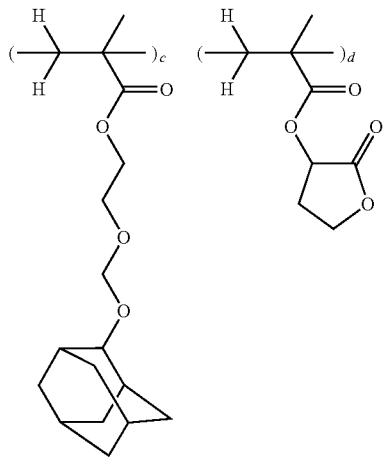

(c = 0.60, d = 0.40, Mw = 7,500)

Examples and Comparative Examples

Preparation of Resist Compositions

Examples 1-1 to 1-14 & Comparative Examples 1-1 to 1-3

Resist compositions were prepared by using inventive resins (Polymers 1 to 10) or comparative resins (Comparative Polymers 1 to 3) as the base resin, and dissolving the polymer, an acid generator (PAG-1 or 2), and a basic compound (Base-1) in a solvent mixture (PGMEA and CyHO) in accordance with the recipe shown in Table 1. These compositions were each filtered through a Teflon® filter having a pore diameter 0.2 thereby giving inventive resist solutions (R-01 to 14) and comparative resist solutions (R-15 to 17). Each solvent mixture contained 0.01 wt % of surfactant KH-20 (Asahi Glass Co., Ltd.).

TABLE 1

| | Resist | Resin (pbw) | PAG (pbw) | Base (pbw) | Solvent 1 (pbw) | Solvent 2 (pbw) |
|---|---|---|---|---|---|---|
| Example 1-1 | R-01 | Polymer 1 (80) | PAG-1 (15.0) | Base-1 (4.0) | PGMEA (2,700) | CyHO (300) |
| Example 1-2 | R-02 | Polymer 2 (80) | PAG-1 (15.0) | Base-1 (4.0) | PGMEA (2,700) | CyHO (300) |
| Example 1-3 | R-03 | Polymer 3 (80) | PAG-1 (15.0) | Base-1 (4.0) | PGMEA (2,700) | CyHO (300) |
| Example 1-4 | R-04 | Polymer 4 (80) | PAG-1 (15.0) | Base-1 (4.0) | PGMEA (2,700) | CyHO (300) |
| Example 1-5 | R-05 | Polymer 5 (80) | PAG-1 (15.0) | Base-1 (4.0) | PGMEA (2,700) | CyHO (300) |
| Example 1-6 | R-06 | Polymer 6 (80) | PAG-1 (15.0) | Base-1 (4.0) | PGMEA (2,700) | CyHO (300) |
| Example 1-7 | R-07 | Polymer 7 (80) | PAG-1 (15.0) | Base-1 (4.0) | PGMEA (2,700) | CyHO (300) |
| Example 1-8 | R-08 | Polymer 8 (80) | PAG-1 (15.0) | Base-1 (4.0) | PGMEA (2,700) | CyHO (300) |
| Example 1-9 | R-09 | Polymer 9 (80) | PAG-1 (15.0) | Base-1 (4.0) | PGMEA (2,700) | CyHO (300) |
| Example 1-10 | R-10 | Polymer 10 (80) | | Base-1 (4.0) | PGMEA (2,700) | CyHO (300) |
| Example 1-11 | R-11 | Polymer 4 (80) | PAG-1 (15.0) | Base-1 (4.0) | PGMEA (2,700) | GBL (300) |
| Example 1-12 | R-12 | Polymer 5 (80) | PAG-1 (15.0) | Base-1 (4.0) | PGMEA (2,700) | GBL (300) |
| Example 1-13 | R-13 | Polymer 4 (80) | PAG-2 (15.0) | Base-1 (4.0) | PGMEA (2,700) | CyHO (300) |

TABLE 1-continued

| | Resist | Resin (pbw) | PAG (pbw) | Base (pbw) | Solvent 1 (pbw) | Solvent 2 (pbw) |
|---|---|---|---|---|---|---|
| Example 1-14 | R-14 | Polymer 5 (80) | PAG-2 (15.0) | Base-1 (4.0) | PGMEA (2,700) | CyHO (300) |
| Comparative Example 1-1 | R-15 | Comparative Polymer 1 (80) | PAG-1 (15.0) | Base-1 (4.0) | PGMEA (2,700) | CyHO (300) |
| Comparative Example 1-2 | R-16 | Comparative Polymer 2 (80) | PAG-1 (15.0) | Base-1 (4.0) | PGMEA (2,700) | CyHO (300) |
| Comparative Example 1-3 | R-17 | Comparative Polymer 3 (80) | PAG-1 (15.0) | Base-1 (4.0) | PGMEA (2,700) | CyHO (300) |

The acid generator, base and solvent shown in Table 1 have the following meanings.
PAG-1: triphenylsulfonium 2-(adamantane-1-carbonyloxy)-1,1,3,3,3-pentafluoropropanesulfonate
PAG-2: 4-tert-butylphenyldiphenylsulfonium 2-(adamantane-1-carbonyloxy)-1,1,3,3,3-pentafluoropropane-sulfonate
Base-1: tri(2-methoxymethoxyethyl)amine
PGMEA: 1-methoxyisopropyl acetate
CyHO: cyclohexanone
GBL: γ-butyrolactone
Evaluation of Pattern Collapse and LWR Examples 2-1 to 2-14 & Comparative Examples 2-1 to 2-3

Each of inventive resist compositions (R-01 to 14) and comparative resist compositions (R-15 to 17) was spin coated on a silicon wafer having an antireflective coating (ARC-29A, Nissan Chemical Co., Ltd.) of 90 nm thick and baked at 100° C. for 60 seconds to form a resist film of 100 nm thick. On the resist film, a protective film material (SIOC-3 by Shin-Etsu Chemical Co., Ltd.) was spin coated and heat treated at 90° C. for 60 seconds to form a protective film of 50 nm thick. Using an ArF excimer laser immersion stepper (Nikon Corp., NA 1.30), the resist film was exposed through a 6% halftone phase shift mask bearing a predetermined pattern for pattern transfer. This was followed by bake (PEB) for 60 seconds and puddle development in a 2.38 wt % tetramethylammonium hydroxide aqueous solution for 30 seconds, forming a 40-nm 1:1 line-and-space pattern. During the PEB, an optimum temperature for each resist composition was employed.

The 40-nm 1:1 L/S pattern was observed under a top-down scanning electron microscope (TDSEM) to examine a pattern line width as a function of exposure dose. In general, as the dose increases, the line width decreases and the pattern is more prone to collapse. In the dose increasing test, the minimum line width above which the pattern did not collapse was determined. It is reported as "collapse threshold size" (nm, a smaller value being better). Further, a line portion of the 40-nm 1:1 L/S pattern was observed under SEM to determine a line width variation, which was reported as line width roughness (LWR). A smaller value of LWR indicates a less fluctuation of the line pattern and is better. The test results are shown in Table 2.

TABLE 2

| | Resist | PEB temperature | Collapse threshold size | LWR (3σ) |
|---|---|---|---|---|
| Example 2-1 | R-01 | 100° C. | 30 nm | 5.4 nm |
| Example 2-2 | R-02 | 90° C. | 30 nm | 5.5 nm |
| Example 2-3 | R-03 | 95° C. | 27 nm | 5.3 nm |
| Example 2-4 | R-04 | 95° C. | 27 nm | 5.2 nm |
| Example 2-5 | R-05 | 95° C. | 28 nm | 5.1 nm |
| Example 2-6 | R-06 | 90° C. | 29 nm | 5.3 nm |
| Example 2-7 | R-07 | 95° C. | 28 nm | 5.4 nm |
| Example 2-8 | R-08 | 95° C. | 27 nm | 5.4 nm |
| Example 2-9 | R-09 | 90° C. | 29 nm | 5.4 nm |
| Example 2-10 | R-10 | 95° C. | 26 nm | 5.0 nm |
| Example 2-11 | R-11 | 95° C. | 27 nm | 5.2 nm |
| Example 2-12 | R-12 | 95° C. | 28 nm | 5.1 nm |
| Example 2-13 | R-13 | 100° C. | 27 nm | 5.3 nm |
| Example 2-14 | R-14 | 100° C. | 26 nm | 5.2 nm |
| Comparative Example 1-1 | R-15 | 105° C. | 39 nm | 6.1 nm |
| Comparative Example 1-2 | R-16 | 105° C. | not resolved | — |
| Comparative Example 1-3 | R-17 | 100° C. | not resolved | — |

It is seen from the results of Table 2 that the resist compositions within the scope of the invention exhibit good pattern collapse resistance and minimized LWR when processed by ArF excimer laser immersion lithography.

Japanese Patent Application No. 2011-155417 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymerizable ester compound having the general formula (2):

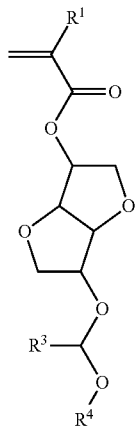

(2)

wherein $R^1$ is hydrogen, fluorine, methyl or trifluoromethyl, $R^3$ is hydrogen or a $C_1$-$C_{15}$ straight, branched or cyclic, monovalent hydrocarbon group, and $R^4$ is a $C_1$-$C_{15}$ straight, branched or cyclic, monovalent hydrocarbon group in which a constituent —$CH_2$— may be substituted by —O— or —C(=O)—.

2. A polymer comprising recurring units having the general formula (2b):

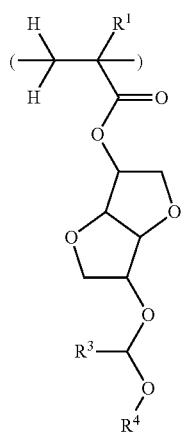

(2b)

wherein $R^1$ is hydrogen, fluorine, methyl, or trifluoromethyl, $R^3$ is hydrogen or a $C_1$-$C_{15}$ straight, branched, or cyclic, monovalent hydrocarbon group, and $R^4$ is a $C_1$-$C_{15}$ straight, branched, or cyclic, monovalent hydrocarbon group in which a constituent —$CH_2$— may be substituted by —O— or —C(=O)—.

3. The polymer of claim 2, further comprising recurring units of at least one type selected from the general formulas (2A) to (2D):

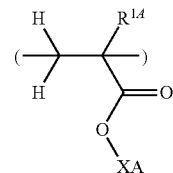

(2A)

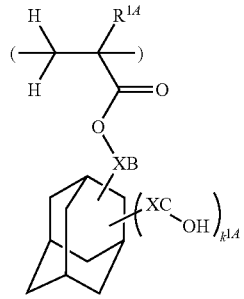

(2B)

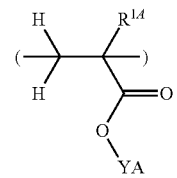

(2C)

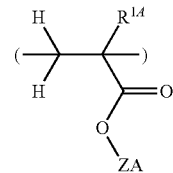

(2D)

wherein $R^{1A}$ is hydrogen, fluorine, methyl or trifluoromethyl, XA is an acid labile group, XB and XC are each independently a single bond, or a $C_1$-$C_4$ straight or branched divalent hydrocarbon group, YA is a substituent group having a lactone or sultone structure, ZA is hydrogen, a $C_1$-$C_{15}$ fluoroalkyl group, or a $C_1$-$C_{15}$ fluoroalcohol-containing substituent group, and $k^{1A}$ is an integer of 1 to 3.

4. The polymer of claim 2, further comprising recurring units of at least one type selected from the general formulas (d1) to (d3):

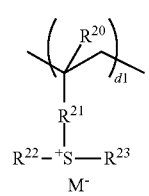

(d1)

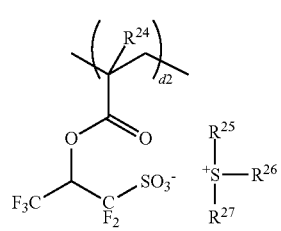

(d2)

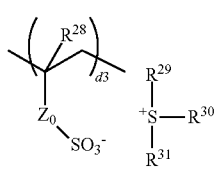
(d3)

wherein $R^{20}$, $R^{24}$ and $R^{28}$ each are hydrogen or methyl, $R^{21}$ is a single bond, phenylene, —O—$R^{33}$—, or —C(=O)—Y—$R^{33}$—, Y is oxygen or NH, $R^{33}$ is a $C_1$-$C_6$ straight, branched or cyclic alkylene group, alkenylene group or phenylene group, which may contain a carbonyl (—CO—), ester (—COO—), ether (—O—) or hydroxyl radical, $R^{22}$, $R^{23}$, $R^{25}$, $R^{26}$, $R^{27}$, $R^{29}$, $R^{30}$, and $R^{31}$ are each independently a $C_1$-$C_{12}$ straight, branched or cyclic alkyl group which may contain a carbonyl, ester or ether radical, or $C_6$-$C_{12}$ aryl group, $C_7$-$C_{20}$ aralkyl group or thiophenyl group, $Z_0$ is a single bond, methylene, ethylene, phenylene, fluorinated phenylene, —O—$R^{32}$—, or —C(=O)—$Z_1$—$R^{32}$—, $Z_1$ is oxygen or NH, $R^{32}$ is a $C_1$-$C_6$ straight, branched or cyclic alkylene, alkenylene or phenylene group, which may contain a carbonyl, ester, ether or hydroxyl radical, and $M^-$ is a non-nucleophilic counter ion.

5. A resist composition comprising a base resin comprising the polymer of claim 4, an acid generator, and an organic solvent.

6. A resist composition comprising a base resin comprising the polymer of claim 2, and an organic solvent.

7. A process for forming a pattern comprising the steps of applying the resist composition of claim 6 onto a substrate, baking the resist composition to form a resist film, exposing the resist film to high-energy radiation or electron beam through a photomask, optionally baking the exposed film, and developing it in a developer.

8. A process for forming a pattern comprising the steps of applying the resist composition of claim 6 onto a substrate, baking the resist composition to form a resist film, exposing the resist film to high-energy radiation or electron beam through a photomask, baking the exposed film, and developing it in a developer,
said exposing step being performed by immersion lithography including interposing a liquid having a refractive index of at least 1.0 between the resist film and a projection lens.

9. A process for forming a pattern comprising the steps of applying the resist composition of claim 6 onto a substrate, baking the resist composition to form a resist film, forming a protective film on the resist film, exposing the resist film to high-energy radiation or electron beam through a photomask, baking the exposed film, and developing it in a developer,
said exposing step being performed by immersion lithography including interposing a liquid having a refractive index of at least 1.0 between the protective film and a projection lens.

\* \* \* \* \*